(12) United States Patent
Zafiris

(10) Patent No.: US 12,377,199 B2
(45) Date of Patent: Aug. 5, 2025

(54) MEDICAL FLUID THERAPY SYSTEM AND METHOD EMPLOYING DISTILLATION

(71) Applicants: BAXTER INTERNATIONAL INC., Deerfield, IL (US); BAXTER HEALTHCARE SA, Glattpark (CH)

(72) Inventor: John Zafiris, Hawthorn Woods, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 451 days.

(21) Appl. No.: 17/795,661

(22) PCT Filed: Jan. 27, 2021

(86) PCT No.: PCT/US2021/015231
§ 371 (c)(1),
(2) Date: Jul. 27, 2022

(87) PCT Pub. No.: WO2021/154821
PCT Pub. Date: Aug. 5, 2021

(65) Prior Publication Data
US 2023/0091413 A1    Mar. 23, 2023

Related U.S. Application Data

(60) Provisional application No. 62/967,129, filed on Jan. 29, 2020.

(51) Int. Cl.
*A61M 1/16* (2006.01)
*A61M 1/14* (2006.01)

(52) U.S. Cl.
CPC ........ *A61M 1/1664* (2014.02); *A61M 1/1524* (2022.05); *A61M 1/155* (2022.05);
(Continued)

(58) Field of Classification Search
CPC .. A61M 1/1664; A61M 1/1524; A61M 1/155; A61M 1/1561; A61M 1/1565;
(Continued)

(56) References Cited

U.S. PATENT DOCUMENTS 4,947,983 A * 8/1990 Jost ..................... B01D 3/00
159/43.1
2020/0164129 A1* 5/2020 Wallenås ............... B01D 5/006

FOREIGN PATENT DOCUMENTS

WO    2017109760    6/2017
WO    2019013697    1/2019

OTHER PUBLICATIONS

International Search Report—PCT/US2021/015231 mailed May 18, 2021—3 pages.
(Continued)

*Primary Examiner* — Susan S Su
*Assistant Examiner* — Erin A Kim
(74) *Attorney, Agent, or Firm* — K&L Gates LLP

(57) ABSTRACT

A fluid purification unit is disclosed. In an example, a fluid purification unit includes a heater configured to boil a fluid. The heater includes first and second electrodes positioned and arranged to contact the fluid. The first and second electrodes are configured to receive electrical power, heat resistively due to the electrical power, and transfer the heat to the fluid to boil the fluid to form water vapor. The fluid purification unit also includes a condenser including (i) a thermally conductive flowpath configured to conductively cool the water vapor, and (ii) a cooling source configured to direct a cooling medium past the thermally conductive flowpath to convectively cool the water vapor. The conductive and convective cooling combines to condense the water vapor into purified water.

21 Claims, 18 Drawing Sheets

(52) U.S. Cl.
CPC ........ *A61M 1/1561* (2022.05); *A61M 1/1565* (2022.05); *A61M 1/159* (2022.05); *A61M 1/1672* (2014.02)

(58) Field of Classification Search
CPC .. A61M 1/159; A61M 1/1672; A61M 1/1656; A61M 2205/3653; A61M 1/166; A61M 1/1696; A61M 1/284; B01D 5/00; B01D 3/00
See application file for complete search history.

(56) References Cited

OTHER PUBLICATIONS

Written Opinion—PCT/US2021/015231 mailed May 18, 2021—6 pages.
International Preliminary Report on Patentability PCT/US2021/015231 mailed Jul. 28, 2022—7 pages.

* cited by examiner

MEDICAL FLUID THERAPY SYSTEM AND METHOD EMPLOYING DISTILLATION

PRIORITY CLAIM

This application is a national phase entry of PCT/US2021/015231, filed on Jan. 27, 2021, which claims priority to U.S. Provisional Application No. 62/967,129, filed on Jan. 29, 2020, the entire disclosures of which are incorporated by reference herein.

TECHNICAL FIELD

The present disclosure relates generally to medical fluid therapies and more particularly to medical fluid therapy systems that are capable of producing medical fluid at the point of use.

BACKGROUND

Certain medical fluid therapies employ pre-sterilized bags of treatment fluid. For example, peritoneal dialysis is typically performed in the patient's home. There are different types of peritoneal dialysis, including continuous ambulatory peritoneal dialysis ("CAPD") and automated peritoneal dialysis ("APD"). CAPD is a manual treatment in which the patient typically drains used dialysis fluid from the patient's peritoneal cavity and then causes fresh dialysis fluid to refill the peritoneal cavity. The fresh dialysis fluid is left to dwell for a period of time to remove waste, toxins and excess water into the dialysis fluid, after which the used fluid is drained to begin a new cycle.

APD is performed by a machine, which is sometimes referred to as a cycler because it performs the same cycles described above for CAPD. APD is typically performed at night, while the patient sleeps, and while the patient's indwelling peritoneal catheter is connected to a patient line extending to the APD machine. As with CAPD, if the patient at the start of treatment is full with used peritoneal dialysis ("PD") fluid, the APD machine initially drains the used fluid to a dedicated drain bag or to a house drain. Next, the APD machine fills the patient with fresh peritoneal dialysis fluid, which is left to dwell for a period of time to remove waste, toxins and excess water into the dialysis fluid. The APD machine repeats the above cycle until a prescribed amount of fresh peritoneal dialysis fluid has been delivered to the patient.

CAPD and APD typically use multiple bags per treatment, for example, two to four bags. CAPD may be performed multiple times during the day, while nighttime APD may be accompanied by a midday manual exchange. The number of bags per day multiplied by the number of days between treatment fluid deliveries results in the patient having to store boxes upon boxes of solution in their home. In many instances, a wall of a room is dedicated to storing PD solution and supplies.

Another way that medical fluid therapy fluids or solutions are prepared is to do so at the place of treatment, which is sometimes termed "online generation". Hemodialysis ("HD"), which cleans the patient's blood as opposed to using the patient's peritoneal cavity, typically makes HD dialysis fluid online. To do so, water first has to be purified to a level that is safe for treatment. Once HD concentrates have been added to the purified water, the resulting HD dialysis fluid is passed through a dialyzer, which also receives the patient's blood, to exchange waste, toxins and excess patient water across the dialyzer membranes and into the HD dialysis fluid. HD treatments are most often performed in a dialysis center, in which a large batch of highly purified water may be made for multiple HD dialysis machines located within the center.

In the center, noisy water purification equipment, such as pumps and reverse osmosis ("RO") units, can be located in a different room or otherwise away from the patient area. Also, because water purification may be centralized for multiple machines, equipment cost is reduced. Attempts have been made to make water purification units for home therapy systems, such as home dialysis systems. Some of the attempts have included a multitude of different purification technologies, such as carbon pretreatment packs, RO filtration, electrodeionization ("EDI"), resin beds, ultraviolet ("UV") radiation, ultrafiltration and others. While the combination of such technologies may yield ultrapure water, the resulting systems are complicated and expensive.

A need exists accordingly for an improved water purification device, which is suitable for use in medical fluid therapies, such as PD and HD, and for fluid therapy systems that are capable of producing medical fluid at the point of use.

SUMMARY

The devices, systems and methods of the present disclosure attempt to remedy the above-described problems. At the heart of each of the devices and systems discussed herein is a purified water generation unit that uses distillation to perform at least the bulk of the purification. The primary components of the water distillation unit may include a water tank for receiving tap water or other unpurified water, a heater for boiling the unpurified water to create steam, and a condenser to cool the steam to produce highly purified water, wherein impurities from the water are vented and/or collected at the bottom of the heater and delivered to drain. In an alternative embodiment, the tap water tank is not provided and tap water is instead delivered to the heater via house water pressure.

One or more type of finishing (polishing and/or sterilizing) filter may be located downstream from the condenser, such as, an electrodionization ("EDI") filter and/or one or more ultrafilter. The downstream finishing filter(s) in an embodiment further purifies the water exiting the condenser from a level of pure or ultrapure to being water for injection ("WFI") or of an injectable quality, which is suitable for use to form either peritoneal dialysis ("PD") fluid or a replacement fluid for a blood treatment therapy, such as hemofiltration ("HF") or hemodiafiltration ("HDF").

Optionally, a carbon filter may be placed between the water tank (or house water connection) and the heater to remove chloramines from the tap water prior to reaching the heater. Additionally, a pressure sensor may be located so as to sense pressure in the steam line located between the heater and the condenser. A vent line may be located downstream from the pressure sensor. Valves may be placed in the steam line and the vent line to selectively allow an overpressure in the steam line to be vented to atmosphere and/or volatiles that are freed from the heated water to be vented to atmosphere.

A temperature sensor is located in one embodiment so as to sense the temperature of the purified water exiting the condenser to ensure that the water is safe to be delivered to the point of use, e.g., a mixing location to be combined with concentrates to form a dialysis fluid. A pressure relief valve is also located along the condenser exit line in an embodiment to relieve excess pressure in the purified water prior to reaching the at least one finishing filter, if provided, or to the point of use if the at least one finishing filter is not provided.

The water distillation or purification unit may also include multiple conductivity sensors, such as a first conductivity sensor located adjacent to the temperature sensor in the condenser exit line and a second conductivity sensor located just prior to the exit of the WFI from the water distillation unit, e.g., just downstream from the at least one finishing filter.

In an embodiment, each of the heater, condenser, valves, pressure sensors, temperature sensor and conductivity sensors are under microprocessor control of a control unit for the water distillation or purification unit, which may include one or more processor and one or more memory. In an embodiment, the control unit includes a user interface having a display device under control of a video controller in communication with the at least one processor and the at least one memory. A touch screen overlay may be provided with the display device and/or electromechanical buttons, such as membrane switches, may be provided to enter information into the control unit. The control unit may also output to speakers for sounding alarms and alerts and/or to provide voice guidance instructions.

As discussed in detail below, the water distillation or purification unit outputs to a PD or blood treatment machine, which has its own control unit. It is contemplated for the control unit of the PD or blood treatment machine to be a master control unit, wherein the control unit of the water distillation or purification unit is a delegate control unit to the master control unit. Here, the master control unit of the PD or blood treatment machine tells the delegate control unit of the water distillation unit when purified water or WFI is needed and, for example, how much (e.g., data concerning demand). In an embodiment, the master control unit also instructs the delegate control unit as to what temperature the purified water or WFI is to be outputted. In this manner, the user only has to interact with the display device of the PD or blood treatment machine, which in turn controls the water distillation unit automatically. The control unit of the water generation or distillation unit may also communicate back to the control unit of the point of use machine information regarding capacity, e.g., how much can the distillation unit prepare in what time frame, or where the distillation unit is in a current batch cycle.

The master and delegate control units may be configured to communicate wired and/or wirelessly. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology. To communicate wirelessly, the master and delegate control units include transceivers operable with the one or more processing and memory.

In one embodiment, the water is heated by applying a large AC electrical potential to a pair of electrodes that are submerged in the tap water, wherein the electrodes are separated from each other such that current has to pass through the tap water to complete an electrical circuit. The electrodes are made of a medically compatible and at least somewhat electrically conductive material, such as stainless steel (e.g., 304 or 316) or titanium. The electrodes in an embodiment each include baffles that are interleaved within baffles of the other electrode, so as to increase the overall surface area of adjacently juxtaposed electrode material. The increased surface area increases the speed at which the heater boils the tap water.

The heater in one embodiment includes an electrically and thermally insulative disposable lining fitted into a rigid base into which the disposable electrodes are placed and held fixed in a non-contacting relationship. Electrical leads are inserted sealingly through a wall of the base and are placed into electrical communication with the electrodes. The electrical leads are connected to a power source, which for example is configured to apply 1000 to 2000 Watts of power to the electrical leads and therefore to the electrodes and tap water located between the electrodes.

A cover, e.g., an electrically and thermally insulative cover, is removeably, e.g., hingedly, connected to the base, such that the cover allows access to the disposable liner electrodes for replacement. The cover in one embodiment provides two ports, one for connection to a water source (tank or tap water directly), and another for connection to a steam line, which carries steam from the heater to the condenser.

As is known, the process of distillation involves separating components or substances, in the present case volatiles, from a liquid, in one example tap water, using selective boiling and condensation. The volatiles of the present distillation process are either collected at the bottom of the base of the heater and discharged intermittently from the heater to a drain via a drain valve and/or are vented through a vent in a vent line extending from the top of the heater. It has been found that the more volatile substances are vented to the atmosphere, while the least volatile substances are flushed to the drain. Water is of intermediate volatility. The most volatile substances boil first and the resultant gas is vented. Water boils next and the resulting gas (steam) is condensed back into liquid. The least volatile parts (including some water) never boil and are flushed to drain instead.

In one embodiment, the condenser includes a condensing coil, which is made of a thermally conductive and medically safe material, such as stainless steel (e.g., 304 or 316) or titanium. Plural heat fins, such as highly thermally conductive copper heat fins, are attached to the coil, e.g., via soldering, welding, brazing, gluing and/or mechanical connection. The heat fins conduct heat away from the coil and the steam located within the coil. The coil includes an inlet and an outlet, wherein the inlet is located at the top of the coil and the outlet is located at the bottom of the coil. In this manner, steam from the heater enters inlet at the top of the coil, while highly purified water exits the outlet at the bottom of the coil.

The condenser also includes a fan, which is located inside of the coil and associated heat fins. The fan in an embodiment has upper and lower fan blade holders that are attached respectively to upper and lower fixtures via bearings, such as ball or roller bearings. The upper and lower fan blade holders spin around a vertical axis of rotation extending through the centers of each of the bearings. The fan's blades are in an embodiment vertically disposed paddles or baffles that are formed with (e.g., a single molded piece) or are connected to the upper and lower fan blade holders so as to extend radially from the vertical axis of rotation. The upper and lower bearings are placed in a rotationally fixed relationship with upper and lower fixtures, so as to hold the fan blades firmly in place but allow the blades to spin freely about the central, vertical axis of the fan. In an alternative embodiment, the fan blades may be held fixed to a vertical shaft that extends along and spins around the length of the central, vertical axis of rotation.

The output shaft of a fan motor is coupled via a direct coupler, or via a geared or belt and pulley relationship as desired, to one of the fan blade holders. In operation, the fan motor, under control of the control unit for the water distillation or purification unit, causes the fan blade holder, the blades connected to the holder, and an opposing holder holding the other end of the fan blades to spin. The spinning of the blades in an embodiment pulls air in from above and below and drives air radially outwardly and over the copper heat fins connected to the condenser coil, causing convective heat transfer away from the steam traveling through the condenser coil.

In an embodiment, the control unit of the water purification unit is configured to receive (e.g., from the master control unit of the PD or blood treatment machine) a desired purified water exit temperature from the user. The control unit of the water purification unit in turn accesses a look-up table or algorithm that correlates the purified water exit temperature with the speed of the fan and boiler power. The control unit in turn sets the boiler power and fan speed to be the correlated fan speed for the desired water exit temperature. In this embodiment, the fan motor for the fan is a variable speed motor and the boiler power is variable. Providing water at a temperature elevated above ambient is advantageous for PD or blood treatment applications, which may require the resulting mixed dialysis fluid to be at or near body temperature, e.g., 37° C. Here, heating energy required at the PD or blood treatment machine is conserved and the time necessary for the resulting dialysis fluid to be suitable for treatment is lessened.

In an alternative embodiment, the fan motor is a single speed motor and the outlet condenser temperature of the purified water is whatever temperature is achieved via the single speed. The achieved temperature may be closer to ambient to preserve the life of the one or more downstream finishing filter. It should be appreciated however that the concern regarding high temperature and the deionizing resins has to do with the sterilization process. 37° C. water may degrade the resins a bit sooner versus room temperature water, however, more significant degradation occurs at temperatures closer to 100° C.

It is contemplated in alternative embodiments to provide other types of cooling for the condensing operation, such as water cooling. For example, if a tap water storage tank is provided, it is contemplated to place the condensing coil, e.g., without heat fins, which may again be made be from a medically safe material, such as, stainless steel (e.g., 304, 316) or titanium, in the tap water tank to (i) cool the steam from the heater and (ii) preheat the tap water so that power usage at the heater is reduced. Here, the control unit of the water distillation unit is programmed to make sure enough tap water is present in the water tank to adequately cool the condensing coil, even if some of the tap water is not eventually purified and is provided instead only for cooling. Multiple water cooled heat exchangers may be provided if desired to condense the steam.

The water purification or distillation unit just described is useful in many different applications. In a first application, the water purification unit is used to output WFI for mixing with PD concentrates, such as glucose and buffer concentrates, to prepare a PD solution for delivery to the patient. The water purification unit of the present disclosure may for example be used in place of water purifier 110 disclosed in US Publication No. 2017/0319770 ("the '770 Publication), entitled "Systems And Methods For Peritoneal Dialysis Having Point Of Use Dialysis Fluid Preparation Including Mixing And Heating Therefore", filed May 5, 2017, the entire contents of which are incorporated herein by reference and relied upon. The water purification unit of the present disclosure outputs water of the same quality (WFI) as that of water purifier 110 of the '770 Publication, and may do so at an elevated temperature so as to lessen the burden on the heater of cycler 20 of the '770 Publication, and so as to reduce preparation time of the dialysis fluid.

In a second application, the water purification unit of the present disclosure is used to output ultrapure water for mixing with HD concentrates, to prepare an HD solution for delivery to a dialyzer. Because the dialyzer provides another layer of filtration via its hollow fiber membranes, ultrapure water as opposed to WFI may suffice. Here, there is at least one finishing filter, discussed below, so the water purification unit may not be needed. The water purification unit of the present disclosure may for example be used in place of water supply 30 disclosed in U.S. Pat. No. 9,724,458 ("the '458 Patent), entitled "Hemodialysis System", filed May 24, 2012, the entire contents of which are incorporated herein by reference and relied upon. The water purification unit of the present disclosure outputs water of the same quality (ultrapure) as that of water supply 30 of the '458 Patent, and may do so at an elevated temperature so as to lessen the burden on the inline heater 72 of the '458 patent.

The pumping mechanisms of the '770 Publication and the '458 Patent are actuated pneumatically. It is contemplated however for the water purification unit of the present disclosure to operate with a PD cycler or HD machine having any suitable type of pumping mechanism, such as pneumatic pumping, peristaltic pumping (rotary or linear), gear pumping, platen pumping, volumetric pumping via a motor (e.g., stepper motor) connected to a rotary to linear motion conversion apparatus (e.g., lead screw), and combinations thereof. It is also contemplated for the water purification unit of the present disclosure to operate with a PD cycler or HD machine having any suitable type of heating, such as batch heating, inline heating, resistive heating, inductive heating, radiant heating, and combinations thereof. It is further contemplated for the water purification unit of the present disclosure to operate with a PD cycler or HD machine having any suitable type of valve actuation, such as pneumatic actuation, pinch valve actuation, spring actuation, and combinations thereof.

In a third application, the water purification unit of the present disclosure is used to output WFI for mixing with replacement fluid concentrates to prepare a replacement fluid for delivery to the patient. Replacement fluid, unlike HD dialysis fluid, is delivered directly into an extracaporeal circuit connected to the patient, e.g., upstream or downstream from a dialyzer. The water exiting from the water purification unit is accordingly of a WFI quality when used to prepare replacement fluid, e.g., for hemofiltration ("HF") or hemodialfiltration ("HDF"), for chronic or acute (e.g., continuous reneal replacement therapy ("CRRT")) treatment.

In the first three applications, the distillation unit of the present disclosure is used to purify water. It should be appreciated however that the present disclosure is not limited to the purification of water only and may be used to purify other fluids, such as used dialysis fluid, e.g., used PD or used HD fluid. In a PD example, the distillation unit may be provide with a storage tank that is filled to initially hold four liters of tap water, which the patient or patient's caregiver brings to the tank at the beginning of treatment. The distillation unit purifies an initial two liters of tap water, which is transferred to a water accumulator, such as water accumulator 66 of the '770 Publication. Once two liters of WFI is delivered to the water accumulator, the PD cycler makes two liters of PD dialysis fluid in the manner described in the '770 Publication in one embodiment, after which the two liters is delivered to the patient's peritoneum.

During the patient dwell period, the distillation unit purifies the remaining two liters of tap water, which is again transferred to the water accumulator. Once the second two liters of WFI is delivered to the water accumulator, the PD cycler makes a second two liters of PD dialysis fluid in the manner described in the '770 Publication in one embodiment. The second two liters of PD dialysis fluid is mixed and heated as needed in a heater/mixing bag, such as heater/mixing bag 62 of the '770 Publication. At the end of the dwell period, the PD cycler pumps used dialysis fluid from the patient into the storage tank of the distillation unit. The used dialysis fluid will include ultrafiltrate removed from the patient, so if two liters of dialysis fluid is delivered initially to the patient, some amount greater than two liters will be pumped from the patient to the storage tank of the distillation unit as ultrafiltrate. The storage tank is sized accordingly to hold the amount of ultrafiltrate removed from the patient over the course of treatment.

After the initial two liters of used dialysis fluid and ultrafiltrate is removed from the patient to the storage tank of the distillation unit, the PD cycler pumps the second two liters of dialysis fluid from the heater/mixing bag to the patient to begin a second dwell period. During the second dwell period, the distillation unit boils the used dialysis fluid delivered from the storage tank and condenses the steam into ultrapure water, which the one or more finishing filter purifies into WFI, which is stored in the water accumulator. Once two liters of WFI is generated in the water accumulator, the PD cycler pulls the two liters of WFI into the heater/mixing bag along with PD concentrates to form a third batch of fresh PD dialysis fluid for treatment. The third batch of PD dialysis fluid is mixed and heated in the heater/mixing bag until the second patient dwell period is completed.

It is worth noting that because the impurities removed from the dialysis fluid come from the patient, they are unwanted but nevertheless biologically compatible. The water produced from the used dialysis fluid therefore does not have to be ultrapure, just cleaner than the effluent removed from the patient. For example, if the purified effluent is only 80% cleaner after distillation (not ultrapure or WFI), the water may nevertheless be adequate to perform additional treatment, perhaps over a longer dwell period, e.g., 20% longer. Here, the formulation of the concentrates mixed with the purified water may be compensated for the residual impurities. It is also contemplated that if ultrapure water or WFI is not needed, the resulting water purification unit can be simplified, e.g., be smaller and not need any or as many finishing filters, for example.

The above-described cycle of removing used dialysis fluid from the patient to the storage tank of the distillation unit, filling the patient with freshly made dialysis fluid, distilling and polishing/sterilizing the used dialysis fluid into WFI, and pumping the WFI along with PD concentrates to form PD dialysis fluid in the heater/mixing bag is repeated until the patient's prescribed number of fill, dwell and drain cycles is completed. It should be appreciated that many times the patient begins treatment already full of PD fluid from a midday exchange or from the previous night's treatment. Here, the patient or caregiver only has to fill the storage tank of the distillation unit with a single fill amount of tap water (e.g., two liters) because the second fill amount is provided from the patient. And here, the PD cycler in a first machine step in the new treatment delivers used dialysis fluid from the patient to the storage tank to mix with the tap water added by the patient or caregiver.

Likewise, at the end of treatment, if a last fill is to be delivered to the patient that the patient carries after disconnection from the PD cycler, then the treatment ends upon the last fill, such that only a single fill volume's worth of used dialysis fluid, along with the accumulated UF from the patient resides in the storage tank. The patient or caregiver removes the storage tank from the distillation unit at the end of the treatment and discards the used fluid to a house drain. In an embodiment, any volatiles, waste, toxins or other residuals removed from the spent dialysis fluid into the heater of the distillation unit may be removed automatically or manually from the heater to the storage tank and into the used dialysis fluid prior to removal of the storage tank from the distillation unit.

It is contemplated to provide a volume or weight measuring device, e.g., one or more load cell, in the distillation unit beneath the storage tank, so that it may be known or approximated when a fill volume's worth (e.g., two liters) of WFI has been produced via removal of tap water, used dialysis fluid, or combinations thereof from the storage tank. Because a one-to-one ratio between tap water removed and WFI produced does not exist, an empirically determined factor, e.g., twenty-five percent, may be added to the amount tap water removed to assume a desired amount of WFI production. In any case, the control units of the distillation unit and the PD cycler may communicate wired or wirelessly, such that the distillation control unit sends a signal to the PD control unit when enough WFI is present in the water accumulator, such that the PD cycler may begin to make fresh dialysis fluid using the WFI. The weigh scale does not need to be precise because the PD cycler measures the amount of WFI removed from the water accumulator precisely for mixing with the PD concentrates. It is more important to make sure that enough WFI is present in the water accumulator to ensure that the PD cycler is able to prepare the prescribed fill volume's worth of PD. To that end, a certain percentage more (e.g., ten percent) than the proscribed fill volume's worth of WFI may be distilled and delivered to the water accumulator. Likewise, that extra amount of tap water is filled by the patient or caregiver initially into the storage container.

Lab scale models of the distillation unit have shown that two liters of WFI may be produced in about forty-eight minutes when applying 1875 Watts of power to the distillation heater. It is contemplated to limit the power to 1500 Watts or lower (to lower therapy cost and potentially per electrical code limit, e.g., NEC in the US) for residential use. For HD or PD in settings other than a home, or with an imposed limitation for use with only 20 A circuits, the available power increases, approaching 2400 Watts (in the U.S. at 20 A/120 VAC), causing a commensurate increase in water generating capacity per unit time. Typical PD dwell times can be one hour or longer, allowing plenty of time for new WFI to be mixed and heated to form fresh dialysis fluid ready for use. One major advantage of the present point of use system using the water purification or distillation unit of the present disclosure is that a connection to house water is not needed. Also, the drain volume is contained and manageable. Further, if it can be shown that the water accumulator can be sterilized properly prior to treatment, and maintained in a sterilized manner, then the disposable water accumulator may become a non-disposable part of the water purification or distillation unit, reducing overall disposable cost.

The water purification or distillation unit of the present disclosure may also be used to convert used HD fluid into ultrapure water or WFI for reuse. One primary difference between PD and HD is that HD requires significantly more dialysis fluid than does PD and is typically a continuous rather than a batch treatment. The PD system and methodology described above is a batch or continuous cycling peritoneal dialysis ("CCPD") system. It is contemplated however to use the water purification or distillation unit with a continuous flow peritoneal dialysis ("CFPD") system, which would instead operate more like the HD system described next.

A suitable HD dialysis fluid flowrate is 200 mL/min. Suppose that the distillation unit has the same capability in the HD system as in the PD system, namely, that two liters of WFI may be produced in about forty-eight minutes when applying 1875 Watts of power to the distillation heater. At a dialysis fluid flowrate is 200 mL/min, the two liters or 2000 mL of dialysis fluid would be consumed in ten minutes. It is possible to (i) provide multiple parallel heaters, (ii) upsize the heaters, (iii) lower the dialysis fluid flowrate, or (iv) provide a combination of (i) to (iii). Each of (i) to (iii) has cost or performance downsides. Each of (i) to (iii) also assumes a single pass of the dialysis fluid through the dialyzer. Another option is to allow the dialysis fluid to circulate through the dialyzer a number of times. Chances are the dialysis fluid has not used even close to all of its osmotic or cleaning capacity the first time it is flowed through the dialyzer. Using the above numbers, the two liters of dialysis fluid could be pumped through the dialyzer five times at 200 mL/min, providing fifty minutes for the distillation unit to prepare another two liters of ultrapure water or WFI (again, only ultrapure is needed for pure HD).

The HD system, like the PD system, includes the tap water storage tank, which again receives four liters of water initially but is sized to hold an additional amount of UF removed from the patient. The HD system, like the PD system, also includes a water accumulator (such as a mixing tank or deaeration tank), which stores the two liters of ultrapure water or WFI. The HD system may store the ultrapure water in a mixing tank to mix with HD concentrates to form HD dialysis fluid. The HD system alternatively employs a deaeration container that receives, holds and deaerates the WFI prior to being mixed with acid and bicarbonate concentrates.

In the HD system, at least four liters of tap water are placed in the tap water storage tank (later becoming the drain). The distillation unit prepares two liters of ultrapure water or WFI, which is stored in the mixing or deaeration chamber. In the example where water is stored in the mixing chamber, a dialysis fluid preparation unit prepares two liters of HD dialysis fluid using the ultrapure water or WFI and HD concentrates in the mixing chamber and then delivers the HD dialysis fluid to the deaeration container. Once two liters of dialysis fluid are placed in the deaeration container, two actions may begin in parallel, namely, (i) dialysis fluid may be cycled through the dialyzer (e.g., two liters, five times, at 200 mL/min), while the patient's blood is also pumped through the dialyzer and (ii) the distillation unit prepares the second two liters of ultrapure water or WFI, which is stored in the mixing chamber. At the end of the dialysis fluid circulation cycle, two more actions occur in parallel, namely, (a) used dialysis fluid and UF is delivered to the water storage tank (now drain) and (b) a second batch of two liters of HD dialysis fluid is created by mixing ultrapure water or WFI in the mixing chamber with HD concentrates and storing the mixed HD dialysis fluid in the deaeration container. Once this is done, the distillation unit distills the used dialysis fluid and UF into ultrapure water or WFI and delivers same to the mixing chamber. The above process is repeated until treatment is completed, e.g., four to six dialysis fluid circulation cycles.

The above process may be performed alternatively by delivering ultrapure water or WFI first to the deaeration chamber. Deaerated and heated water is then delivered to the mixing chamber to produce HD dialysis fluid.

It is contemplated again to place a volume or weight measuring device, e.g., one or more load cell, in the distillation unit beneath the storage tank, so that it may be known or approximated when the two liters of ultrapure water or WFI has been produced via removal of tap water, used dialysis fluid, or combinations thereof from the storage tank.

In light of the disclosure herein and without limiting the disclosure in any way, in a first aspect of the present disclosure, which may be combined with any other aspect listed herein, an a fluid purification unit includes: a heater configured to boil a fluid, the heater including first and second electrodes positioned and arranged to contact the fluid, the first and second electrodes configured to receive electrical power, heat resistively due to the electrical power, and transfer the heat to the fluid to boil the fluid to form a vaporized fluid such as water vapor; and a condenser including (i) a thermally conductive flowpath configured to conductively cool the water vapor, and (ii) an airflow or cooling source configured to direct air or a cooling medium past the thermally conductive flowpath to convectively cool the water vapor, the conductive and convective cooling combining to condense the water vapor into purified water.

In a second aspect of the present disclosure, which may be combined with any other aspect listed herein, the fluid purification unit is configured to accept either unpurified water or used dialysis fluid as the fluid to be boiled.

In a third aspect of the present disclosure, which may be combined with any other aspect listed herein, the heater includes an insulative base into which the electrodes are placed, wherein the base is sized to hold a desired amount of the fluid to be boiled.

In a fourth aspect of the present disclosure, which may be combined with any other aspect listed herein, the insulative base of the third aspect is at least one of (i) configured to hold the first and second electrodes such that the electrodes reside adjacent to one another in a non-contacting relationship, or (ii) sealingly receives first and second electrical leads that supply electrical power from an electrical power source to the first and second electrodes, respectively.

In a fifth aspect of the present disclosure, which may be combined with any other aspect listed herein, the insulative base is removable and disposable.

In a sixth aspect of the present disclosure, which may be combined with any other aspect listed herein, the heater includes an insulative cover connected to the insulative base of the third aspect so as to allow access to the first and second electrodes, the cover providing at least one port for at least one of (i) connection to a water source, or (ii) connection to a vaporized fluid line.

In a seventh aspect of the present disclosure, which may be combined with any other aspect listed herein, the first electrode includes first baffles and the second electrode includes second baffles, the first and second baffles interleaved with respect to each other.

In an eighth aspect of the present disclosure, which may be combined with any other aspect listed herein, the fluid purification unit includes a fluid storage tank positioned and arranged to provide fluid to the heater.

In a ninth aspect of the present disclosure, which may be combined with any other aspect listed herein, the thermally conductive flowpath of the condenser includes a thermally conductive coil.

In a tenth aspect of the present disclosure, which may be combined with any other aspect listed herein, the thermally conductive coil of the ninth aspect includes a plurality of heat fins for transferring heat from the water vapor.

In an eleventh aspect of the present disclosure, which may be combined with any other aspect listed herein, the airflow source of the condenser includes a fan positioned and arranged to blow air past the thermally conductive flowpath to convectively cool the water vapor.

In a twelfth aspect of the present disclosure, which may be combined with any other aspect listed herein, the thermally conductive flowpath of the condenser includes a thermally conductive coil, and wherein the fan of the eleventh aspect is positioned and arranged within the thermally conductive coil to blow air outwardly through the coil.

In a thirteenth aspect of the present disclosure, which may be combined with any other aspect listed herein, the fluid purification unit includes at least one finishing filter located downstream of the condenser to further purify the purified water.

In a fourteenth aspect of the present disclosure, which may be combined with any other aspect listed herein, a fluid purification unit includes: a heater configured to boil a fluid, the heater including first and second electrodes positioned and arranged to contact the fluid, the first and second electrodes configured to receive electrical power, heat resistively due to the electrical power, and transfer the heat to the fluid to boil the fluid to form water vapor; and a condenser including (i) a thermally conductive coil positioned to receive and carry water vapor from the heater, and (ii) a fan positioned and arranged within the thermally conductive coil to blow air outwardly through the coil.

In a fifteenth aspect of the present disclosure, which may be combined with any other aspect listed herein, the thermally conductive coil of the fourteenth aspect is arranged to receive water vapor at a top of the coil and to discharge purified water at a bottom of the coil, and wherein the fan includes paddles arranged to spin around an at least substantially vertical axis to blow air outwardly through the coil.

In a sixteenth aspect of the present disclosure, which may be combined with any other aspect listed herein, the fluid purification unit includes a control unit configured to control a speed of the fan of the fourteenth aspect so as to provide purified water at a desired temperature.

In a seventeenth aspect of the present disclosure, which may be combined with any other aspect listed herein, the fluid purification unit includes a temperature sensor located downstream from the condenser and in communication with the control unit of the sixteenth aspect.

In an eighteenth aspect of the present disclosure, which may be combined with any other aspect listed herein, the thermally conductive coil of the fourteenth aspect includes heat fins, and wherein the coil is made from a first metal and the heat fins are made from a second metal.

In a nineteenth aspect of the present disclosure, which may be combined with any other aspect listed herein, a fluid purification unit includes: a control unit; a heater configured to receive electrical power to boil a fluid, the control unit controlling electrical power to the heater; a condenser including a thermally conductive flowpath configured to receive water vapor from the heater, and an airflow source configured to direct air past the thermally conductive flowpath to cool the water vapor, the airflow source under control of the control unit; and at least one valve positioned at least one of upstream of the heater or between the heater and the condenser, the at least one valve under control of the control unit.

In a twentieth aspect of the present disclosure, which may be combined with any other aspect listed herein, the fluid preparation unit includes a vent line to atmosphere located between the heater and the condenser of the nineteenth aspect, the vent line operable with a vent valve under control of the control unit.

In a twenty-first aspect of the present disclosure, which may be combined with any other aspect listed herein, a peritoneal dialysis system includes: a peritoneal dialysis fluid pump arranged to pump peritoneal dialysis fluid to and from a patient; a peritoneal dialysis fluid preparation structure configured to combine water for injection ("WFI") with at least one peritoneal dialysis fluid concentrate to form peritoneal dialysis fluid; and a water purification unit including (i) a heater configured to boil unpurified water, the heater including first and second electrodes positioned and arranged to contact the unpurified water, the first and second electrodes configured to receive electrical power, heat resistively due to the electrical power, and transfer the heat to the unpurified water to boil the unpurified water to form water vapor, (ii) a condenser including a thermally conductive flowpath configured to accept and condense the water vapor, and (iii) at least one finishing filter positioned to receive and further purify the condensed water vapor into WFI for use with the peritoneal dialysis fluid preparation structure.

In a twenty-second aspect of the present disclosure, which may be combined with any other aspect listed herein, the peritoneal dialysis fluid preparation structure of the twenty-first aspect employs the peritoneal dialysis fluid pump to combine water for injection ("WFI") with the at least one peritoneal dialysis fluid concentrate.

In a twenty-third aspect of the present disclosure, which may be combined with any other aspect listed herein, the peritoneal dialysis fluid preparation structure of the twenty-first aspect employs a pump different than the peritoneal dialysis fluid pump to combine water for injection ("WFI") with the at least one peritoneal dialysis fluid concentrate.

In a twenty-fourth aspect of the present disclosure, which may be combined with any other aspect listed herein, the peritoneal dialysis fluid preparation structure of the twenty-first aspect is housed with the peritoneal dialysis fluid pump.

In a twenty-fifth aspect of the present disclosure, which may be combined with any other aspect listed herein, the peritoneal dialysis fluid pump of the twenty-first aspect is provided with the peritoneal dialysis fluid preparation structure as part of a peritoneal dialysis cycler.

In a twenty-sixth aspect of the present disclosure, which may be combined with any other aspect listed herein, the peritoneal dialysis fluid pump of the twenty-first aspect is under control of a first control unit and the water purification unit is under control of a second control unit, the first and second control units in data communication concerning at least one of (i) demand for WFI or (ii) capacity to produce WFI.

In a twenty-seventh aspect of the present disclosure, which may be combined with any other aspect listed herein, the thermally conductive flowpath of the condenser of the twenty-first aspect includes a thermally conductive coil.

In a twenty-eighth aspect of the present disclosure, which may be combined with any other aspect listed herein, the thermally conductive coil of the twenty-seventh aspect includes a plurality of heat fins for transferring heat from the water vapor.

In a twenty-ninth aspect of the present disclosure, which may be combined with any other aspect listed herein, the condenser further includes a fan positioned and arranged within the thermally conductive coil so as to drive air through the coil of the twenty-seventh aspect.

In a thirtieth aspect of the present disclosure, which may be combined with the twenty-first aspect in combination with any other aspect listed herein, the first electrode includes first baffles and the second electrode includes second baffles, the first and second baffles interleaved so as to be adjacent to one another in a non-contacting relationship.

In a thirty-first aspect of the present disclosure, which may be combined with any other aspect listed herein, a hemodialysis system includes: at least one hemodialysis fluid pump arranged to pump hemodialysis fluid to and from a dialyzer; a hemodialysis fluid preparation structure configured to combine purified water with at least one hemodialysis fluid concentrate to form hemodialysis fluid; and a water purification unit including (i) a heater configured to boil unpurified water, the heater including first and second electrodes positioned and arranged to contact the unpurified water, the first and second electrodes configured to receive electrical power, heat resistively due to the electrical power, and transfer the heat to the unpurified water to boil the unpurified water to form water vapor, (ii) a condenser including a thermally conductive flowpath configured to accept and condense the water vapor to form purified water, and optionally (iii) at least one finishing filter positioned to receive and further purify the condensed water vapor into WFI for use with the peritoneal dialysis fluid preparation structure.

In a thirty-second aspect of the present disclosure, which may be combined with any other aspect listed herein, the hemodialysis fluid preparation structure of the thirty-first aspect employs a pump different than the at least one hemodialysis fluid pump to combine purified water with the at least one hemodialysis fluid concentrate.

In a thirty-third aspect of the present disclosure, which may be combined with any other aspect listed herein, the hemodialysis fluid preparation structure of the thirty-first aspect is housed with the hemodialysis machine.

In a thirty-fourth aspect of the present disclosure, which may be combined with any other aspect listed herein, the hemodialysis fluid pump of the thirty-first aspect is provided with the hemodialysis fluid preparation structure as part of a hemodialysis machine.

In a thirty-fifth aspect of the present disclosure, which may be combined with any other aspect listed herein, the hemodialysis fluid pump of the thirty-first aspect is under control of a first control unit and the water purification unit is under control of a second control unit, the first and second control units in data communication concerning at least one of (i) demand for purified water or (ii) capacity to produce purified water.

In a thirty-sixth aspect of the present disclosure, which may be combined with any other aspect listed herein, the hemodialysis system of the thirty-first aspect is configured such that the hemodialysis fluid pump recirculates hemodialysis fluid through the dialyzer a plurality of times.

In a thirty-seventh aspect of the present disclosure, which may be combined with any other aspect listed herein, the thermally conductive flowpath of the condenser of the thirty-first aspect includes a thermally conductive coil.

In a thirty-eighth aspect of the present disclosure, which may be combined with any other aspect listed herein, the thermally conductive coil of the thirty-seventh aspect includes a plurality of heat fins for transferring heat from the water vapor.

In a thirty-ninth aspect of the present disclosure, which may be combined with any other aspect listed herein, the condenser further includes a fan positioned and arranged within the thermally conductive coil of the thirty-seventh aspect so as to drive air through the coil.

In a fortieth aspect of the present disclosure, which may be combined with the thirty-first aspect in combination with any other aspect listed herein, the first electrode includes first baffles and the second electrode includes second baffles, the first and second baffles interleaved so as to be adjacent to one another in a non-contacting relationship.

In a forty-first aspect of the present disclosure, which may be combined with any other aspect listed herein, a replacement fluid system includes: a replacement fluid pump arranged to pump replacement fluid to and from an arterial or venous line for connection to a patient; a replacement fluid preparation structure configured to combine water for injection ("WFI") with at least one replacement fluid concentrate to form replacement fluid; and a water purification unit including (i) a heater configured to boil unpurified water, the heater including first and second electrodes positioned and arranged to contact the unpurified water, the first and second electrodes configured to receive electrical power, heat resistively due to the electrical power, and transfer the heat to the unpurified water to boil the unpurified water to form water vapor, (ii) a condenser including a thermally conductive flowpath configured to accept and condense the water vapor, and (iii) at least one finishing filter positioned to receive and further purify the condensed water vapor into WFI for use with the replacement fluid preparation structure.

In a forty-second aspect of the present disclosure, which may be combined with any other aspect listed herein, the replacement fluid system of the forty-first aspect is a hemofiltration, hemodialfiltration or continuous renal replacement system.

In a forty-third aspect of the present disclosure, which may be combined with any other aspect listed herein, a peritoneal dialysis system includes: a peritoneal dialysis fluid cycler; a disposable unit operable with the peritoneal dialysis fluid cycler to pump peritoneal dialysis fluid to and from a patient; a peritoneal dialysis fluid mixing container in fluid communication with the disposable unit, the mixing container configured to accept water for injection ("WFI") and at least one peritoneal dialysis fluid concentrate to form fresh peritoneal dialysis fluid; and a distillation unit including (i) an unpurified water/used peritoneal dialysis fluid storage tank for accepting unpurified water, the unpurified water/used peritoneal dialysis fluid storage tank in fluid communication with the disposable unit for accepting used peritoneal dialysis fluid; (ii) a heater in fluid communication with the unpurified water/used peritoneal dialysis fluid storage tank, the heater configured to boil the unpurified water and the used peritoneal dialysis fluid to form water vapor, (iii) a condenser including a thermally conductive flowpath configured to accept and condense the water vapor, and (iv) at least one finishing filter positioned to receive and further purify the condensed water vapor into WFI for use in the mixing container to form peritoneal dialysis fluid.

In a forty-fourth aspect of the present disclosure, which may be combined with any other aspect listed herein, the peritoneal dialysis system of the forty-third aspect includes at least one control unit programmed to cause (i) used peritoneal dialysis fluid to be delivered from the patient to the unpurified water/used peritoneal dialysis fluid storage tank via the cycler operating the disposable set, (ii) fresh peritoneal dialysis fluid to be delivered from the mixing container to the patient via the cycler operating the disposable set, and (iii) used peritoneal dialysis fluid to be purified into WFI via the distillation unit.

In a forty-fifth aspect of the present disclosure, which may be combined with any other aspect listed herein, the used dialysis fluid in (i) is previously formed via WFI made in the distillation unit of the forty-fourth aspect from an initial amount of unpurified water.

In a forty-sixth aspect of the present disclosure, which may be combined with any other aspect listed herein, wherein the at least one control unit of the forty-fourth aspect includes a first control unit for the peritoneal dialysis fluid cycler and a second control unit for the distillation unit, the first and second control units in data communication to perform at least one of (i) to (iii).

In a forty-seventh aspect of the present disclosure, which may be combined with any other aspect listed herein, the peritoneal dialysis system of the forty-third aspect includes a water accumulator positioned to receive WFI from the at least one finishing filter, the water accumulator in fluid communication with the disposable set.

In a forty-eighth aspect of the present disclosure, which may be combined with any other aspect listed herein, the peritoneal dialysis system of the forty-seventh aspect includes at least one control unit programed to cause (i) an amount of unpurified water from the storage tank to be purified into WFI via the distillation unit and to be delivered to the water accumulator, (ii) WFI from the water accumulator to be delivered via the cycler operating the disposable set to the mixing container to mix with the at least one peritoneal dialysis fluid concentrate to form fresh peritoneal dialysis fluid, (iii) the fresh peritoneal dialysis fluid from the mixing container to be delivered via the cycler operating the disposable set to the patient, and (iv) used peritoneal dialysis fluid to be delivered from the patient to the storage tank via the cycler operating the disposable set.

In a forty-ninth aspect of the present disclosure, which may be combined with any other aspect listed herein, the at least one control unit of the forty-eighth aspect is further programmed to cause (v) a second amount of unpurified water from the storage tank to be purified into WFI via the distillation unit and to be delivered to the water accumulator after (ii) is performed and before (iv) is performed.

In a fiftieth aspect of the present disclosure, which may be combined with the forty-ninth aspect in combination with any other aspect listed herein, the at least one control unit is further programmed such that after the WFI from (v) is delivered from the water accumulator via the cycler operating the disposable set to the mixing container to mix with the at least one peritoneal dialysis fluid concentrate to form fresh peritoneal dialysis fluid, (vi) used peritoneal dialysis fluid delivered in (iv) to the storage tank is purified into WFI via the distillation unit and is delivered to the water accumulator.

In a fifty-first aspect of the present disclosure, which may be combined with the forty-ninth aspect in combination with any other aspect listed herein, the at least one control unit is further programmed such that after (vi), (vii) second used peritoneal dialysis fluid is delivered from the patient via the cycler operating the disposable set to the storage tank.

In a fifty-second aspect of the present disclosure, which may be combined with the fifty-first aspect in combination with any other aspect listed herein, the at least one control unit includes a first control unit for the peritoneal dialysis fluid cycler and a second control unit for the distillation unit, the first and second control units in data communication to perform at least one of (i) to (vii).

In a fifty-third aspect of the present disclosure, which may be combined with the forty-seventh aspect in combination with any other aspect listed herein, the water accumulator is provided as part of the disposable set.

In a fifty-fourth aspect of the present disclosure, which may be combined with the forty-third aspect in combination with any other aspect listed herein, wherein the heater includes first and second electrodes positioned and arranged to contact the unpurified water or the used peritoneal dialysis fluid, the first and second electrodes configured to receive electrical power, heat resistively due to the electrical power, and transfer the heat to the unpurified water or the used peritoneal dialysis fluid to boil the unpurified water or the used peritoneal dialysis fluid to form water vapor.

In a fifty-fifth aspect of the present disclosure, which may be combined with the forty-third aspect in combination with any other aspect listed herein, the thermally conductive flowpath of the condenser includes a thermally conductive coil.

In a fifty-sixth aspect of the present disclosure, which may be combined with the fifty-fifth aspect in combination with any other aspect listed herein, the thermally conductive coil includes a plurality of heat fins for transferring heat from the water vapor.

In a fifty-seventh aspect of the present disclosure, which may be combined with the fifty-fifth aspect in combination with any other aspect listed herein, the condenser further includes a fan positioned and arranged within the thermally conductive coil so as to drive air through the coil.

In a fifty-eighth aspect of the present disclosure, which may be combined with any other aspect listed herein, a hemodialysis system includes: a hemodialysis fluid pump positioned and arranged to pump hemodialysis fluid to a dialyzer; a hemodialysis fluid preparation unit in fluid communication with the hemodialysis fluid pump, the hemodialysis fluid preparation unit configured to accept purified water and at least one hemodialysis fluid concentrate to form fresh hemodialysis fluid; and a distillation unit including (i) an unpurified water/used hemodialysis fluid storage tank for accepting unpurified water, the unpurified water/used hemodialysis fluid storage tank in selective fluid communication with the dialyzer for accepting used hemodialysis fluid; (ii) a heater in fluid communication with the unpurified water/used hemodialysis fluid storage tank, the heater configured to boil the unpurified water and the used hemodialysis fluid to form water vapor, and (iii) a condenser including a thermally conductive flowpath configured to accept and condense the water vapor to form purified water.

In a fifty-ninth aspect of the present disclosure, which may be combined with the fifty-eighth aspect in combination with any other aspect listed herein, the hemodialysis system is configured such that the hemodialysis fluid pump recirculates an amount of hemodialysis fluid multiple times through the dialyzer to form the used hemodialysis fluid for delivery to the unpurified water/used hemodialysis fluid storage tank.

In a sixtieth aspect of the present disclosure, which may be combined with the fifty-eighth aspect in combination with any other aspect listed herein, the hemodialysis system includes at least one control unit programmed to cause (i) used hemodialysis fluid to be delivered from the dialyzer to the unpurified water/used hemodialysis fluid storage tank, (ii) fresh hemodialysis dialysis fluid to be delivered from the hemodialysis fluid preparation unit to the dialyzer via the hemodialysis fluid pump, and (iii) used hemodialysis fluid to be purified into purified water via the distillation unit.

In a sixty-first aspect of the present disclosure, which may be combined with the sixtieth aspect in combination with any other aspect listed herein, the used hemodialysis fluid in (i) is previously formed via purified water made in the distillation unit from an initial amount of unpurified water.

In a sixty-second aspect of the present disclosure, which may be combined with the sixtieth aspect in combination with any other aspect listed herein, the at least one control unit includes a first control unit for at least one of the hemodialysis fluid pump or the hemodialysis fluid preparation unit and a second control unit for the distillation unit, the first and second control units in data communication to perform at least one of (i) to (iii).

In a sixty-third aspect of the present disclosure, which may be combined with the fifty-eighth aspect in combination with any other aspect listed herein, the hemodialysis system includes a water accumulator positioned to receive purified water from the condenser, the water accumulator in fluid communication with the hemodialysis fluid preparation unit.

In a sixty-fourth aspect of the present disclosure, which may be combined with the sixty-third aspect in combination with any other aspect listed herein, the hemodialysis system includes at least one control unit programed to cause (i) an amount of unpurified water from the storage tank to be purified into purified water via the distillation unit and to be delivered to the water accumulator, (ii) purified water from the water accumulator to be delivered to the hemodialysis fluid preparation unit to mix with the at least one hemodialysis fluid concentrate to form fresh hemodialysis fluid, (iii) the fresh hemodialysis fluid from the hemodialysis fluid preparation unit to be delivered to the dialyzer, and (iv) used hemodialysis fluid to be delivered from the dialyzer to the storage tank.

In a sixty-fifth aspect of the present disclosure, which may be combined with the sixty-fourth aspect in combination with any other aspect listed herein, the at least one control unit is further programmed to cause (v) a second amount of unpurified water from the storage tank to be purified into purified water via the distillation unit and to be delivered to the water accumulator after (ii) is performed and before (iv) is performed.

In a sixty-sixth aspect of the present disclosure, which may be combined with the sixty-fifth in combination with any other aspect listed herein, the at least one control unit is further programmed such that after the purified water from (v) is delivered from the water accumulator to the hemodialysis fluid preparation unit to mix with the at least one hemodialysis fluid concentrate to form fresh hemodialysis fluid, (vi) used hemodialysis fluid delivered in (iv) to the storage tank is purified into purified water via the distillation unit and is delivered to the water accumulator.

In a sixty-seventh aspect of the present disclosure, which may be combined with the sixty-fifth in combination with any other aspect listed herein, the at least one control unit is further programmed such that after (vi), (vii) second used hemodialysis fluid is delivered from the dialyzer to the storage tank.

In a sixty-eighth aspect of the present disclosure, which may be combined with the sixty-seventh in combination with any other aspect listed herein, the at least one control unit includes a first control unit for at least one of the hemodialysis fluid pump or the hemodialysis fluid preparation unit and a second control unit for the distillation unit, the first and second control units in data communication to perform at least one of (i) to (vii).

In a sixty-ninth aspect of the present disclosure, which may be combined with the sixty-third aspect in combination with any other aspect listed herein, the water accumulator includes a mixing tank or a deaeration tank of the hemodialysis fluid preparation unit.

In a seventieth aspect of the present disclosure, which may be combined with the fifty-eighth aspect in combination with any other aspect listed herein, the heater includes first and second electrodes positioned and arranged to contact the unpurified water or the used hemodialysis fluid, the first and second electrodes configured to receive electrical power, heat resistively due to the electrical power, and transfer the heat to the unpurified water or the used hemodialysis fluid to boil the unpurified water or the used hemodialysis fluid to form water vapor.

In a seventy-first aspect of the present disclosure, which may be combined with the fifty-eighth aspect in combination with any other aspect listed herein, the thermally conductive flowpath of the condenser includes a thermally conductive coil.

In a seventy-second aspect of the present disclosure, which may be combined with the seventy-first aspect in combination with any other aspect listed herein, the thermally conductive coil includes a plurality of heat fins for transferring heat from the water vapor.

In a seventy-third aspect of the present disclosure, which may be combined with the seventy-first aspect in combination with any other aspect listed herein, the condenser further includes a fan positioned and arranged within the thermally conductive coil so as to drive air through the coil.

In a seventy-fourth aspect of the present disclosure, which may be combined with any other aspect listed herein, a renal replacement machine includes: a renal replacement fluid pump positioned and arranged to pump renal replacement fluid to a blood line in fluid communication with a blood filter; a renal replacement fluid preparation unit in fluid communication with the renal replacement fluid pump, the renal replacement fluid preparation unit configured to accept water for injection ("WFI") and at least one renal replacement fluid concentrate to form fresh renal replacement fluid; and a distillation unit including (i) an unpurified water/used renal replacement fluid storage tank for accepting unpurified water, the unpurified water/used renal replacement fluid storage tank in fluid communication with the blood filter for accepting used renal replacement fluid; (ii) a heater in fluid communication with the unpurified water/used renal replacement fluid storage tank, the heater configured to boil the unpurified water and the used renal replacement fluid to form water vapor, (iii) a condenser including a thermally conductive flowpath configured to accept and condense the water vapor, and (iv) at least one finishing filter positioned to receive and further purify the condensed water vapor into WFI for use in the renal replacement fluid preparation unit to form renal replacement fluid.

In a seventy-fifth aspect of the present disclosure, any of the structure and functionality disclosed in connection with FIGS. 1 to 17 may be combined with any of the other structure and functionality disclosed in connection with FIGS. 1 to 17.

In light of the present disclosure and the above aspects, it is therefore an advantage of the present disclosure to provide a water purification and dialysis fluid distillation unit.

It is another advantage of the present disclosure to provide a water purification or distillation unit that is configured to prepare water for injection ("WFI"), ultrapure water, or more purified water, e.g., from purified effluent.

It is a further advantage of the present disclosure to provide a water purification or distillation unit that is quieter and more economical to use.

It is still another advantage of the present disclosure to provide a dialysis system with lessened disposable storage requirements.

It is still a further advantage of the present disclosure to provide a more convenient dialysis system for patients while traveling.

It is yet another advantage of the present disclosure to provide a dialysis fluid reuse platform useful for peritoneal dialysis, hemodialysis, hemofiltration, hemodiafiltration, nutrition, medical delivery and saline, and/or lactated ringer production.

The advantages discussed herein may be found in one, or some, and perhaps not all of the embodiments disclosed herein. Additional features and advantages are described herein, and will be apparent from, the following Detailed Description and the figures.

DETAILED DESCRIPTION

System Overview

Figure 1:
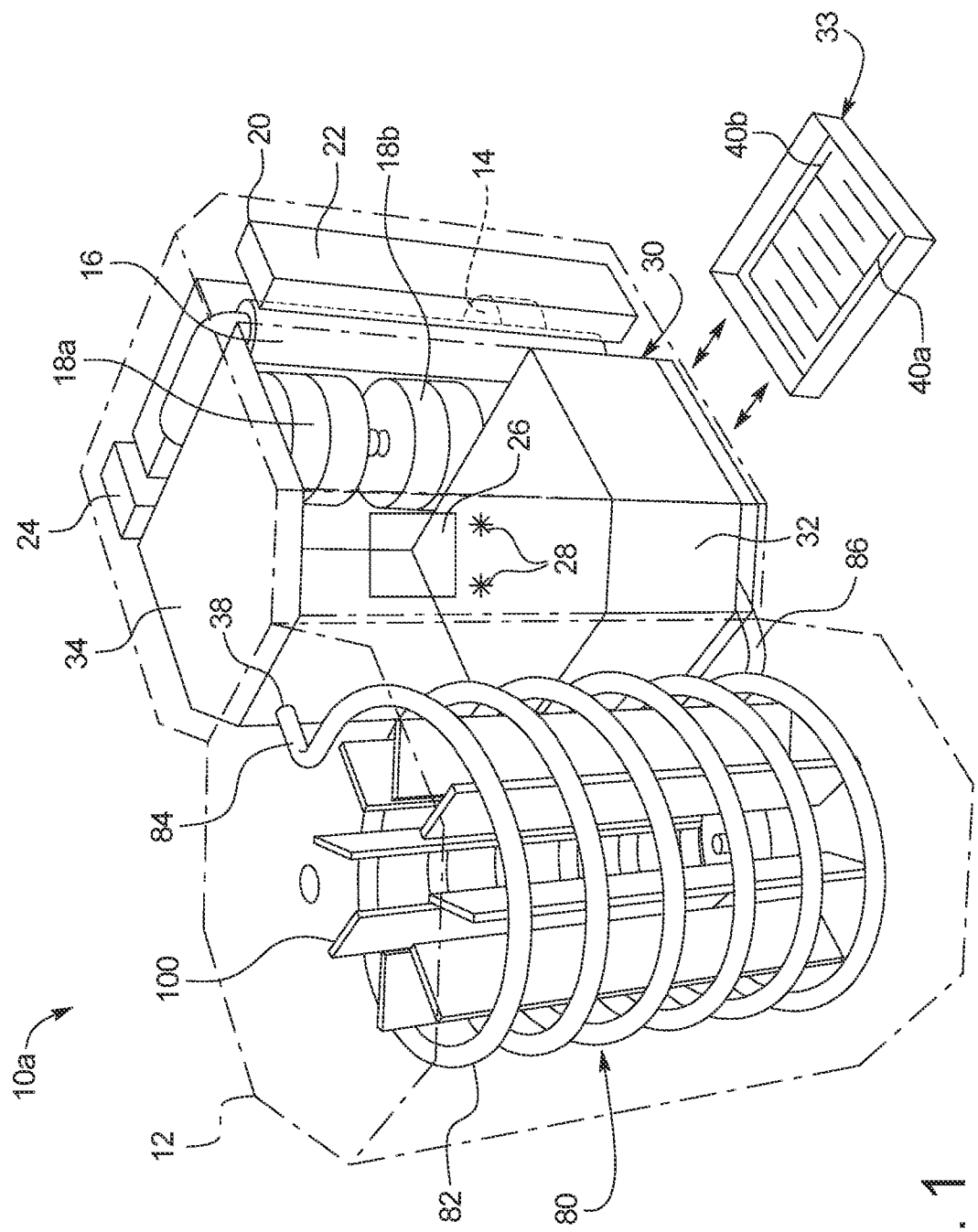
FIG. 1 is a perspective view of one embodiment of a purified water generation unit or distillation unit of the present disclosure.

Referring now to the drawings and in particular to FIG. 1, at the heart of each of the systems discussed herein is a purified water generation unit. As discussed herein, the terms purified water generation unit, fluid purification unit, water purification unit, and distillation unit may be used interchangeably. FIG. 1 shows a distillation unit 10a that uses distillation to perform at least the bulk of the purification. Purified water generation unit or distillation unit 10a in in the illustrated embodiment includes a housing 12 that holds an optional water tank 20 for receiving tap water or other generally unpurified water, a heater 30 for boiling the unpurified water to create steam, and a condenser 80 to cool the steam to produce highly purified water, wherein impurities or volatiles from the water are collected at the bottom of heater 30 and delivered to a drain, vented to atmosphere, and/or held in a disposable heater chamber to be disposed along with the chamber. Unpurified water tank 20 in the illustrated embodiment includes a bottom and sidewalls 22, which form an open top to receive unpurified water from a user (e.g., by opening a lid of housing 12). Unpurified water tank 20 is in one embodiment removable from housing 12 to empty unused water or used dialysis fluid as discussed in detail below. In an alternative embodiment, unpurified water tank 20 is not provided and unpurified water is instead delivered to heater 30 via house water pressure.

FIG. 1 also illustrates that a predistillation filter 14, such a granulated activated carbon ("GAC") filter, may be provided upstream of heater 30, e.g., between storage tank 20 (or house water connection) and heater 30 to remove chloramines from the tap water prior to reaching the heater. One or more type of finishing filter, e.g., polishing filter 16, and sterilizing filter(s) 18a/18b may be located downstream from condenser 80. In the illustrated embodiment, two different types of finishing filters are provided, such as, a polishing electrodionization ("EDI") or filter or deionizing resin 16 and a pair of sterilizing ultrafilters 18a and 18b. Filter 16 may be a small permanent or semi-permanent EDI filter or a disposable deionizing resin, wherein disposable here may mean being replaced after two or more months. Ultrafilters 18a and 18b in an embodiment are equal to or less than 0.2 micron filters and may be semi-permanent or disposable, e.g., replaced every six months to a year.

The need for any one or more of predistillation filter 14 or finishing filters 16, 18a/18b may be dependent on the type of application into which water generation unit or distillation unit 10a is placed. Downstream finishing filters 16, 18a/18b further purify the water exiting condenser 80 from being pure or ultrapure to being water for injection ("WFI") or of an injectable quality, which is suitable for use to form either peritoneal dialysis ("PD") fluid or a replacement fluid for a blood treatment therapy, such as hemofiltration ("HF") or hemodiafiltration ("HDF"). Here, EDI filter 16 and/or one or more of ultrafilter 18a and/or 18b may be used as needed to achieve a WFI level. The use of predistillation filter 14 may be application-based, for example, depending upon the prevalence and/or tolerance for chloramines.

Certain applications for water generation unit or distillation unit 10a for PD or hemodialysis ("HD"), do not require WFI or even ultrapure water, where purified water is sufficient instead. With HD, (i) the treatment does not require the HD fluid to be delivered directly to the patient, the HD fluid being delivered instead across the outsides of the dialyzer membranes and (ii) even if the HD fluid somehow reaches the patient's extracaporeal blood flow, it will have traversed through the hollow fiber membranes, which act as a final stage filter.

In FIG. 1, tap or other unfiltered water is supplied to storage tank 20, which feeds water through predistillation filter 14. Alternatively, tap or other unfiltered water is supplied directly to predistillation filter 14. The tap or other unfiltered water flows via gravity or water pump pressure from storage tank 20 (if provided), through predistillation filter 14, to heater 30. The tap or other unfiltered water flows via house water pressure through predistillation filter 14, to heater 30 if storage tank 20 is not provided. Heater 30 in the illustrated embodiment includes a thermally insulative base 32, which includes a disposable heater assembly that accepts tap or other unfiltered water from predistillation filter 14. The disposable heater assembly holds the heating electrodes discussed herein. The tap or other unfiltered water is boiled within thermally insulative base 32 of heater 30 as discussed in detail below. Thermally insulative base 32 in one embodiment includes a removable thermoformed plastic pan or tray 33 that is removed (perhaps also with the heating electrodes) after one or more treatment to discard collected volatiles. Pan or tray 33 (perhaps along with the heating electrodes) may be reinserted after removal and cleaning. Or a new tray 33 (perhaps along with new heating electrodes) may be inserted, if for example, the collected volatiles become caked onto the tray (and electrodes) or are otherwise not readily removed from the tray (or electrodes). In another embodiment, pan or tray 34 is not provided and instead the entire base 32 (perhaps including the heating electrodes) is cleaned and reused or is replaced (perhaps along with the heating electrodes) after one or more treatment. Heater 30 also includes a cover 34, e.g., an electrically and thermally insulative cover, which may be removeably, e.g., hingedly, connected to base 32.

Vaporized water or steam is collected within cover 34. The only place for the steam to escape is through a coil 82 (e.g., a thermally conductive flowpath) of condenser 80 (note that during an early phase of distillation, steam can also be vented to atmosphere through a valve, e.g., placed in vent line 60c discussed in connection with FIG. 2). Coil 82 is a thermally conductive coil, e.g., made of stainless steel and copper fins (fins illustrated below), and includes a coil inlet 84 and a coil outlet 86. The steam condenses as it travels downwardly in a spiral pattern from coil inlet 84 to coil outlet 86. The steam has condensed into purified water by the time it has reached coil outlet 86. In the illustrated embodiment, purified water is gravity fed or pumped from coil outlet 86, through at least one finishing filter 16, 18a/18b to create WFI if needed for its application. In an embodiment, condenser 80 includes a fan 100 (e.g., a cooling or airflow source), which blows air radially outwardly over coil 82 to aid condensation.

FIG. 1 further illustrates that distillation unit 10a may include a control unit 24 having at least one processor and at least one memory. The at least one memory may include one or more instructions, which when executed by the at least one processor, cause the at least one processor to perform the operations discussed herein. Any one or more of heater 30, fan 100, and any one or more water pump (not illustrated in FIG. 1) may be under control of control unit 24. Control unit 24 in an embodiment also includes a video controller and a sound card to output video and audio (text, pictures, videos, alarms, voice guidance, etc.) to a user interface 26. User interface includes one or more input device, such as a touch screen overlay and/or one or more membrane switch to allow the user to enter commands into distillation unit 10a. One or more speaker 28 is provided to output sounds, e.g., alarms or voice guidance to the user.

Figure 2:
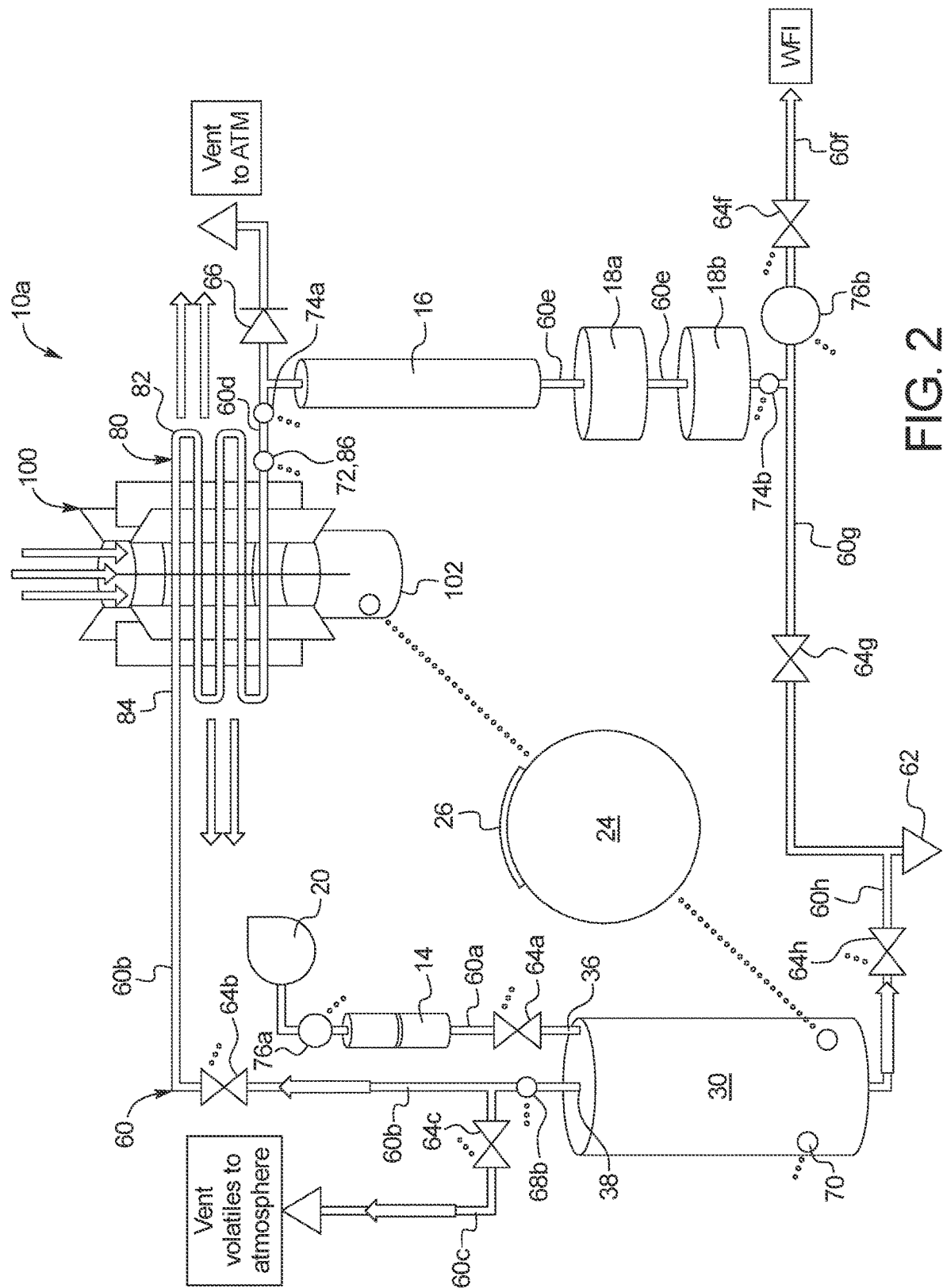
FIG. 2 is a schematic view of a purified water generation unit or distillation unit showing one embodiment of an overall flowpath, sensing, valving, optional pumping and control arrangement of the present disclosure.

FIG. 2 illustrates purified water generation unit or distillation unit 10a schematically and allows additional structure of unit 10a to be shown. Structures of unit 10a discussed in connection with FIG. 1 are numbered the same in FIG. 2, including, predistillation filter 14 (e.g., optional granulated activated carbon ("GAC") filtration for chloramines), polishing filter 16 (e.g., small permanent, semi-permanent or disposable EDI filter or disposable deionization resin), sterilizing filter(s) 18a/18b (e.g., ultrafilters 18a and 18b having membrane pore sizes equal to or less than 0.2 micron), unpurified water tank 20 (optional or alternatively a tap water connection), heater 30 (e.g., a greater than 1.4 kilowatt (kW) heater), condenser 80 (e.g., having coil 82 with coil inlet 84 and coil outlet 86) and fan 100 having fan motor 102. FIG. 2 also illustrates one embodiment for an overall flowpath 60 for distillation unit 10a. Overall flowpath 60 includes an unpurified water line 60a leading from unpurified water tank 20 (or directly from tap source) to a water inlet 36 of heater 30. A steam or vaporized water line 60b extends from a steam outlet 38 of heater 30 to inlet 84 of condensing coil 82. A vent line 60c branches off of vaporized water line 60b (having a vaporized water pressure sensor 68b) and allows volatiles vaporized at heater 30 to be vented to atmosphere via valves 64c and 64b under the control of control unit 24.

A condensed and purified water line 60d extends from outlet 86 of condensing coil 82 to an inlet of polishing filter 16. Sterilizing lines 60e extend from an outlet of polishing filter 16, through sterilizing filter 18a, to sterilizing filter 18b. A WFI line 60f extends from the outlet of sterilizing filter 18b to a use or delivery point for the WFI. If finishing filters 16, 18a/18b are not provided, then condensed and purified water line 60d extends instead to a use or delivery point for the purified water. A bypass line 60g branches off of WFI line 60f (or purified water line 60d) and extends to a drain 62. A residue or collected impurities line 60h extends from heater 30 to drain 62. Impurities or volatiles distilled from the unpurified water at heater may accordingly be removed from distillation unit 10a via vent line 60c, residue or collected impurities line 60h to drain 62, and/or removed along with the disposable heater assembly when discarded. In some embodiments, the impurities line 60h may be fluidly coupled to a first drain and the bypass line 60g may be connected to a second drain to prevent potential contamination of purified water.

In an embodiment, each of lines 60a to 60h is made of a reusable material, such as stainless steel, which is medically safe and sterilizable using high temperature water and/or vaporized water or steam. It may be possible to use polymers or plastics for at least some of lines 60a to 60h, e.g., which are not subject to high heat sterilization or wherein such polymers or plastics are capable of withstanding the disinfection temperatures. While it is desirable for cost reasons for lines 60*a* to 60*h* to be made of a reusable, it may be desirable for connectability reasons to make certain lines disposable, e.g., WFI line 60*f*, which may be part of a disposable set for preparing dialysis fluid using the WFI (or purified water), and which connects to distillation unit 10*a* during treatment setup.

FIG. 2 further illustrates plural valves that operate along various lines of overall flowpath 60. Where lines 60*a* to 60*h* are reusable, the valves may be electrically actuated solenoid valves under control of control unit 24, which are spliced into the reusable lines. Where lines 60*a* to 60*h* are disposable, (i) the valves may be pinch valves placed outside the lines to selectively open and close the lines, or (ii) if the lines are provided as part of a disposable cassette, the valve actuators may be pneumatically or electromechanically actuated to open and close fluid valve portions of the disposable cassette. In FIG. 2, an unpurified water valve 64*a* is located to selectively open and close unpurified water line 60*a*. A vaporized water valve 64*b* is located to selectively open and close a vaporized water line 60*b*. A vent valve 64*c* is located to selectively open and close vent line 60*c*. A WFI valve 64*f* is located to selectively open and close WFI line 60*f* (or purified water line 60*d* if the finishing filters are not provided). A bypass valve 64*g* is located to selectively open and close bypass line 60*g*. An impurities removal valve 64*h* is located to selectively open and close impurities removal line 60*h*. In some embodiments, the valve 64*g* may be omitted such that the bypass line 60*g* is connected to a separate drain. The use of separate drains may prevent cross-contamination of the lines 60*g* and 60*h*.

Valves 64*a* to 64*c* and 64*f* to 64*h* are each illustrated with dotted lines, indicating that they are under automatic control of control unit 24. A relief valve 66 is located in purified water line 60*d*, which is typically not under automatic control, but opens instead to relieve excess pressure in the purified water line, where the excess pressure is vented downstream to atmosphere. As a safety measure, relief valve 66 vents air compressed due to the condensation of water behind the slug of air to protect downstream finishing filters 16, 18*a*/18*b* from seeing potentially damaging pressures.

FIG. 2 further illustrates that a vaporized water pressure sensor 68*b* may be located so as to sense the pressure of vaporized water line 60*b*. The dotted line associated with vaporized water pressure sensor 68*b* indicates that it outputs to control unit 24. The system runs at barely higher than atmospheric pressure throughout under normal operating conditions. Although not illustrated, additional pressure sensor(s) may be located in any desired location along overall flowpath 60 and/or with heater 30. For example, a WFI or purified water outlet pressure sensor may be located along outlet line 60*f* so that the output pressure of distillation unit 10*a* may be monitored. The pressure sensors may be of types that extend into the fluid lines, or that contact the fluid lines or cassette sheeting covering the fluid lines. In one preferred embodiment, each pressure sensor regardless of operational type is configured to output to control unit 24.

In an embodiment, the amount of power provided to heater 30 determines the amount of water produced (e.g., control unit 24 may be programmed to calculate the needed power to produce x amount of water in y amount of time). The speed of fan 100 in the condenser may determine the output water temperature, wherein control unit 24 determines the speed of fan 100 via feedback from a temperature sensor (not illustrated) at outlet 86 of condenser coil 82.

FIG. 2 illustrates that a water level sensor 70 may be located in thermally insulative base 32 of heater 30 to detect how much unpurified water has been introduced via unpurified water valve 64*a* and/or to provide a low level detection for when more unpurified water needs to be filled via water valve 64*a*. To that end, multiple water level sensors 70, e.g., high and low sensors, may be provided. Water level sensor 70 may be configured to output to control unit 24 as indicated by the dotted line. In one embodiment, low level detection via level sensor 70 is outputted to control unit 24 for the electrode driver hardware because the conductivity of the water rises slowly during operation, then drops abruptly as less electrode surface area is covered by the water when the level is low. Level sensor 70 prevents too much electrode surface from being uncovered. Such sensors may be float type switches, capacitive or inductive level sensors. Or, a single water level sensor 70 that is capable of detecting multiple water levels or a range of water levels may be employed. Suitable water level sensors are disclosed in the following patent applications owned by the assignee of the present disclosure: U.S. provisional application No. 62/884,862, filed Aug. 9, 2019 and U.S. provisional application No. 62/830,906, filed Apr. 9, 2019, the contents of each of which are incorporated herein by reference and relied upon.

FIG. 2 also illustrates that a temperature sensor 72 is located in one embodiment so as to sense the temperature of the purified water exiting condenser 80 to ensure that the water is safe to be delivered to the point of use, e.g., a mixing location to be combined with concentrates to form a dialysis fluid. In instances in which WFI or purified water from distillation unit 10*a* is used to make dialysis fluid, the dialysis fluid is often heated before delivery for treatment. In such dialysis fluid cases, it is expressly contemplated to use the output from temperature sensor 72 as feedback to control unit 24 (see dotted lines from sensor 72) for the purpose of controlling the speed of a fan motor 102 of fan 100 (driving a centrifugal blower) to in turn control the amount of cooling air flow that is provided via condensing coil 82, which is performed to produce purified water from condensing coil 82 at a desired temperature above ambient. For example, if the desired temperature of the dialysis fluid is 37° C., temperature sensor 72 may be used as feedback to control the temperature of purified water exiting coil outlet 86 to be, for example, a degree or two below the target temperature (e.g., 35° C.) to minimize energy loss in the condensation stage. In this way, the heater of the dialysis fluid delivery machine (PD, HD, HF or HDF) can be very small, that is, just big enough to nudge and fine tune the temperature from 35° C. to 37° C., for example. Here, energy usage is conserved at both the heater of the dialysis fluid delivery machine. Also, dialysis fluid heating time is reduced such that dialysis fluid preparation time is reduced.

FIG. 2 further illustrates that purified water generation unit or water distillation unit 10*a* may provide multiple conductivity sensors, such as upstream conductivity sensor 74*a* and downstream conductivity sensor 74*b*, which each output to control unit 24 as indicated by their dotted lines. Upstream conductivity sensor 74*a* is placed upstream of finishing filters 16, 18*a*/18*b*, while downstream conductivity sensor 74*b* is located downstream of the finishing filters. If purified water line 60*d* and sterilizing lines 60*e* or WFI line 60*f* are electrically conductive (e.g., stainless steel), then conductivity sensors 74*a* and 74*b* may be attached or otherwise operably engaged with the outside of those lines. If any of the lines with which conductivity sensors 74*a* and 74*b* operate are instead electrically nonconductive, then conductive wells, to which conductivity sensors 74*a* and 74*b* may be attached or otherwise operably engage, may be inserted through the walls of the electrically nonconductive lines to contact the water flowing therethrough. Conductivity sensors 74a and 74b may alternatively be non-invasive, e.g., magnetically operated. In either case, the output of conductivity sensors 74a and 74b is in one embodiment compensated for temperature. If the temperature drop across finishing filters 16, 18a/18b is minimal, then temperature sensor 72 may suffice for both pre- and post-conductivity sensors 74a and 74b. If not, a second temperature sensor may be added to operate with downstream conductivity sensor 74b.

Conductivity sensors 74a and 74b output to control unit 24, which analyzes their outputs to ensure that electrodionization ("EDI") filter 16 is operating properly, and/or that the deionization resin capacity has not been exhausted (or reduced to a level that requires replacement) in various embodiments. If the filter is operating properly, downstream conductivity sensor 74b should read zero or close to zero. Upstream conductivity sensor 74a shows control unit 24 how much conductivity needs to be removed. Moreover, the delta between readings of conductivity sensors 74a and 74b may be used by control unit control unit 24 to detect and/or predict when the deionization resin needs to be replaced. In the case in which finishing filter 16 is not provided, conductivity sensors 74a and 74b may not be needed, however, exit conductivity sensor 74b may still be provided to know the conductivity of purified water exiting distillation unit 10a.

Water generation unit or water distillation unit 10a may not need or provide any pumps. For example, distillation unit 10a may rely upon tap or house water pressure or head pressure within unpurified water tank 20 to drive unpurified water into heater 30. The boiling of the water within heater 30 provides the motive force for moving the steam or vaporized water into and through at least portion of coil 82 of condenser 80. As the steam or vaporized water condenses into purified liquid water, the purified water moves via gravity within and downwardly around the inside of coil 82. As purified water exits outlet 86 of coil 82, a pump provided by a point of use machine, such as a HF machine, HDF machine, chronic or acute CRRT machine, or a medical delivery machine, pulls the purified water from the outlet. In the above example, distillation unit 10a requires no pumps.

It is contemplated however, for distillation unit 10a to provide at least one pump if needed or desired. Each pump is under the control of control unit 24, as illustrated by the dotted lines in FIG. 2. It is contemplated for distillation unit 10a to provide unpurified water pump 76a only, to provide purified water pump 76b only, or to provide both pumps 76a and 76b. Pumps 76a may be gear pumps or other types of electromechanical pumps, e.g., where unpurified water line 60a is non-disposable, e.g., stainless steel lines. Where unpurified water line 60a and/or WFI line 60f are instead made of disposable tubing or as part of a disposable cassette, pumps 76a and 76b may instead be peristaltic pumps or pneumatically or electromechanically actuated, volumetric cassette sheeting pumps. In any case, downstream pump 76b may provide a sterilized interface with the purified water, e.g., peristaltic pumps or pneumatically or electromechanically actuated, volumetric cassette sheeting pumps.

Unpurified water pump 76a may be provided, for example, if it is desired that all or most all of the unpurified water in unpurified water or storage tank 20 be capable of being delivered to heater 30, and wherein the head pressure when the water level reaches the bottom of tank 20 is not enough to force water from the tank, or to do so continuously. It is contemplated that control unit 24 start and stop unpurified water pump 76a based upon the output of water level sensor 70 located within heater 30.

Purified water pump 76b may be provided, for example, if a WFI or purified water accumulator (discussed herein) is placed between distillation unit 10a and the point of use machine, wherein purified water pump 76b delivers WFI or purified water along WFI line 60f to the accumulator. It should be appreciated that pump 76b may be located instead along purified water line 60d, upstream of finishing filters 16, 18a/18b, when, for example, any one or more of the filters requires or operates better under positive water pressure. Also, locating purified water pump 76b along water line 60d, upstream of WFI line 60f and bypass line 60g allows purified water or WGI to be delivered to the point of use or diverted alternatively to drain 62 depending upon the state of valves 64f and 64g.

Figure 3:
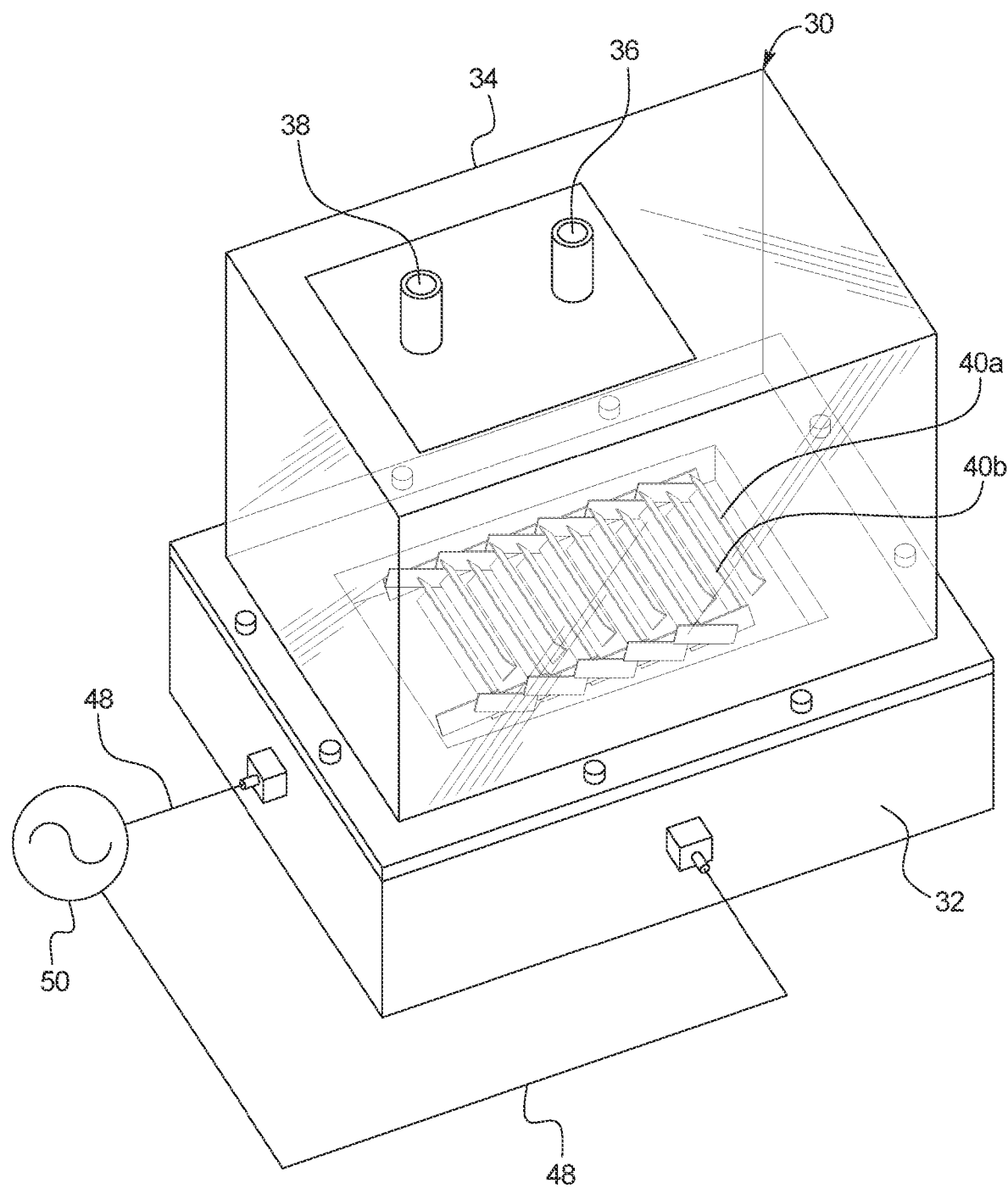
FIG. 3 is a perspective view of one embodiment of a heater of the present disclosure and one possible electrical arrangement for same.
Figure 4A:
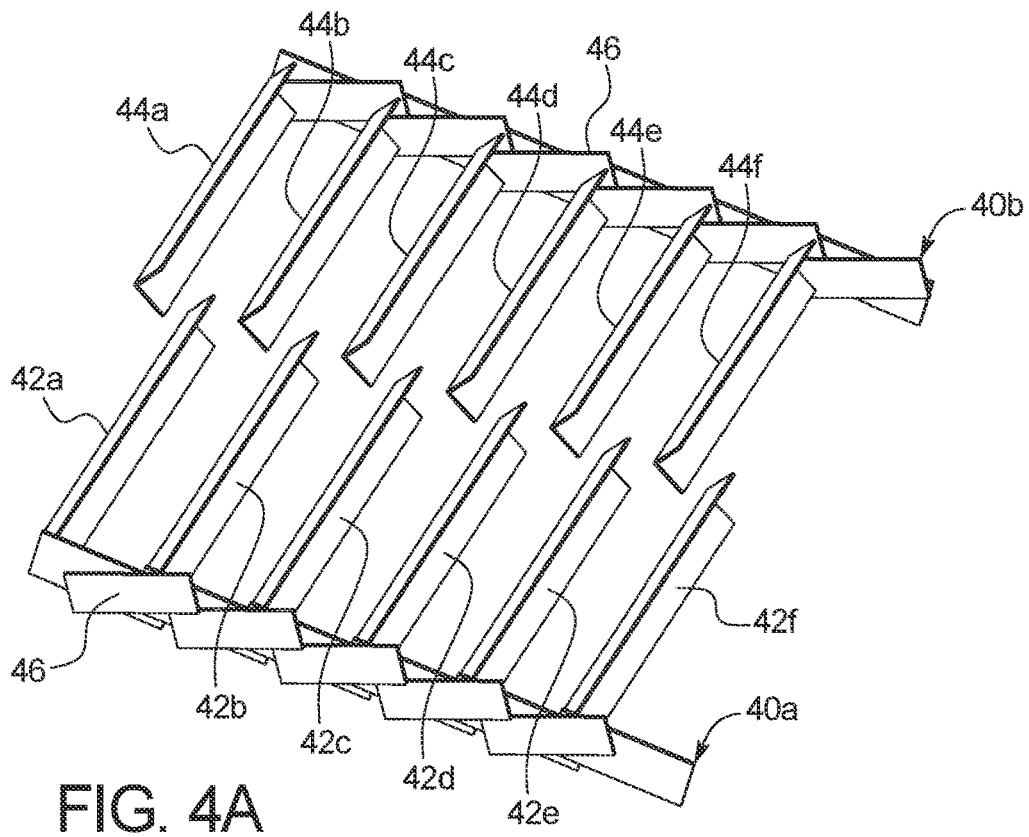
FIGS. 4A and 4B are perspective views of one embodiment of the electrodes used with the heater of the distillation unit in non-interleaved and interleaved juxtapositions, respectively.
Figure 4B:
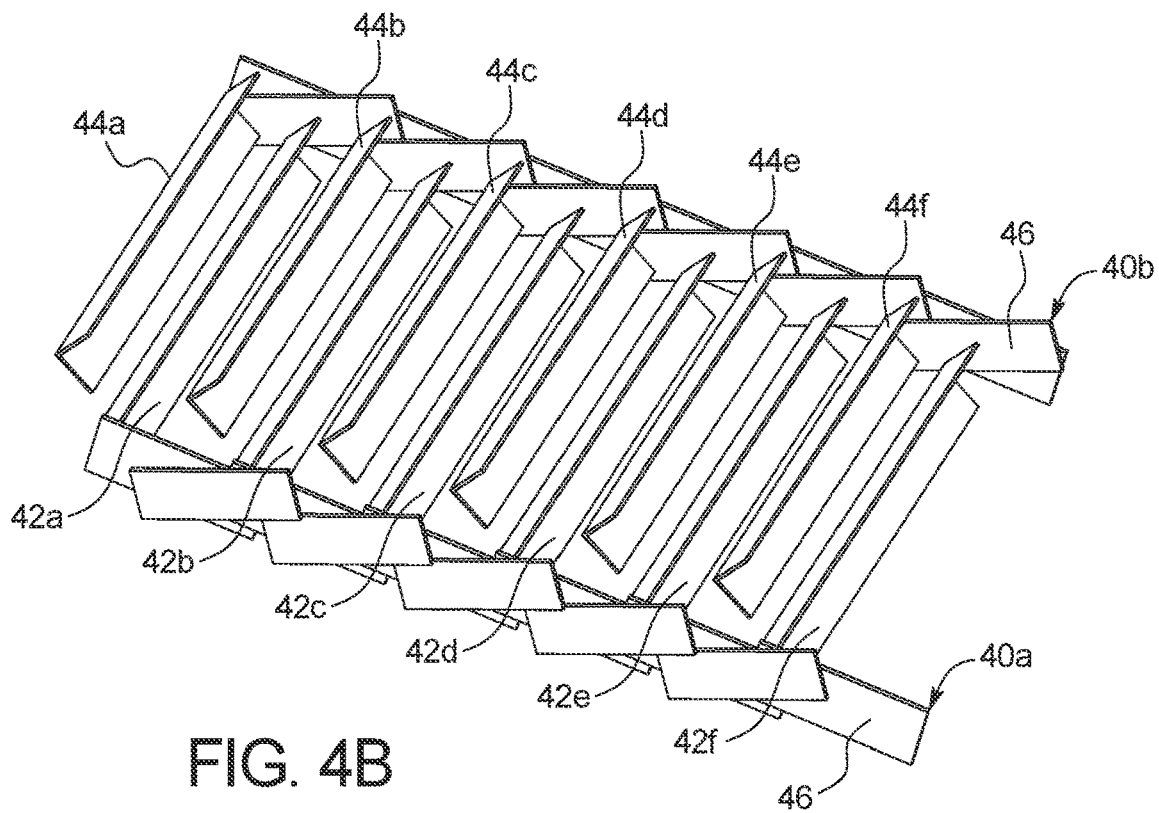
Figure 5:
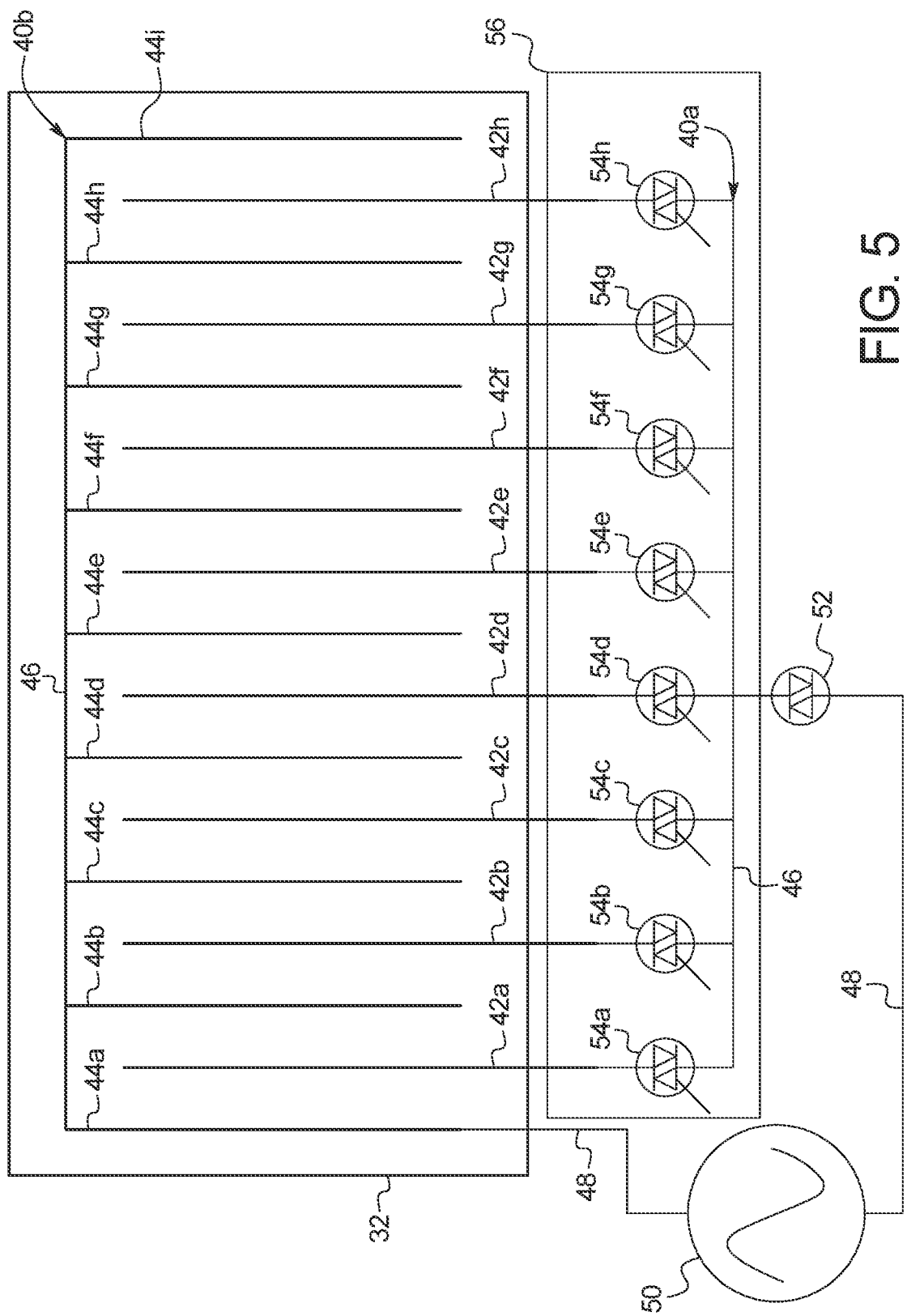
FIG. 5 is a schematic view of another embodiment of a possible electrical arrangement for the heater.

Referring now to FIGS. 3 to 5, heater or boiler 30 is illustrated in more detail. As discussed in connection with FIG. 1, FIG. 3 illustrates again that thermally insulated heater 30 may be provided with a thermally insulative base 32 having a disposable and removable assembly that accepts tap or other unfiltered water, e.g., from predistillation filter 14. Heater 30 also includes a cover 34, e.g., an electrically and thermally insulative cover, which may be removeably, e.g., hingedly, connected to base 32. Thermally insulative base 32 may be made of an insulative plastic, such as, high density polyethylene ("HDPE"), which may be thickened, e.g., 0.5 inch (12.7 mm). The disposable and removable assembly may be thermoformed as a form-fitting polyethylene terephthalate ("PETC") pan or tray 33, which may be thinner, e.g., less than 0.5 inch (12.7 mm) and perhaps even as thin as 0.012 inch (0.3 mm). Disposable and removable pan or tray 33 assembly fits removeably into base 32. As discussed above, electrodes 40a and 40b (e.g., first and second electrodes) may or may not be removed along with pan or tray 33. Insulative cover 34 may be made of the same material as thermally insulative base 32 or of a clear plastic, such as, polyacrylate (acrylic) if it is desirable to see inside of insulative cover 34. The length and width of insulative base 32 and cover 34 may be, for example, 6.3 inch (16 cm)×3.4 inch (10 cm).

FIGS. 3, 4A, 4B and 5 each illustrate that heater 30 includes a pair of electrodes 40a and 40b, which are separated from each other such that current generated at the electrodes has to pass through unpurified water residing between the electrodes to complete an electrical circuit. Electrodes 40a and 40b may be made of a medically compatible and at least somewhat electrically conductive material, such as stainless steel (e.g., 316 or 321) or titanium. Electrode 40a in the illustrated embodiment includes baffles 42a to 42n (e.g., first baffles), which are interleaved within baffles 44a to 44n (e.g., second baffles) of electrode 40b, so as to increase the overall surface area of adjacently juxtaposed electrode material. The increased surface area increases the speed and efficiency at which heater 30 boils the tap or unpurified water by decreasing the resistance between electrodes 40a and 40b, so that the applied voltage produces a high enough current, resulting in the target amount of power to be applied to the water. The amount of electrode surface area is part of a balance along with water conductivity, applied voltage and duty cycle.

Baffles 42a to 42n and 44a to 44n may be thin, e.g., 0.002 inch (0.05 mm) thick, and be folded for rigidity. Baffles 42a to 42n and 44a to 44n may be welded, soldered, sputtered and/or mechanically fixed to manifold portions 46 of their respective electrodes 40a or 40b. The total surface area of electrodes 40a and 40b, including baffles 42a to 42n and baffles 44a to 44n, respectively, may be about 11.6 inches$^2$ (75 cm$^2$).

FIGS. 3 and 5 illustrate that electrodes 40a or 40b are placed within thermally insulative base 32, where the electrodes are fixed in their interleaved, non-contacting relationship. Clips or other connecting structures (not illustrated) may be imbedded within or fixed to the bottom or sides of base 32, which removeably grab ahold of electrodes 40a or 40b to hold them and their baffles apart even if base 32 is tipped or moved. The clips are configured to allow electrodes 40a and 40b to be easily removed from the clips or other connecting structures of base 32 when electrode replacement is needed.

FIG. 3 illustrates that in one embodiment, electrical leads 48 (only one side viewable in FIG. 3) are inserted sealingly through a wall of base 32. Electrical leads 48 extend into the interior of base 32 and are placed into electrical communication with electrodes 40a and 40b. In an embodiment, leads 48 residing within base 32 are fixed and form at least a portion of the clips or other connecting structures that removeably grab ahold of electrodes 40a or 40b. In this manner, when a new set of electrodes 40a or 40b is loaded into base 32, the electrodes are also placed into electrical connection with electrical leads 48 for operation.

Electrical leads 48 are connected to a power or voltage source 50, which for example is configured to apply 1000 to 2000 Watts of power (e.g., at 120 VAC, RMS 15A) to electrical leads 48 and thus to electrodes 40a or 40b and the tap or unpurified water located between the electrodes. FIG. 3 illustrates that the electrical circuit in one embodiment is relatively simple. Power or voltage source 50 supplies electrical power to leads 48, each of which extends into the interior of base 32 and connects to or is otherwise communicated electrically with an electrode 40a or 40b, wherein electrodes 40a or 40b are held physically separate from one another, such that the only way to complete an electrical circuit is through the electively resistive water, which generates heat to boil the unpurified water.

FIG. 5 illustrates a more advanced alternative electrical circuit. Here, one of the leads 48 extending from voltage source 50 extends as in FIG. 3 through a wall of base 32 to connect to or otherwise communicate electrically with electrode 40b. The other lead 48 however extends from voltage source 50 to a phase control triode for alternating current ("TRIAC") 52, which is electrically communicated with surface area modulation TRIACs 54a to 54h, one each dedicated to each baffle 42a to 42h of electrode 40a. In the illustrated embodiment, manifold portion 46 of respective electrode 40a, phase control TRIAC 52 and surface area modulation TRIACs 54a to 54h are provided on a printed circuit board 56, which may be provided with base 32 or located in an electrical area of housing 12 of distillation unit 10a. In the illustrated embodiment, TRIACs 54a to 54h apply power to a subset of the electrodes if the conductivity of water is too high. Alternatively, TRIAC 52 can be phase controlled (a form of pulse width modulation) to control the amount of power applied to the water. In one embodiment, TRIAC 52 is used alone, or perhaps two or three of TRIACs 54a to 54h to handle very conductive water, either in connection with TRIAC 52 or phase controlled directly under control of control unit 24.

While electrical leads 48 are illustrated as being exposed in FIGS. 3 and 5 for ease of illustration, it is contemplated in a commercial embodiment to runs leads 48 within or under base to a power/electrical station within housing 12 of distillation unit 10a or to a plug or other bulkhead electrical connector located within a side of base 32. In either case, it is likely that power or voltage source 50 is located with the power/electrical station of distillation unit 10a.

As illustrated by the electrical circuit of FIG. 3 or FIG. 5 (schematic and implementations illustrated), heater 30 boils the unpurified or tap water as a first step in the distillation process. Distillation separates components or substances, in the present case volatiles, from a liquid, in one example unpurified or tap water, using selective boiling and condensation. The volatiles of the present distillation process are either collected at the bottom of base 32 of heater 30 and discharged intermittently from the heater to drain 62 via impurities removal valve 64h and/or are vented through a vent in vent line 60c extending in fluid communication with outlet port 38 of heater 30.

Cover 34 as discussed above is removeably, e.g., hingedly, connected to base 32, such that the cover allows access to electrodes 40a and 40b for adjustment, maintenance and replacement. FIG. 3 illustrates that cover 34 provides two ports, namely, port 36 for connection to an unpurified water source (tank 20 or tap water directly), and port 38 for connection to a steam line, which carries steam from heater 30 to condenser 80.

Figure 6B:
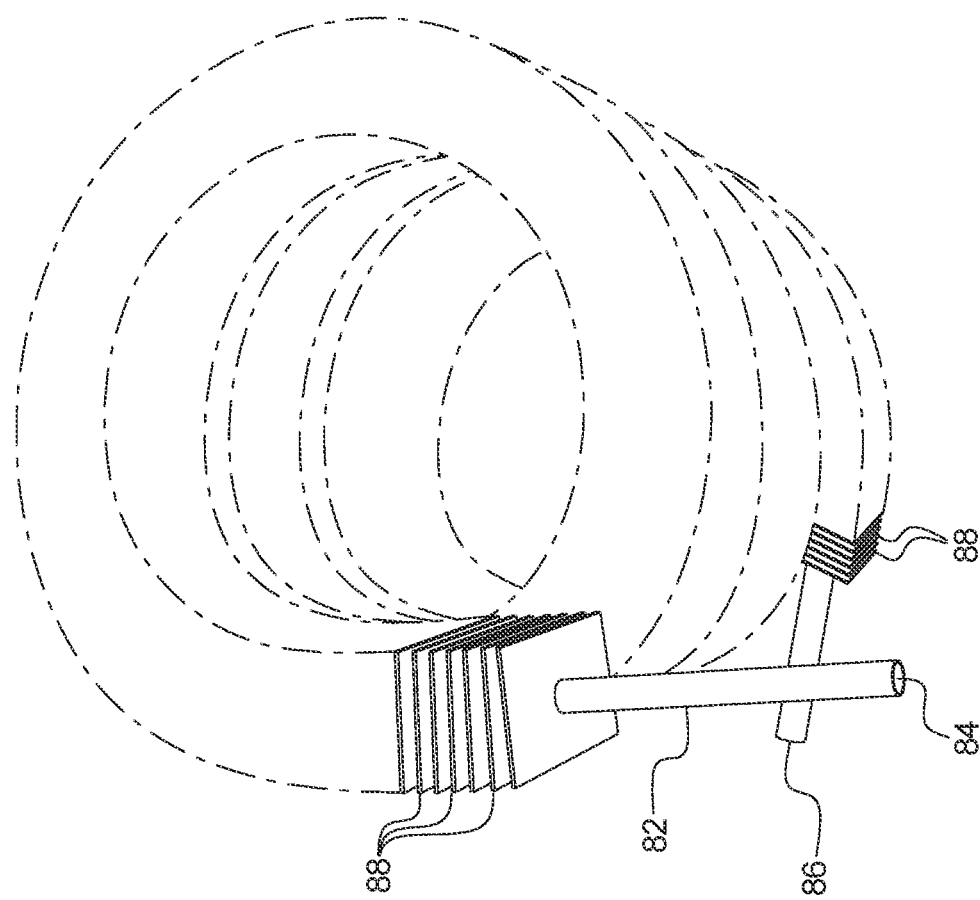
FIGS. 6A and 6B are perspective views of one embodiment for the condensing coil of the condenser of the distillation unit of the present disclosure.
Figure 6A:
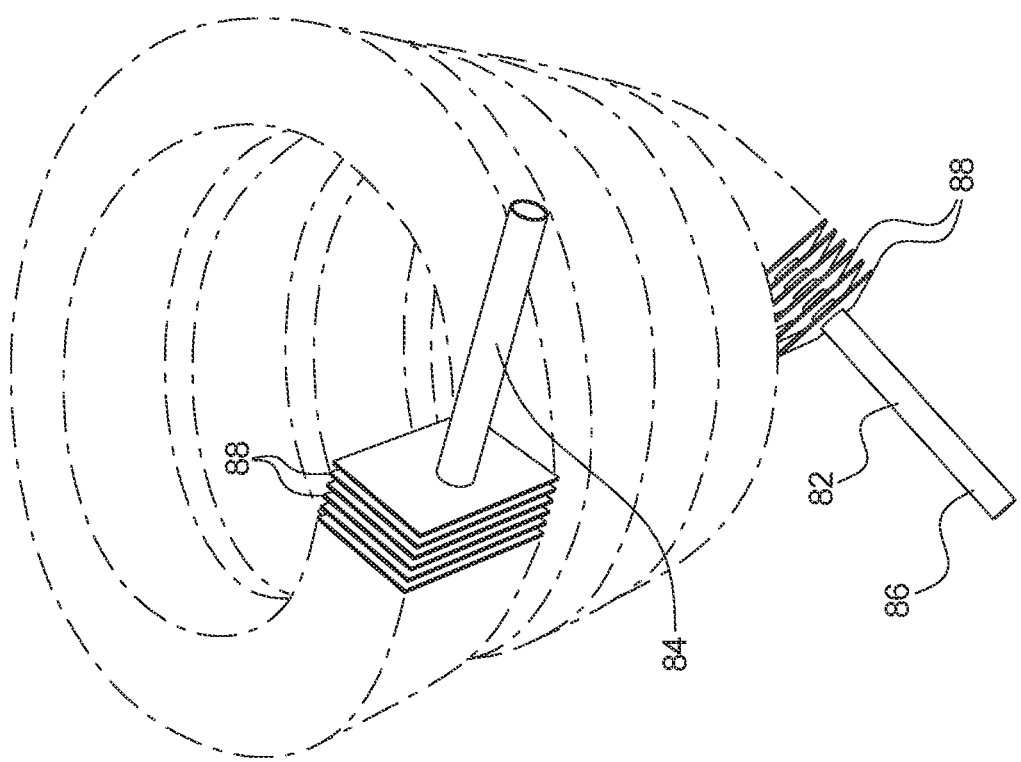

FIGS. 6A and 6B illustrate that condenser 80 includes a condensing coil 82 having an inlet 84 and an outlet 86, which may be made of a thermally conductive and medically safe material, such as stainless steel (e.g., 304 or 316) or titanium. In various embodiments, coil 82 is made of 0.25 inch (6.3 mm), 0.375 inch (9.5 mm) or 0.5 inch (12.7 mm) diameter 304 stainless steel tube, e.g., twenty mils thick, which is coiled, e.g., with five full turns at four inches (10 cm) to ten inches (25.4 cm) nominal diameter.

Plural heat fins 88, such as highly thermally conductive copper heat fins, are attached to the coil, e.g., via soldering, welding, brazing, gluing (a potentially useful method to reduce high temperatures at time of manufacture that might lead to contamination of the tubing) and/or mechanical connection. Heat fins 88 may each be one inch (2.54 cm) by 1 inch (2.54 cm) square copper 110 alloy (99.9% copper, annealed) at 21 mils thick. Heat fins 88 may each be bent and/or roughened as desired to increase heat transfer. Heat fins 88 conduct heat away from coil 82 and the steam located within the coil. Coil 82 as illustrated includes an inlet 84 and an outlet 86, wherein the inlet is located at the top of coil 82, while the outlet is located at the bottom of coil 82. In this manner, steam from heater 30 enters inlet 84 at the top of coil 82, while highly purified water exits the outlet 86 at the bottom of coil 82.

Figure 7A:
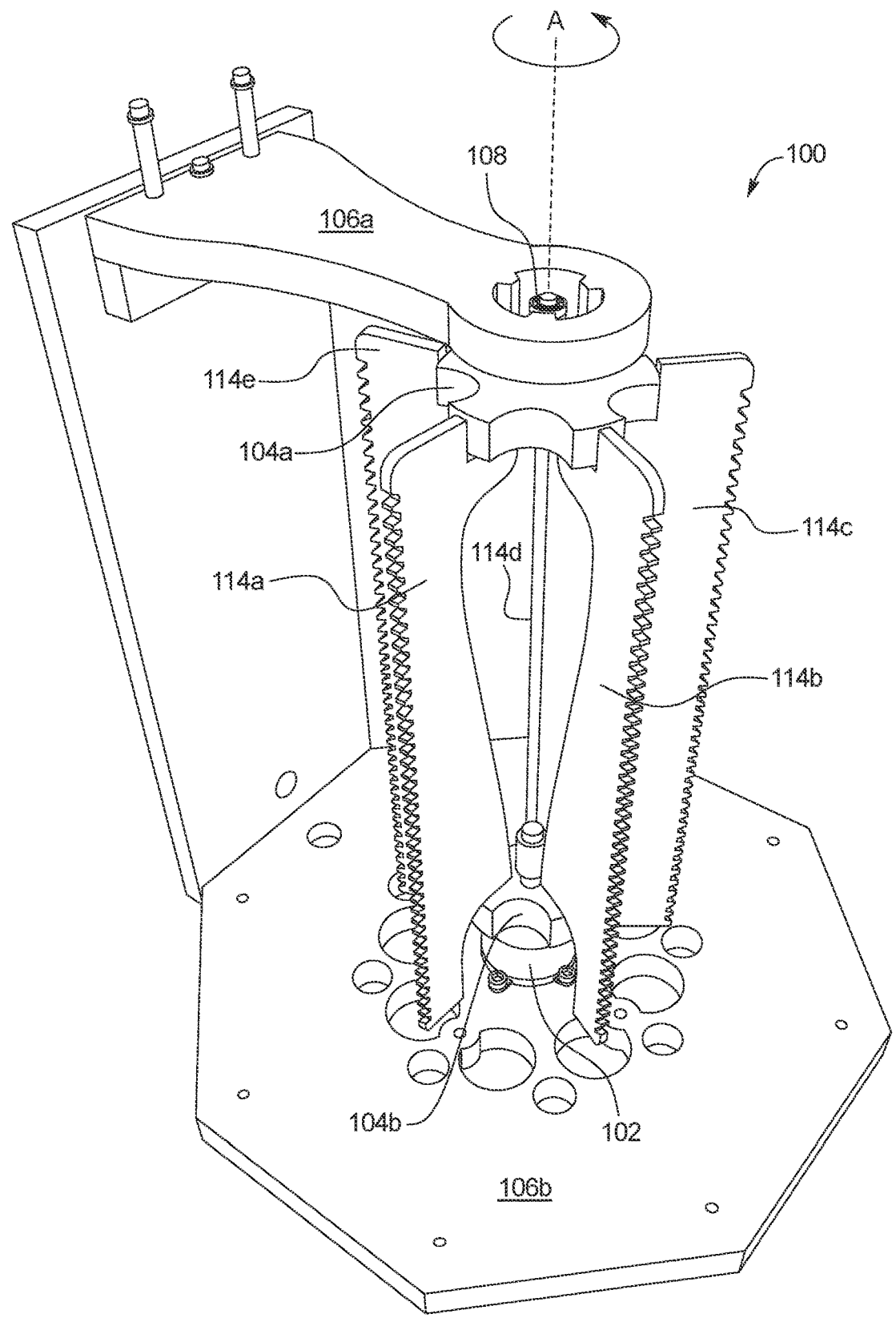
FIGS. 7A to 7C are perspective views of one embodiment for a fan of the condenser, including various components of the fan.
Figure 7B:
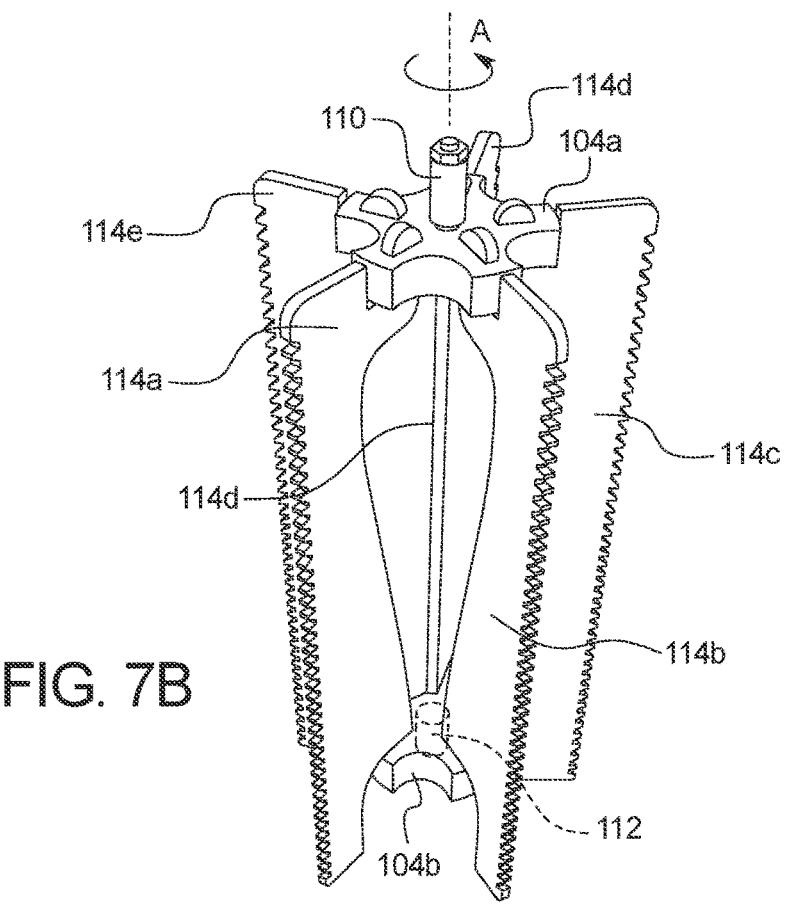
Figure 7C:
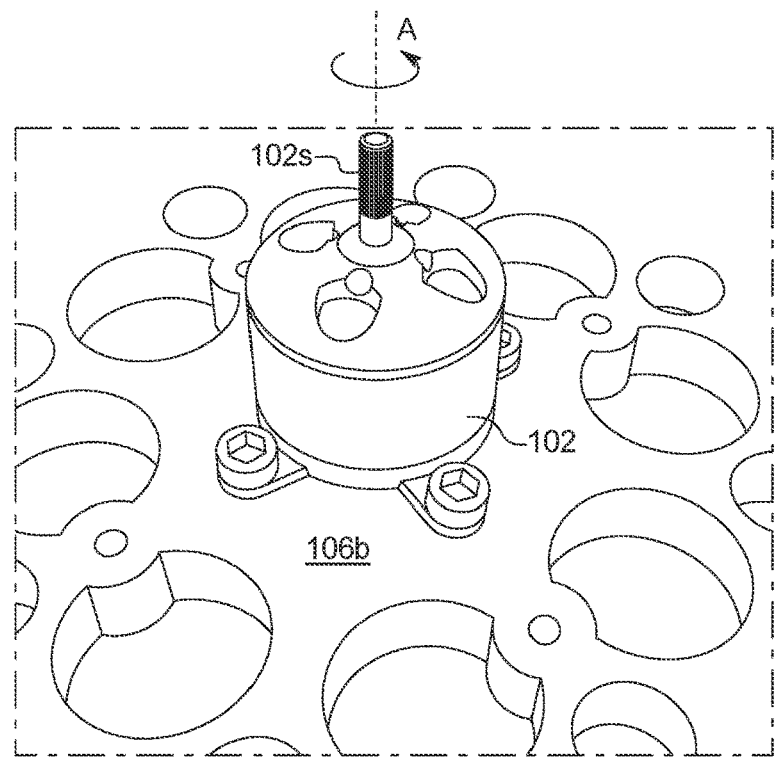

FIGS. 7A to 7C illustrate one embodiment for condenser fan 100, which is located inside of coil 82 and associated heat fins 88 to form condenser 80. Fan 100 in the illustrated embodiment includes upper and lower fan blade holders 104a and 104b that are attached respectively to upper and lower fixtures 106a and 106b via ball or roller bearings 108 and pump 102. Upper fan blade holder 104a incudes or is attached to a shaft 110 (FIG. 7B) that fits inside of upper roller bearing 108 (FIG. 7A). Lower fan blade holder 104b defines an elongated aperture 112 that accepts a shaft 102s of fan motor 102. The output shaft of fan motor 102 is coupled via a direct coupling (e.g., set screw), or via a geared or belt and pulley relationship as desired, to lower fan blade holder 104b.

Fan motor 102 in an embodiment is a three phase brushless motor, 150 W. Distillation unit 10a may be equipped with a variable speed motor drive may, which is commanded by control unit 24 to cause fan motor 102 to spin at a speed known to achieve a desired outlet temperature of WFI or ultrapure water, where the desired temperature is inputted into user interface 26 by a user or which is sent to distillation unit 10a via the point of use machine wired or wirelessly.

Fan motor 102 is alternatively a single speed motor. Fan motor 102 may be unidirectional or rotate in two directions.

FIGS. 7A and 7B illustrate that upper and lower fan blade holders 104a and 104b spin around a vertical axis of rotation A extending through the centers of ball or roller bearings 108 and pump 102. Blades 114a to 114e of fan 100 are in an embodiment vertically disposed paddles or baffles that are formed with (e.g., single molded piece with one or both blade holders 104a and 104b) or are connected to upper and lower fan blade holders 104a and 104b, so as to extend radially from the vertical axis of rotation A. Blades 114a to 114e and holders 104a and 104b, may be made of metal or plastic, for example. Blades 114a to 114e may be substantially straight as illustrated or be curved to affect air flow in a desired manner.

FIG. 7A illustrates that upper ball or roller bearings 108 are placed in a rotationally fixed relationship within upper fixture 106a. FIG. 7C illustrates that fan motor 102 is bolted to lower fixture 106b. The engagements to upper and lower fixtures 106a and 106b hold fan blades 114a to 114e firmly in place but allow the blades to spin freely about the vertical axis of rotation A. In an alternative embodiment, fan blades 114a to 114e may be held fixed instead to a vertical shaft (not illustrated) that extends along and spins around the length of vertical axis of rotation A due to a coupling with fan motor 102.

Figure 8:
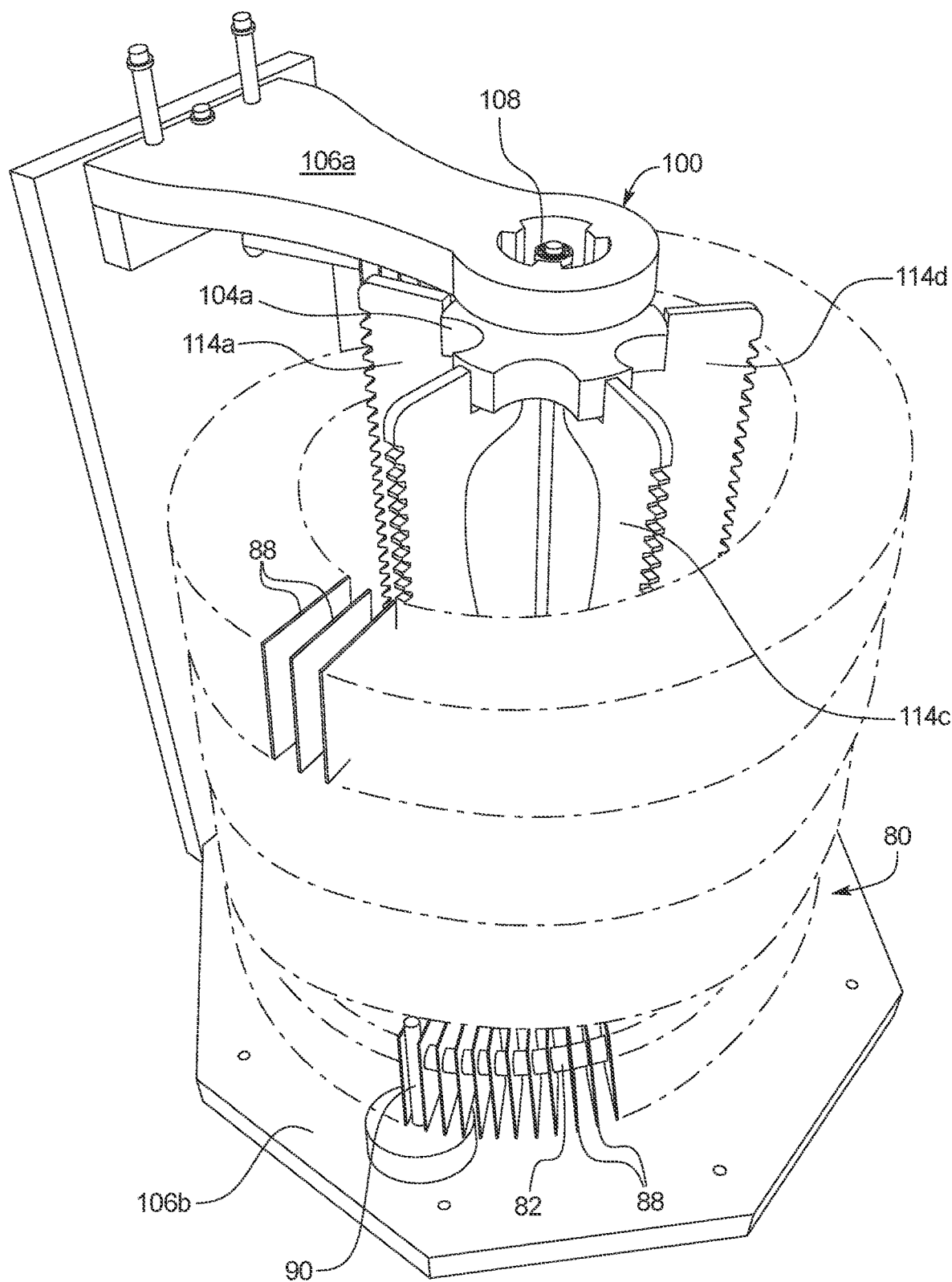
FIG. 8 is a perspective view of one embodiment for the fan interacting with the condensing coil of the distillation unit of the present disclosure.

FIG. 8 illustrates condenser 80 fully assembled with fan 100 located within coil 82 and heat fins 88. FIG. 8 illustrates that coil may be fixed to lower fixture 106b via one or more mount 90. Mounts 90 may be bolted to or formed with lower fixture 106b and include structure(s) that grasps one or more turn of coil 82. Multiple mounts 90 hold coil 82 and heat fins 88 firmly in place from the bottom of the coil. Fan motor 102, under control of the control unit 24, causes fan blade holders 104a and 104b and fan blades 114a to 114e to spin. The spinning of fan blades 114a to 114e drives air radially outwardly over copper heat fins 88 and condenser coil 82, forming a centrifugal blower that causes convective heat transfer from the steam or vaporized water traveling through condenser coil 82.

As mentioned above, in an embodiment control unit 24 of water purification or distillation unit 10a is configured to receive (e.g., from the master control unit of the PD, blood or other point of use machine) a desired purified water or WFI temperature exiting coil outlet 86. Control unit 24 may in turn access a look-up table that correlates purified water or WFI exit temperature with the speed of fan motor 102. Control unit 24 then sets the fan speed via a variable motor drive to be the correlated fan speed for the desired water exit temperature. Providing water at a temperature elevated above ambient is advantageous for PD or blood treatment applications, which may require the resulting mixed dialysis fluid to be at or near body temperature, e.g., 37° C. Here, heating energy required at the PD or blood treatment machine is conserved, energy to drive fan 102 is conserved, and the time necessary for the resulting dialysis fluid to be suitable for treatment is lessened. It may be found however that elevated water temperatures place undue stress on finishing filters 16, 18a/18b. In such a case, for example, a single speed fan motor 102 and associated motor drive may be employed, wherein the fan speed is selected to bring the temperature of the purified water at coil outlet 86 to as close to ambient as possible.

Alternative Distillation Units

Figure 9:
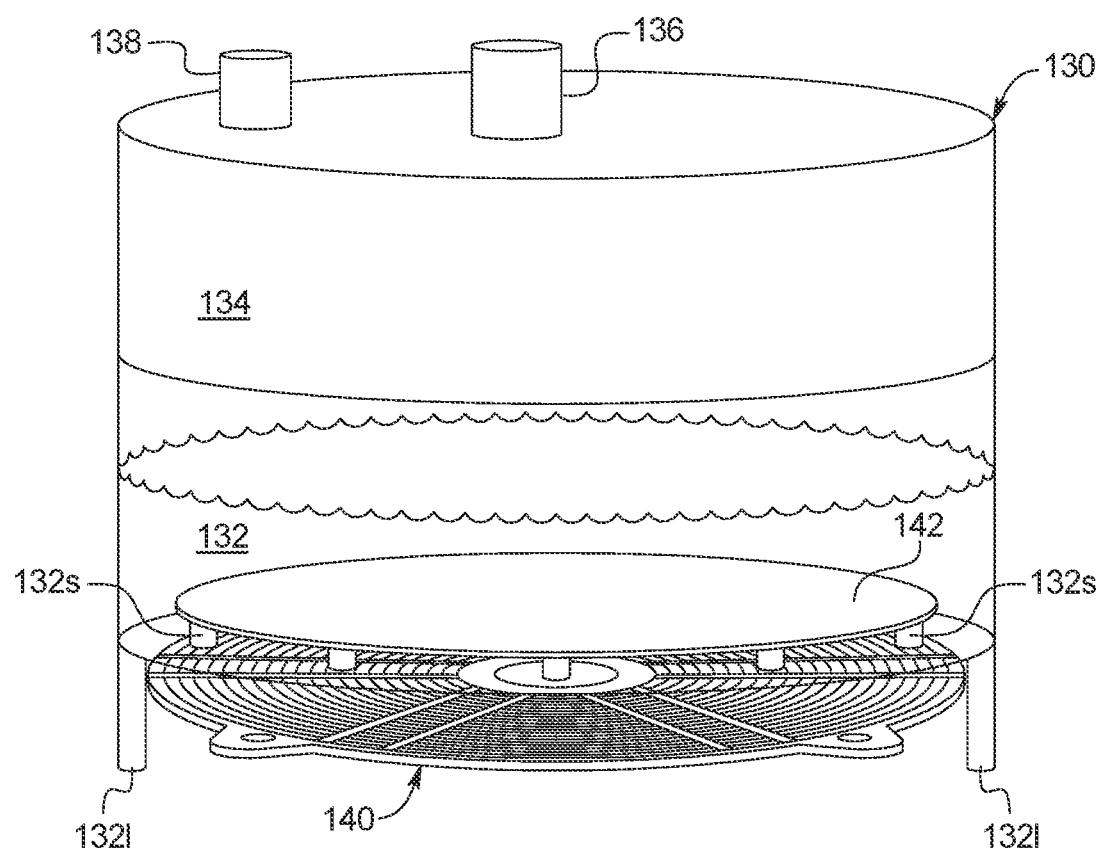
FIG. 9 is a front elevation view of an alternative heater of the present disclosure.

FIG. 9 illustrates an alternative heater 130, which may be used instead with distillation unit 10a or any of the other distillation units discussed herein. Alternative heater 130 includes a vessel, which may include a vessel base 132 and a vessel cover 134, which is removeably, e.g., hingedly, attached to vessel base 132, so that the inner surfaces and contents within the vessel may be cleaned, accessed and/or replaced. Vessel cover 134 in the illustrated embodiment includes an unpurified or tap water inlet port 136 and a steam or vaporized water outlet port 138. Water inlet port 136 may be placed in fluid communication with a source of tap water or with unpurified water storage tank 20. Vaporized water outlet port 138 may output to condenser inlet 84.

In the illustrated embodiment of FIG. 9, a direct induction boiler 140 is located beneath or otherwise adjacent to vessel base 132. Vessel base 132 may form or be attached to with legs 132l to hold the base above direct induction boiler 140 and standoffs 132s to hold a stainless steel (e.g., 316 stainless) or otherwise electrically conductive and medically safe plate 142 above the bottom of base 132. Standoffs 132s are non-conductive in one embodiment. Conductive and medically safe plate 142 may for example be six inches (15.24 cm) in diameter, twenty mils thick, and disposable.

Alternative heater 130 boils water via magnetic induction. Direct induction boiler 140 may be a commercially available Litz wire induction coil. Induction boiler 140, under control of control unit 24, creates a high frequency magnetic flux that induces eddy currents in conductive and medically safe plate 142, which along with hysteresis losses causes the unpurified water in contact with the plate to boil. Hysteresis losses in the plate may be a greater contributor to heating than eddy currents. Plate 142 may be any one or more of roughened, bent, cut, etc., to increase heat transfer efficiency.

Figure 10:
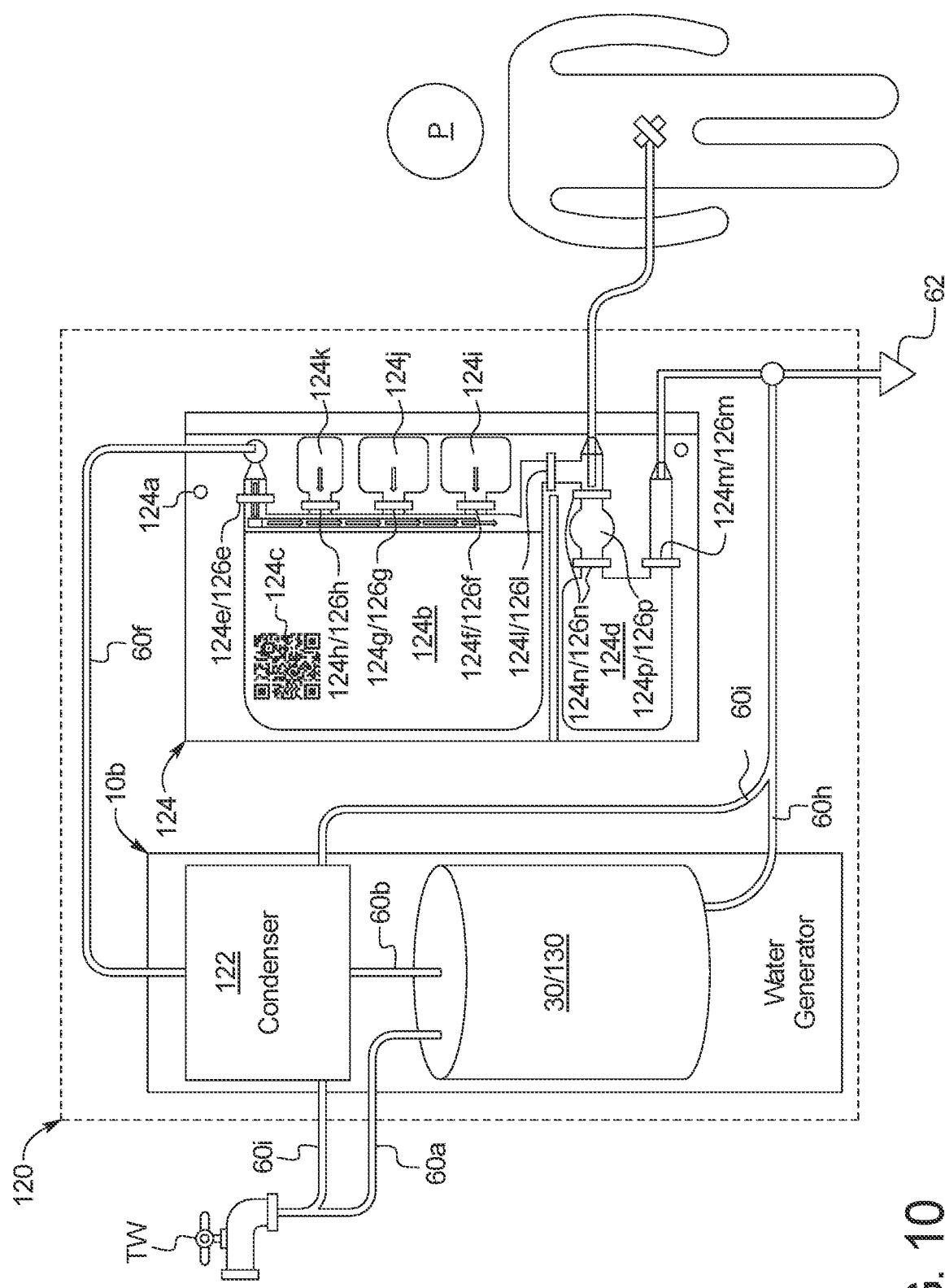
FIG. 10 is a schematic view of one alternative purified water generation or distillation unit of the present disclosure operating in an overall peritoneal dialysis system.

FIG. 10 illustrates a system 120, which includes an alternative purified water generation unit or distillation unit 10b. Alternative distillation unit 10b uses either heater 30 or 130 discussed above. The primary difference between distillation unit 10b and distillation unit 10a is that distillation unit 10b uses tap water to cool the boiled water instead of condenser 80 discussed above. FIG. 10 illustrates two lines extending from tap water source TW, namely, unpurified water line 60a discussed above in connection with FIG. 2 and a cooling line 60i, which extends from tap water source TW to condenser 122. Condenser 122 may include a serpentine pathway (not illustrated) within which the steam travels and condenses into purified water as the cooling water flows over the multiple turns and runs of the serpentine pathway. Heat fins may or may not be provided with the serpentine pathway. Condenser 122 may also double as storage tank 20.

Condensed and purified water flows from condenser 122 to a disposable set 124 operated by a point of use machine, here a PD machine. It should be appreciated that distillation unit 10b is illustrated in a simplified manner in FIG. 10 and may include any or all of the other features, structures and alternatives discussed in connection with FIG. 2 for distillation unit 10a, such as, storage tank 20, any of the vent lines and vents illustrated in connection with FIG. 2, any of valves 64a to 64c, and 64f to 64h, water pressure sensor 68b, upstream and downstream conductivity sensors 74a and 74b, finishing filters 16, 18a/18b, pumps 76a and 76b, control unit 24 and user interface 26 for controlling distillation unit 10b.

Disposable set 124 in the illustrated embodiment includes a registration hole 124a for aligning set 124 operably with the point of use machine. Disposable set 124 receives the purified water or WFI from distillation unit 10b (or any other distillation unit described herein) and stores the water in an accumulator chamber 124b. A marking 124c, such as a 2D barcode, may be placed on the disposable set 124 so that it may be read and verified by the point of use machine prior to beginning treatment. Marking 124c may also provide information to the point of use machine, such as prescribed mixing ratios, fresh dialysis fluid delivery and drain amount. A drain chamber 124d is provided adjacent to accumulator chamber 124b. Accumulator chamber 124b stores WFI, mixes the WFI with concentrates to form fresh dialysis fluid, and contacts a heater (not illustrated) of the point of use machine to allow the fresh dialysis to be heated to a desired temperature for treatment. Drain chamber 124d accepts used dialysis fluid from Patient P and allows the used dialysis fluid to be delivered to drain 62.

Plural valve actuation areas of disposable set 124, each operable with a valve actuator of the point of use machine are provided including: WFI inlet valve actuation area 124e/WFI inlet valve actuator 126e, dextrose inlet valve actuation area 124f/dextrose inlet valve actuator 126f, electrolyte inlet valve actuation area 124g/electrolyte inlet valve actuator 126g, final fill concentrate inlet valve actuation area 124h/final fill concentrate inlet valve actuator 126h, patient fill inlet valve actuation area 124l/patient fill inlet valve actuator 126l, drain outlet valve actuation area 124m/drain outlet valve actuator area 126m, and pump inlet and outlet valve actuation areas 124p/pump inlet and outlet valve actuators 126p. The valve actuators may be pinch valve actuators (e.g., electrically operated solenoid valve actuators), pneumatic valve actuators, spring-located valve actuators and combinations thereof.

Dextrose inlet valve actuation area 124f/dextrose inlet valve actuator 126f selectively allow dextrose to be introduced into accumulator chamber 124b via dextrose source 124i. Electrolyte inlet valve actuation area 124g/electrolyte inlet valve actuator 126g selectively allow electrolyte to be introduced into accumulator chamber 124b via electrolyte source 124j. Final fill concentrate inlet valve actuation area 124h/final fill concentrate inlet valve actuator 126h selectively allow final fill concentrate to be introduced into accumulator chamber 124b via final fill concentrate source 124k.

Pump actuation area 124p is operated upon by a pump actuator 126p. Pump actuator 126p may be a volumetric pump actuator, e.g., a spring-actuated pump actuator, an electromechanically driven pump actuator, a shuttle pump actuator, a pneumatic pump actuator, and combinations thereof. In one embodiment, pump actuator 126p is used to generate negative pressure at pump actuation area 124p, for example to affect drain flow from patient P to drain chamber 124d. Here, patient fill valve 124l/126l is closed, while pump valves 124n/126n are sequenced with pump actuator 126p (e.g., spring-actuated) to pull used dialysis fluid from patient P into drain chamber 124d. To fill patient P, positive pressure is applied to accumulator chamber 124b to pump fresh dialysis fluid from accumulator bag 124b to patient P. Here, pump valves 124n/126n are closed, while patient fill valve 124l/126l is open.

In an alternative embodiment, to pump fresh dialysis fluid to Patient P, pump valve 124n/126n closer to drain chamber 124d is closed, while pump valve 124n/126n closer to Patient P and patient fill valve 124l/126l are open during a draw stroke to pull fresh dialysis fluid into pump chamber or actuation area 124p. Pump valve 124n/126n closer to drain chamber 124 remains closed, while pump valve 124n/126n closer to Patient P remains open, and patient fill valve 124l/126l is closed on a pump-out stroke to push fresh dialysis fluid towards Patient P. To pump used dialysis fluid to drain 62, patient fill valve 124l/126l is closed during both draw and pump-out strokes, drain outlet valve 124m/126m is opened during both draw and pump-out strokes, while (i) pump valve 124n/126n closer to Patient P is open and pump valve 124n/126n closer to drain chamber 124d is closed during a draw stroke to remove effluent from Patient P into pump chamber or actuation area 124p, and (ii) pump valve 124n/126n closer to Patient P is closed and pump valve 124n/126n closer to drain chamber 124d is opened during a pump-out stroke to remove effluent from pump chamber or actuation area 124p towards drain 62. In a further alternative embodiment, drain outlet valve 124m/126m is closed during patient drain to allow effluent to be drained into drain chamber 124d to be weighed (e.g., for ultrafiltration determination) and/or sampled. Afterwards, drain outlet valve 124m/126m may be opened to allow effluent to be gravity fed to drain 62.

It should be appreciated that all of the above valve and pump actuations, heating, weighing, etc., are performed under the control of a control unit (not illustrated but including one or more processor and one or more memory, video card, sound card, etc.) provided with the point of use machine. As discussed in more detail below, the control unit of the point of use machine commands control unit 24 of water generation unit or distillation unit 10b as to demand, e.g., when and how much WFI (or purified water) should be delivered to the point of use machine. Control unit 24 of water generation unit or distillation unit 10b may also communicate back to the control unit of the point of use machine information regarding capacity, e.g., how much can the distillation unit prepare in what time frame, or where the distillation unit is in a current batch cycle.

Figure 11:
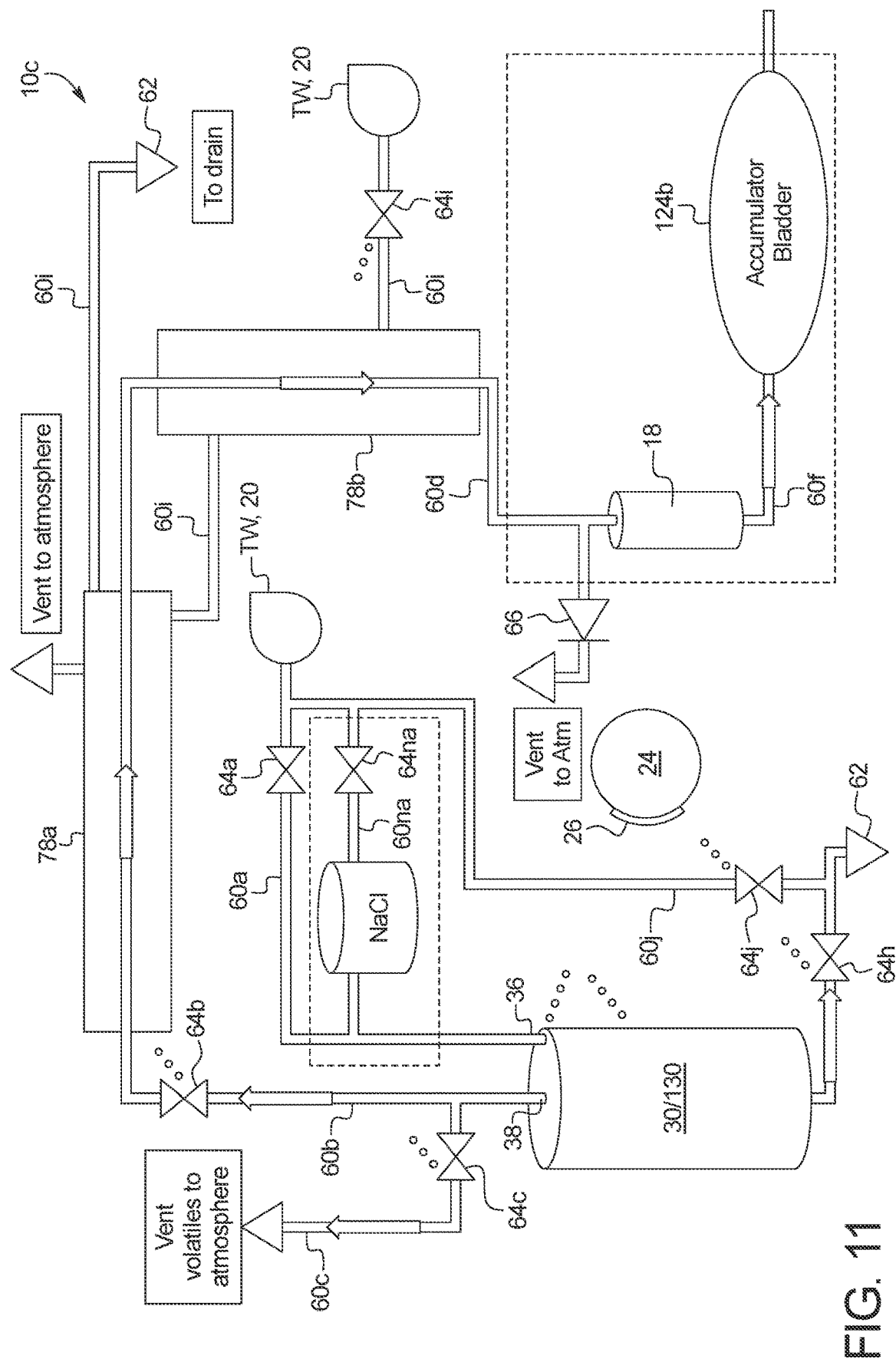
FIG. 11 is a schematic view of another alternative purified water generation or distillation unit of the present disclosure.

Referring now to FIG. 11, another alternative water generation unit or distillation unit 10c is illustrated. Distillation unit 10c, like distillation unit 10b, uses water cooled condensing as opposed to condenser 80 of distillation unit 10a. Distillation unit 10c uses many of the same components, such as heater or boiler 30/130 discussed above as well as many of the same lines and valves as discussed in connection with FIG. 2. Those components are numbered the same in FIG. 11, and all disclosure concerning those components, including any alternative structure and functionality described for same, is applicable to and associated with distillation unit 10c.

One primary difference with distillation unit 10c is that an optional sodium chloride line 60na, valve 64na and NaCl injector are provided in parallel with unpurified water line 60a (operated by unpurified water valve 64a) leading from unpurified tap water TW or water tank 20. NaCl injector may be used with heater 30/130 (and also distillation units 10a and 10b) to ionize the water to be boiled so that electricity is better conducted between electrodes 40a and 40b. Control unit 24 may be programmed to sequence valves 64a and 64na, so that a desired amount of NaCl is dissolved into the water to be boiled. The NaCl injector may include solid salt, salt pellets, crystallized salt, and/or liquid salt concentrate, which is mixed with tap water from tap water source TW or storage tank 20. The tap water for sodium chloride line 60na and unpurified water line 60a may be cold, ambient temperature or hot (e.g., preheated). A third line 60j in parallel with sodium chloride line 60na and unpurified water line 60a operates with a preheat valve 64j to allow any unwanted water, e.g., used for preheating, to be delivered to drain 62.

Another primary difference with distillation unit 10c is that dual stage water condensing is used to cool steam or vaporized water into purified water. Both high temperature condenser 78a and low temperature condenser 78b are cooled using cold tap water from tap water source TW or storage tank 20. Cooling line 60i operating with a cooling valve 64i extends from tap water source TW or storage tank 20 into low temperature condenser 78b. Cooling line 60i continues with warmer water from condenser 78b to high temperature condenser 78a. Cooling line 60i with even warmer water then continues from condenser 78a to drain 62. In an alternative embodiment, cooling line 60i may extend in the opposite order from tap water source TW or storage tank 20 first into high temperature condenser 78a, and then continue with warmer water to low temperature condenser 78b.

Condensers 78a and 78b may each include a serpentine pathway (not illustrated) within which steam (or steam/water) travels and condenses into purified water as the cooling water flows over the multiple turns and runs of the serpentine pathway. Heat fins may or may not be provided with the serpentine pathway(s). Purified water exits low temperature condenser 78b along purified water line 60d though at least one finishing filter, illustrated here as a single sterilizing ultrafilter 18, e.g., less than 0.22 micron filter. WFI may then flow to accumulator chamber or bladder 124b of disposable set described in connection with FIG. 10 or to an accumulator chamber or bladder associated with distillation unit 10c. Any and All pumps and sensors discussed in connection with distillation unit 10a, and controlled by and/or outputting to control unit 24, are equally applicable and expressly contemplated for distillation unit 10c of FIG. 11.

Figure 12:
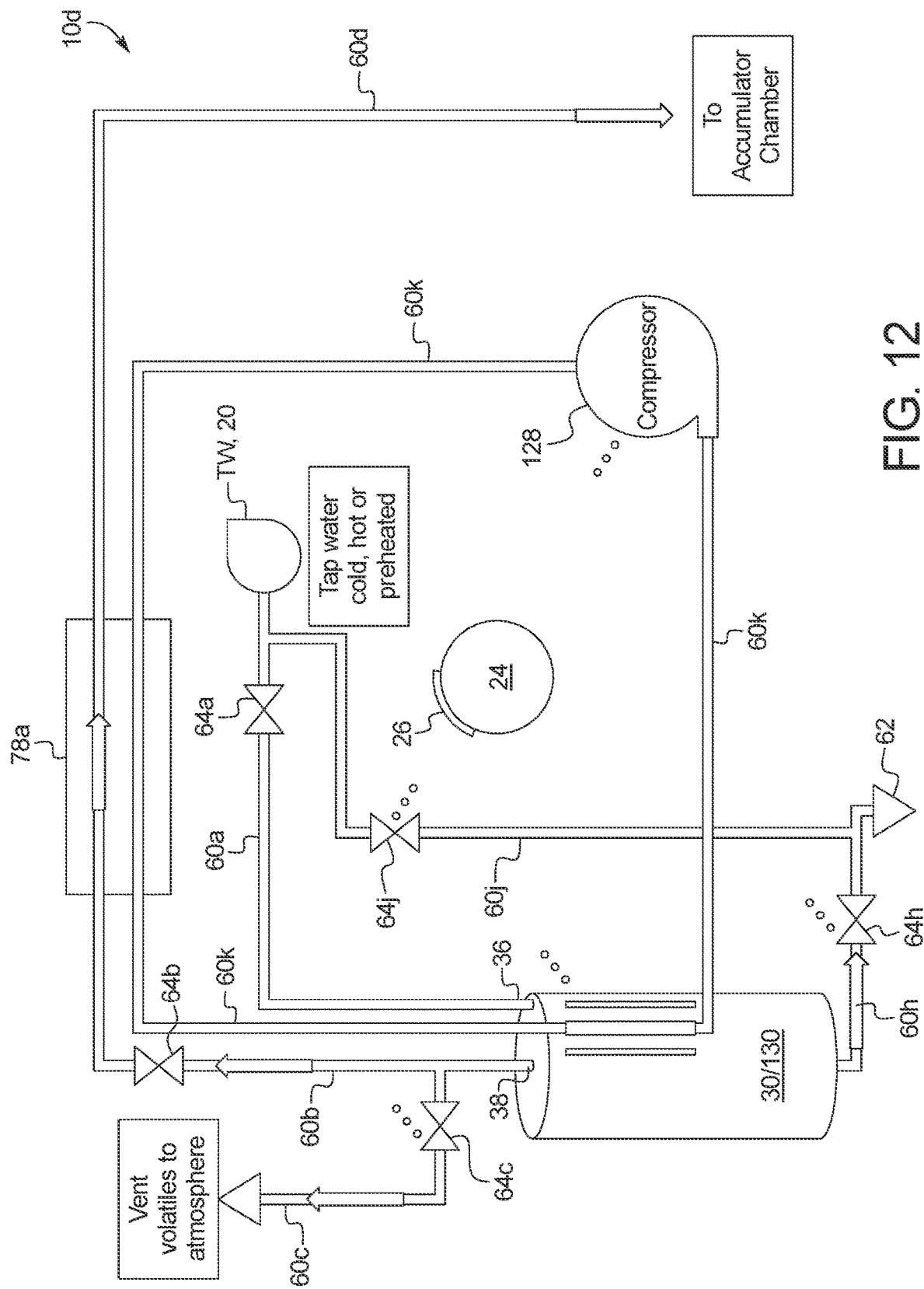
FIG. 12 is a schematic view of a further alternative purified water generation or distillation unit of the present disclosure.

Referring now to FIG. 12, a further alternative water generation unit or distillation unit 10d is illustrated. Distillation unit 10d, like distillation units 10b and 10c, uses water cooled condensing as opposed to electromechanical condenser 80 of distillation unit 10a. Distillation unit 10d uses many of the same components, such as heater or boiler 30/130 discussed above as well as many of the same lines and valves as discussed in connection with FIGS. 2 and 11. Those components and lines are numbered the same in FIG. 12, and all disclosure concerning those components, including any alternative structure and functionality described for same, is applicable to and associated with distillation unit 10d. Also, any and all pumps, valves, and sensors discussed in connection with distillation unit 10a, and controlled by and/or outputting to control unit 24 are equally applicable and expressly contemplated for distillation unit 10d of FIG. 12. Any and all finishing filters discussed in connection with distillation unit 10a are equally applicable and expressly contemplated for distillation unit 10d of FIG. 12.

The primary difference with distillation unit 10d is that online tap water is not required for cooling and condensing. Instead a condensing heat pump 128 (refrigerator), under control of control unit 24, is provided to cool water exiting heater 30/130 along closed loop line 60k. Condensing heat pump 128 in an embodiment may be a 5000 British Thermal Unit ("BTU") heat pump, which may have a six Amp, 125 VAC input. Condenser 78a may include a serpentine pathway (not illustrated) within which the steam (or steam/water) travels and condenses into purified water as the cooling water from compressor or condensing heat pump 128 flows over the multiple turns and runs of the serpentine pathway. Heat fins may or may not be provided with the serpentine pathway. The cooled water is then pumped by condensing heat pump 128 along closed loop line 60k and through high temperature condenser 78a to condense the steam or vaporized water from heater 30/130 to form cooled purified water (which may be further filtered to provide WFI) and delivered to a water accumulator as illustrated in FIG. 12.

Heated water from condenser 78a flows along closed loop line 60k into heater 30/130 to provide secondary heating to the incoming water from tap source TW or water tank 20. It is also contemplated to recoup heat from condensing heat pump 128 to preheat incoming water from tap source TW or water tank 20. The loop just described is then repeated. It is believed that distillation unit 10d conserves both water usage and heating energy.

Applications Using Water from Distillation Unit

Figure 13:
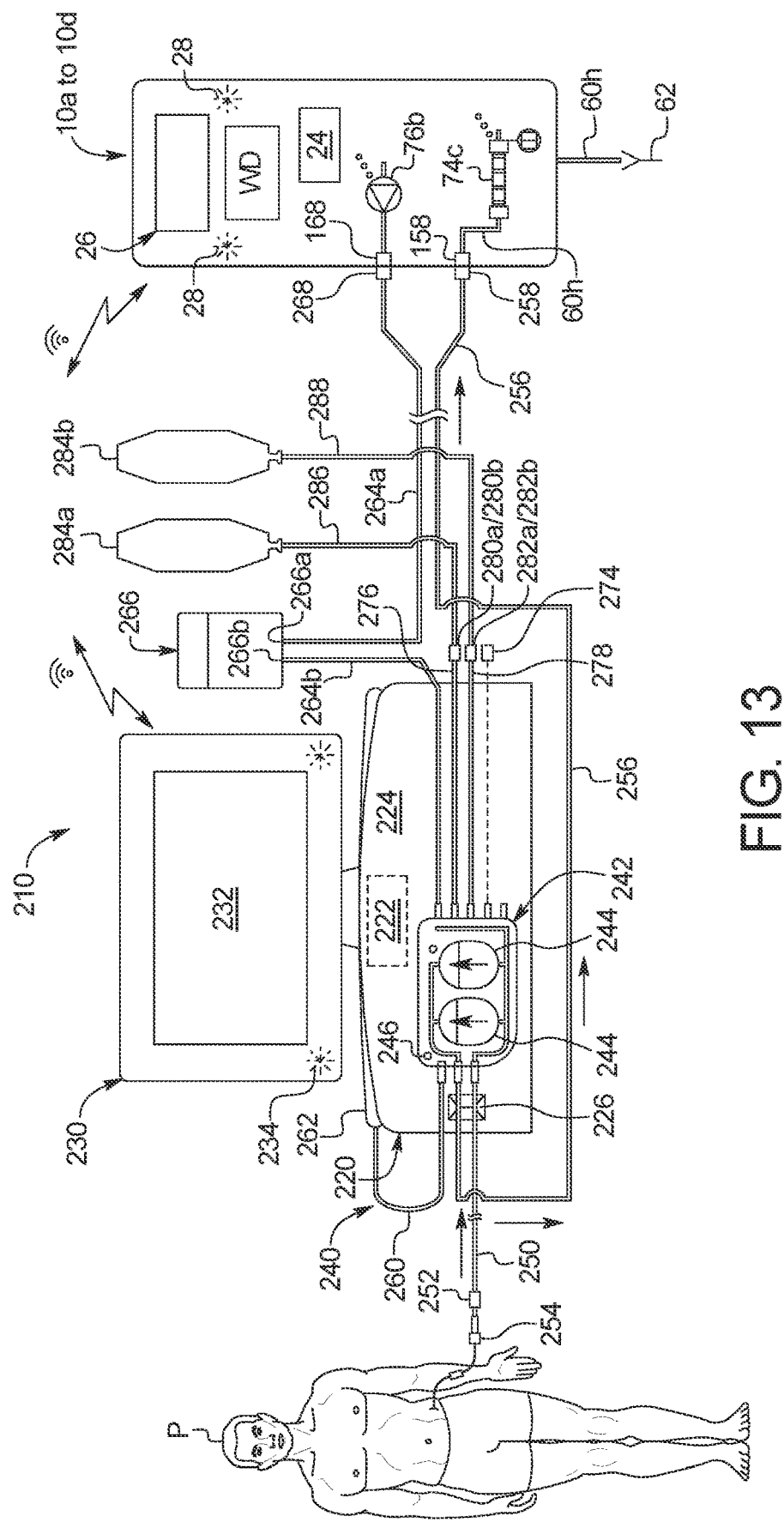
FIG. 13 is a schematic view of an embodiment of any of the distillation units of the present disclosure operating in a point of use peritoneal dialysis system.

The water purification or distillation units 10a to 10d just described are useful in many different applications. A first application of the distillation units is described above in connection with system 120 (e.g., a dialysis unit) and FIG. 10 where WFI is used in a PD application with disposable set 124 and a PD cycler operating set 124. FIG. 13 illustrates a second application of distillation units 10a to 10d, here with a second point of use peritoneal dialysis system 210 (e.g., a dialysis unit). System 210 includes a cycler 220 (e.g., a fluid preparation structure) and one of water purification or distillation units 10a to 10d. Suitable cyclers for cycler 220 include, e.g., the Amia® or HomeChoice® cycler, with the understanding that those cyclers are provided with updated programming to perform and use the point of use dialysis fluid produced according to system 210. To this end, cycler 220 includes a control unit 222 having at least one processor and at least one memory. Control unit 222 further incudes a wired or wireless transceiver for sending information to and receiving information from distillation unit 10a to 10d. As discussed herein, distillation unit 10a to 10d includes a control unit 24 having at least one processor and at least one memory. Control unit 24 further incudes a wired or wireless transceiver for sending information to and receiving information from control unit 222 of cycler 220. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology.

Cycler 220 includes a housing 224, which holds equipment programmed via control unit 222 to prepare fresh dialysis solution at the point of use, pump the freshly prepared dialysis fluid to patient P, allow the dialysis fluid to dwell within patient P, then pump used dialysis fluid to a drain. As described above, distillation unit 10a to 10d includes a collected impurities or drain line 60h leading to a drain 62, which can be a house drain or a drain container. The equipment programmed via control unit 222 to prepare fresh dialysis solution at the point of use in an embodiment includes equipment for a pneumatic pumping system, including but not limited to (i) one or more positive pressure reservoir, (ii) one or more negative pressure reservoir, (iii) a compressor and a vacuum pump each under control of control unit 222, or a single pump creating both positive and negative pressure under control of control unit 222, to provide positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off pneumatic solenoid valves under control of control unit 222 located between the plural pneumatic valve chambers and the plural fluid valve chambers, (vii) plural electrically actuated variable orifice pneumatic valves under control of control unit 222 located between the plural pneumatic pump chambers and the plural fluid pump chambers, (viii) a heater under control of control unit 222 for heating the dialysis fluid as it is being mixed in one embodiment, and (ix) an occluder 226 under control of control unit 222 for closing the patient and drain lines in alarm and other situations.

In one embodiment, the plural pneumatic valve chambers and the plural pneumatic pump chambers are located on a front face or surface of housing 224 of cycler 220. A heater is located inside housing 224 and in an embodiment includes heating coils that contact a heating pan or tray, which is located at the top of housing 224, beneath a heating lid (not seen in FIG. 13).

Cycler 220 in the illustrated embodiment includes a user interface 230. Control unit 222 in an embodiment includes a video controller, which may have its own processing and memory for interacting with primary control processing and memory of control unit 222. User interface 230 includes a video monitor 232, which may operate with a touch screen overlay placed onto video monitor 232 for inputting commands via user interface 230 into control unit 222. User interface 230 may also include one or more electromechanical input device, such as a membrane switch or other button. Control unit 222 may further include an audio controller for playing sound files, such as voice activation commands, at one or more speaker 234.

FIG. 13 also illustrates one embodiment of disposable set 240, which is operated by cycler 220 to move fluid within the disposable set 240, e.g., to mix dialysis fluid as discussed herein. Disposable set 240 in the illustrated embodiment includes a disposable cassette 242, which may include a planar rigid plastic piece covered on one or both sides by a flexible membrane. The membrane pressed against housing 224 of cycler 220 forms a pumping and valving membrane. Disposable cassette 242 includes fluid pump chambers 244 that operate with the pneumatic pump chambers located at housing 224 and fluid valve chambers 246 that operate with the pneumatic valve chambers located at housing 224.

Disposable set 240 further includes a patient line 250 that extends from a patient line port of cassette 242 and terminates at a patient line connector 252. Patient line connector 252 connects to a patient transfer set 254, which in turn connects to an indwelling catheter located in the peritoneal cavity of Patient P. Disposable set 240 includes a drain line 256 that extends from a drain line port of cassette 242 and terminates at a drain line connector 258, which connects removeably to a corresponding drain connector 158 of distillation units 10*a* to 10*d*.

Disposable set 240 also includes a heater/mixing line 260 that extends from a heater/mixing line port of cassette 242 and terminates at a heater/mixing bag 262 for mixing and heating fresh PD fluid. Disposable set 40 as illustrated includes an upstream water line segment 264*a* that extends to a water inlet 266*a* of water accumulator 266. A downstream water line segment 264*b* extends from a water outlet 266*b* of water accumulator 266 to cassette 242. In the illustrated embodiment, upstream water line segment 264*a* begins at a water line connector 268 and is located upstream from water accumulator 266. Water line connector 268 is removeably connected to a water outlet connector 168 of distillation units 10*a* to 10*d*.

Distillation units 10*a* to 10*d* output WFI suitable for peritoneal dialysis. As discussed herein, to ensure WFI, distillation units 10*a* to 10*d* are provided with finishing filters 16, 18*a*/18*b*. A last bag may be provided that connects to a line from cassette 242 that terminates at a connector 274, which may be connected to a mating connector of a premixed last fill bag of dialysis fluid or to a sample bag or other sample collecting container. Last bag connector 274 may be used alternatively for a third type of concentrate if desired.

FIG. 13 illustrates that disposable set 240 includes a first, e.g., glucose, concentrate line 276 extending from a first concentrate port of cassette 242 and terminates at a first, e.g., glucose, cassette concentrate connector 280*a*. A second, e.g., buffer, concentrate line 278 extends from a second concentrate port of cassette 242 and terminates at a second, e.g., buffer, cassette concentrate connector 282*a*. A first concentrate container 284*a* holds a first, e.g., glucose, concentrate, which is pumped from container 284*a* through a container line 286 to a first container concentrate connector 280*b*, which mates with first cassette concentrate connector 280*a*. A second concentrate container 284*b* holds a second, e.g., buffer, concentrate, which is pumped from container 284*b* through a container line 288 to a second container concentrate connector 282*b*, which mates with second cassette concentrate connector 282*a*.

In an embodiment, to begin treatment, patient P loads cassette 242 into cycler and in a random or designated order (i) places heater/mixing bag 262 onto cycler 220, (ii) connects upstream water line segment 264*a* to water outlet connector 168 of distillation units 10*a* to 10*d*, (iii) connects drain line 256 to drain connector 158 of distillation units 10*a* to 10*d*, (iv) connects first cassette concentrate connector 280*a* to first container concentrate connector 280*b*, and (v) connects second cassette concentrate connector 282*a* to second container concentrate connector 282*b*. At this point, patient connector 252 is still capped. Once fresh dialysis fluid is prepared and verified, patient line 250 is primed with fresh dialysis fluid, after which Patient P may connect patient line connector 252 to transfer set 254 for treatment. Each of the above steps may be illustrated graphically at video monitor 232 and/or be provided via voice guidance from speakers 234.

Control unit 222 may be programmed to cause cycler 220 to perform one or more mixing action to help mix dialysis fluid properly and homogeneously for treatment. For example, any of fluid pump chambers 244 may be caused to withdraw into the pump chambers some amount of mixed fluid (e.g., made from one or both first and second concentrates 284*a*, 284*b* and WFI) from heater/mixing bag 262 and send such mixture back to heater/mixing bag 262 and repeat this procedure multiple times (described herein as a mixing sequence or "waffling"). In particular, to perform a mixing sequence, control unit 222 in an embodiment causes cycler 220 to close all fluid valve chambers 246 at cassette 242 except for the fluid valve chamber 246 to heater/mixing line 260 and heater/mixing bag 262. Fluid pump chambers 244 are stroked sequentially and repeatedly (i) pulling a possibly unmixed fluid combination of WFI and concentrates from heater/mixing bag 262 into the pump chambers, followed by (ii) pushing the mixed WFI and concentrates from the pump chambers back to heater/mixing bag 262 and (iii) repeating (i) and (ii) at least one time. Control unit 222 may be programmed to stroke fluid pump chambers 244 together so that they both pull and push at the same time, or alternatingly so that one pump chamber 244 pulls from heater/mixing bag 262, while the other pump chamber 244 pushes to heater/mixing bag 262, creating turbulence in heater/mixing line 260.

As illustrated in FIG. 13, distillation units 10*a* to 10*d* include purified water pump 76*b* as discussed above to pump purified water (e.g., an amount of water commanded by control unit 222 to control unit 24) through one or more finishing filter 16, 18a/18b and to deliver resulting WFI to water accumulator 266. Distillation units 10a to 10d are also illustrated as having an additional conductivity sensor 74c (which may be compensated for temperature via an additional temperature sensor (not illustrated)) located along and operable with drain line 60h. The purpose of additional conductivity sensor 74c is so that when fresh dialysis fluid is being prepared, a sample of the fresh dialysis fluid may be delivered via drain lines 256 and 60h to conductivity sensor 74c to verify that dialysis fluid mixing has been performed properly. If for some reason, dialysis fluid has not been mixed properly, the improperly mixed sample may be sent easily to drain 62.

It has been found that a prototype of resistive heater or boiler 30 can make two liters of WFI in about forty-eight minutes when applying 1875 Watts of power to the heater or boiler (as mentioned above, power within a home residence may be limited to, e.g., 1500 Watts, while power in a clinic, hospital, etc., may be increased to, e.g., 2400 Watts, 20 A 120 VAC in the US). Two liters is a typical fill amount for a peritoneal dialysis patient. Here, once disposable set 240 is installed on cycler 220 and connected to water purification or distillation unit 10a to 10d, an initial batch of WFI may be produced and delivered to water accumulator 266, e.g., via purified water pump 76b of the distillation unit. Cycler 220 then operates disposable set 240 to mix a first, e.g., glucose, concentrate from container 284a and a second, e.g., buffer, concentrate from container 284b with WFI from water accumulator 266, e.g., in a manner described above, to produce fresh dialysis fluid, which is mixed and heated within heater/mixing bag 262. Once the fresh dialysis fluid reaches treatment temperature, e.g., 37° C., cycler 220 operates disposable set 240 to deliver the fresh, heated dialysis fluid to Patient P via patient line 250, patient line connector 252 and patient transfer set 254. After a dwell period of one to two hours, for example, cycler 220 operates disposable set 240 to deliver used dialysis fluid from Patient P to drain 62 via patient line 250, disposable cassette 242 and drain line 256.

The above sequence describes a complete, fill, dwell and drain cycle. It should be noted that in many cases, Patient P begins a new treatment full of used dialysis fluid from the previous treatment, which needs to be removed to drain prior to the first fill of the new treatment. Viewing FIG. 13, cycler 220 may operate disposable set 240 to deliver Patient P's last fill from an earlier treatment to drain 62 via patient line 250, disposable cassette 242 and drain line 256, while distillation unit 10a to 10d prepares and delivers WFI to water accumulator 266. In this instance, WFI preparation time is not adding or significantly adding to the overall treatment time because Patient P has to wait for the prior treatment's last fill to be discarded before receiving a first fill.

For all fills after the first fill, distillation unit 10a to 10d can be commanded by control unit 222 of cycler 220 to begin preparing WFI and delivering the WFI to water accumulator 266 as soon as the WFI for the ongoing cycle is removed from the water accumulator and mixed with concentrates in heater/mixing bag 262. The forty-eight minutes, for example, to make two liters of water using a distillation unit having heater or boiler 30 is less, and perhaps significantly less, than Patient P's prescribed dwell period, e.g., one to two hours. It may therefore be possible, and it is contemplated to program system 210, to (i) prepare WFI at distillation unit 10a to 10d, (ii) deliver the WFI to water accumulator 266, and (iii) mix and heat WFI and concentrates from sources 284a and 284b in heater/mixing bag 262 prior to the completion of a current dwell. In this manner, system 210 is able to perform a new fill as soon as Patient P is fully drained, thereby optimizing the total treatment time.

System 210 also allows for a last fill using a third, different concentrate connected to last bag connector 274, which is formulated to remain within Patient P's peritoneum for a prolonged duration. A final drain in such as case is not performed and Patient P exits treatment and disconnects from system 210 full with the last fill.

In a third application, the water purification or distillation unit 10a to 10d of the present disclosure is used to output ultrapure water for mixing with HD concentrates, such as acid and bicarbonate concentrates, to prepare an HD solution for delivery to a dialyzer. Because the dialyzer provides another layer of filtration via its hollow fiber membranes, ultrapure water as opposed to WFI will suffice. Here, the at least one finishing filter 16, 18a/18b discussed herein for the water purification unit may not be needed. The water purification units of the present disclosure may for example be used in place of water supply 30 disclosed in U.S. Pat. No. 9,724,458 ("the '458 Patent), entitled "Hemodialysis System", filed May 24, 2012, the entire contents of which are incorporated herein by reference and relied upon. The water purification units of the present disclosure output water of the same quality (e.g., ultrapure) as that of water supply 30 of the '458 Patent, and may do so at an elevated temperature so as to lessen the burden on the inline heater 72 of the '458 patent.

The pumping mechanisms of the '458 Patent are actuated pneumatically. It is contemplated however for the water purification unit of the present disclosure to operate with a PD cycler or HD machine having any suitable type of pumping mechanism, such as pneumatic pumping, peristaltic pumping (rotary or linear), gear pumping, platen pumping, volumetric pumping via a motor (e.g., stepper motor) connected to a rotary to linear motion conversion apparatus (e.g., lead screw), and combinations thereof. It is also contemplated for the water purification unit of the present disclosure to operate with a PD cycler or HD machine having any suitable type of heating, such as batch heating, inline heating, resistive heating, inductive heating, radiant heating, and combinations thereof. It is further contemplated for the water purification unit of the present disclosure to operate with a PD cycler or HD machine having any suitable type of valve actuation, such as pneumatic actuation, pinch valve actuation, spring actuation, and combinations thereof.

Figure 14:
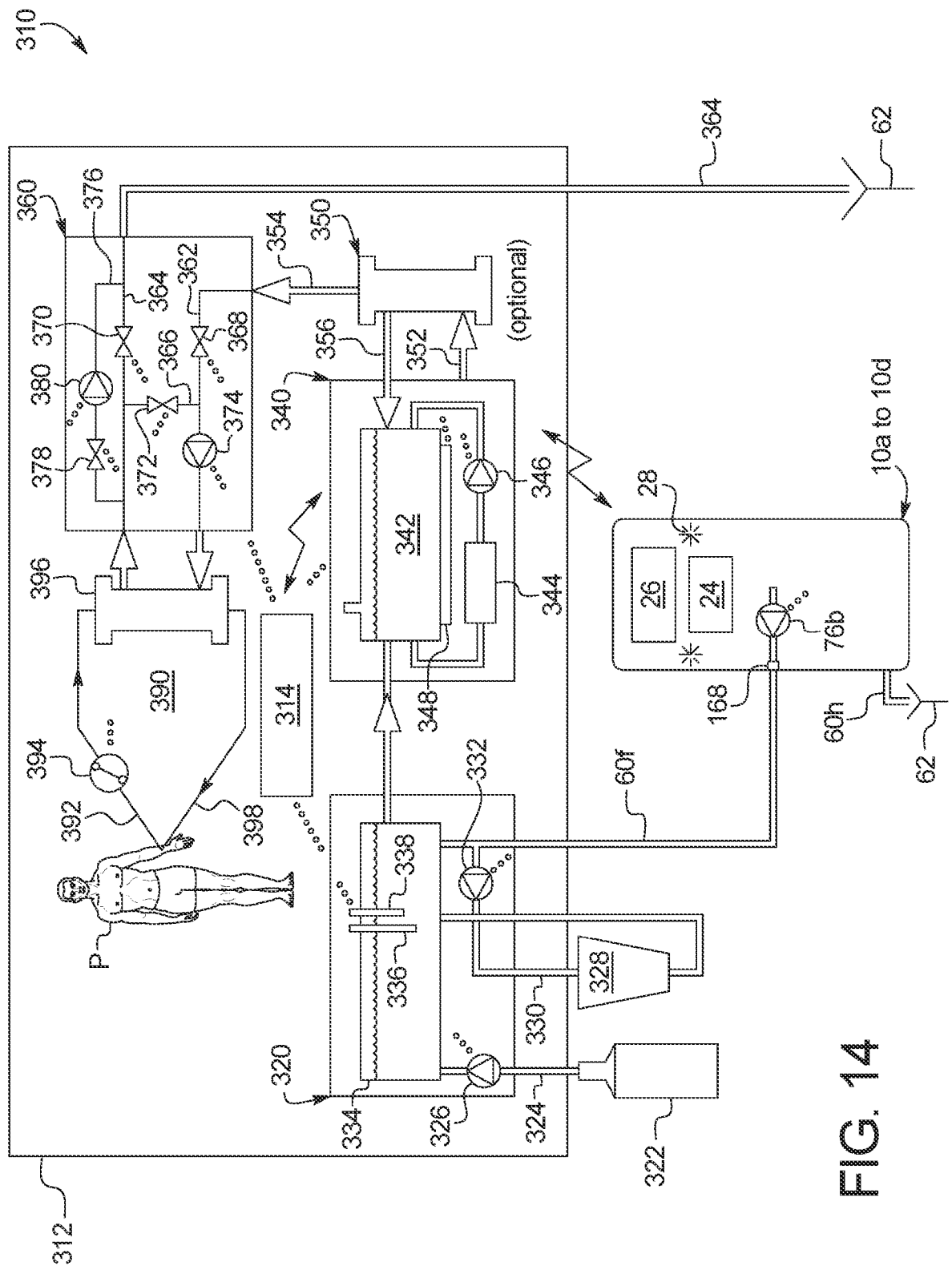
FIG. 14 is a schematic view of an embodiment of any of the distillation units of the present disclosure operating in a point of use hemodialysis dialysis system.

FIG. 14 illustrates an HD application using distillation unit 10a to 10d, here with a hemodialysis system 310 (e.g., a dialysis unit). Hemodialysis system 310 includes a hemodialysis machine 312 under control of a control unit 314, which includes any and all structure, functionality and alternatives discussed for control units 24 and 222. Control unit 314 is in wired or wireless (as illustrated) communication with control unit 24 of distillation unit 10a to 10d so that data may be sent back and forth between HD machine 12 and the distillation unit as discussed herein.

Hemodialysis machine 312 includes three dialysis fluid sub-assemblies, including a mixing subassembly 320 (e.g., a fluid preparation structure), a deaeration and heating subassembly 340 and a dialysis fluid delivery subassembly 360. Subassemblies 320, 340 and 360 reside in one embodiment within a same enclosure of hemodialysis machine 312. Mixing subassembly 320 includes an acid concentrate source 322, an acid concentrate line 324, and an acid concentrate pump (e.g., gear pump) 326 under control of control unit 314. Mixing subassembly 320 also includes bicarbonate concentrate source 328, a bicarbonate concentrate line 330, and a bicarbonate concentrate pump (e.g., gear pump) 332 under control of control unit 314.

Distillation unit 10a to 10d delivers ultrapure water (WFI not needed because dialyzer 396 acts as a sterile barrier), e.g., via purified water pump 76b, to mixing subassembly 320, including both to bicarbonate concentrate pump 332 and to a mixing tank 334 in the illustrated embodiment. In the illustrated embodiment, bicarbonate concentrate source 328 is a dry powder source, wherein bicarbonate concentrate pump 332 pumps ultrapure water though the cartridge of bicarbonate concentrate source 328, which becomes saturated with bicarbonate before entering mixing tank 334. Mixing tank 334 is provided with conductivity and temperature sensors 336 and 338, respectively, providing a temperature compensatable conductivity readout to control unit 314. In an embodiment, bicarbonate is added to ultrapure water in mixing tank 334 until the temperature compensated readout from sensors 336 and 338 achieves a desired or preset bicarbonate value as determined by control unit 314. Next, control unit 314 causes acid concentrate pump 326 to meter acid concentrate into the mixture of ultrapure water and bicarbonate until the temperature compensated readout from sensors 336 and 338 achieves a desired or preset dialysis fluid value as determined by control unit 314. In an alternative embodiment, mixing may be performed using precise pumping of known amounts of ultrapure water, acid and bicarbonate, which is then verified via sensors 336 and 338.

Fresh dialysis fluid is then delivered, e.g., via a pump not illustrated from mixing subassembly 320 to a deaeration and heating subassembly 340. Deaeration and heating subassembly 340 includes expansion tank 342, which deaerates the fresh dialysis fluid, removing bubbles from the dialysis fluid, which has been degassed in a chamber 344 via a degassing pump 346, e.g., located below expansion tank 342. A heater 348 under control of control unit 314 heats the dialysis fluid for treatment to body temperature, e.g., 37° C.

It should be appreciated that the order of mixing subassembly 320 and deaeration and heating subassembly 340 may be reversed, so that ultrapure water is delivered from distillation unit 10a to 10d instead to deaeration and heating subassembly 340, to deaerate and heat the ultrapure water, which is then delivered to mixing subassembly 320 to prepare fresh, heated dialysis fluid. In either case, an optional ultrafilter 350 may be provided to further purify the dialysis fluid. Ultrafilter 350 may be needed if it is determined that contamination is introduced via acid concentrate from acid concentrate source 322 and/or, bicarbonate concentrate from bicarbonate concentrate source 328. In the illustrated embodiment, ultrapure dialysis fluid flows from deaeration and heating subassembly 340 to ultrafilter 350 via ultrafilter inlet line 352 (e.g., via a pump not illustrated), further purified fresh dialysis fluid flows from ultrafilter 350 to dialysis fluid delivery subassembly 360 via fresh dialysis fluid line 354, while reject dialysis fluid from ultrafilter 350 is returned to expansion tank 342 of deaeration and heating subassembly 340. Chances are, however, that optional ultrafilter 350 is not needed and that dialyzer 396 acting as an additional sterile barrier is sufficient to remove any impurities obtained via mixing.

In the illustrated embodiment, dialysis fluid delivery subassembly 360 includes a fresh dialysis fluid line 362, a used dialysis fluid line 364, a bypass or recirculation line 366, a fresh dialysis fluid valve 368, a used dialysis fluid valve 370, a bypass or recirculation valve 372, a dialysis fluid pump 374, an ultrafiltration or "UF" line 376, a UF valve 378 and a UF pump 380. All valves and pumps are under control of control unit 314 in one embodiment as illustrated via the dotted lines leading from the pumps and valves. It is contemplated that mixing subassembly 320 and deaeration and heating subassembly 340 are reusable, while dialysis fluid delivery subassembly 360 is reusable, disposable or some combination thereof. If reusable, valves 368, 370, 372 and 378 may be electrically actuated inline solenoid valves under control of control unit 314, while pumps 374 and 380 may be gear pumps under control of control unit 314. If disposable, valves 368, 370, 372 and 378 may be electrically actuated solenoid pinch valves that pinch and unpinch tubing or be portions of a disposable cassette operated by actuators under control of control unit 314 that operate pneumatically, electrically, and/or mechanically. Disposable pumps may include peristaltic tubing pumps under control of control unit 314 or areas of a disposable cassette operated by actuators under control of control unit 314 that operate pneumatically, electrically, and/or mechanically. In an embodiment, UF pump 380 regardless of its type is an accurate pump so as to accurately remove a prescribed amount of UF from Patient P. It should be appreciated that while a used dialysis fluid pump is not illustrated, one may be provided if needed.

As discussed herein, lab scale models of the distillation unit have shown that two liters of WFI may be produced in about forty-eight minutes when applying 1875 Watts of power to the distillation heater (as mentioned above, power within a home residence may be limited to, e.g., 1500 Watts, while power in a clinic, hospital, etc., may be increased to, e.g., 2400 Watts, 20 A 120 VAC in the US). It is contemplated that the output will be improved via sizing and optimization of condenser 80. Even so, it may be difficult to produce water at a rate sufficient for HD dialysis fluid supply, which may, for example, be 200 mL/min. It is accordingly contemplated to recirculate the dialysis fluid through dialyzer 396 a number of times to allow distillation unit 10a to 10d enough time to prepare another batch of purified water and for mixing subassembly 320 and deaeration and heating subassembly 340 to mix, deaerate and heat another batch of fresh dialysis fluid. For recirculation, drain valve 370 is closed, while fresh dialysis fluid valve 368 and recirculation valve 372 are open to allow fresh dialysis fluid pump 374 to pull fresh dialysis fluid from deaeration and heating subassembly 340 and push the fresh dialysis fluid through dialyzer 396, through a portion of drain line 364, through bypass or recirculation line 366 and back through the pump to the dialyzer. If two liters (2000 mL) of ultrapure water are made every forty-eight minutes, and the dialysis fluid flowrate is 200 mL/min, then each batch of two liters may be circulated approximately five times through dialyzer 396 (2000 mL/200 mL/min=10 mins×five circulations through the dialyzer to provide enough time for the next batch).

It is contemplated that the dialysis fluid will have residual osmotic effect through at least most of the circulations through dialyzer 396. When the next batch of mixed, deaerated and heated dialysis fluid is ready at deaeration and heating subassembly 340, or perhaps some time before, fresh dialysis fluid valve 368 and bypass valve 372 are closed, used dialysis fluid valve 370 is opened, and pump 374 (and/or a used dialysis fluid pump) pumps used dialysis fluid through drain line 364, to drain 62. UF valve 378 and UF pump 380 are operated independently via control unit 314 to remove a prescribed amount of UF safely from Patient P to drain 62 via drain line 364 over the course of the recirculating and draining of the dialysis fluid just described.

HD system 310 as illustrated also includes a blood circuit 390, which includes an arterial line 392, a blood pump (e.g., peristaltic) 394 located in the arterial line, dialyzer 396, and venous line 398. In the illustrated embodiment, blood flow through dialyzer 396 is in a direction counter to that of simultaneously flowed dialysis fluid. Blood circuit 390 is illustrated generally and may include additional components, such as one or more air trap, pressure sensors, one or more air detector, a hematocrit sensor, and/or access disconnection detection. All sensors and blood pump 394 are under control of control unit 314. Dialysis fluid subassemblies 320, 340 and 360 are also illustrated generally and may include additional sensing and components, such as pressure sensors, additional pumps, and a blood leak detector.

Figure 15:
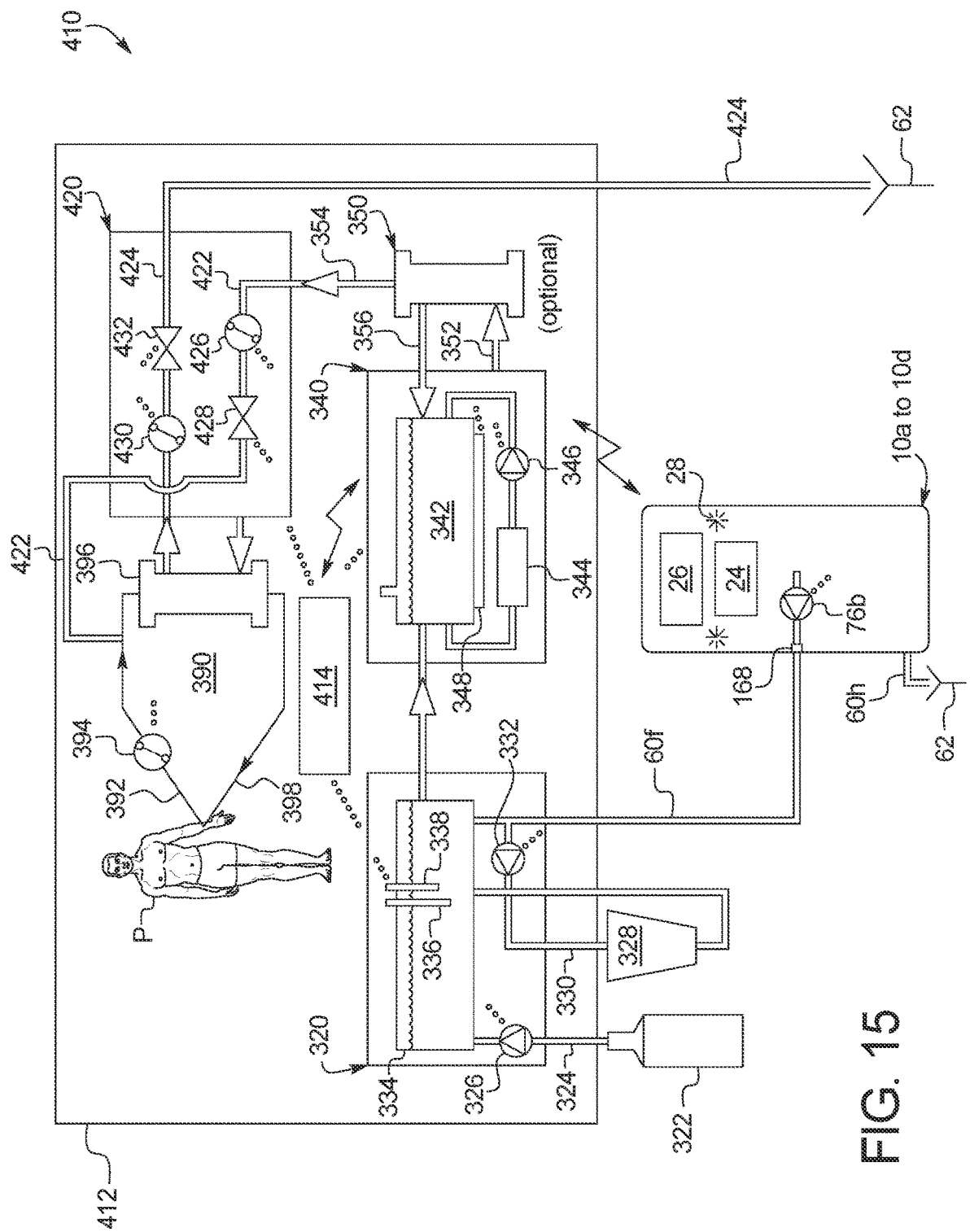
FIG. 15 is a schematic view of an embodiment of any of the distillation units of the present disclosure operating in a point of use hemofiltration system.

FIG. 15 illustrates a third type of application using distillation unit 10a to 10d, here with a hemofiltration, e.g., chronic or CRRT, system 410 (e.g., a dialysis unit). Hemofiltration system 410 includes a hemofiltration machine 412 having a control unit 414 configured to run hemofiltration treatments. Distillation unit 10 to 10d and replacement fluid subassemblies 320 and 340, including all structure, functionality, interaction and alternatives discussed above in connection with system 310 of FIG. 14 are equally applicable to hemofiltration system 410. Possible distinctions are that it is more likely that distillation unit 10 to 10d will use finishing filters 16, 18a/18b to produce WFI because injectable quality replacement fluid is needed for hemofiltration system 410. To that end, it is more likely that one ore more downstream ultrafilter 350 is used, e.g., in case of contamination due to mixing with concentrates from acid concentrate source 322 and bicarbonate concentrate source 328. Additionally, the concentrates used for hemofiltration system 410 may be different than those used for HD system 310.

Replacement fluid delivery subassembly 420 (e.g., a fluid preparation structure) is different than dialysis fluid delivery subassembly 360. Replacement fluid delivery subassembly 420 may be reusable and/or replaceable, but for CRRT it is contemplated to combine replacement fluid delivery subassembly 420, blood circuit 390 including dialyzer 396 as a single or multi-piece disposable, which mounts to and is removable from hemofiltration machine 412. Replacement fluid pumps 426 and 430 and dialyzer 396 are accordingly illustrated as peristaltic pumps under the control of control unit 414 operating with disposable tubing. In a chronic setting, it is more likely that at least a portion of replacement fluid delivery subassembly 420 is reusable, in which replacement fluid pumps 426 and 430 may for example be inline (no disposable) gear pumps.

Replacement fluid delivery subassembly 420 is illustrated generally to include a fresh replacement fluid line 422, a used replacement fluid line 424, a fresh replacement fluid pump 426, a fresh replacement fluid valve 428, a used replacement fluid pump 430, and a used replacement fluid valve 432, each under control of control unit 414. During treatment, with valves 428 and 432 open, control unit 414 causes fresh replacement fluid pump 426 to deliver replacement fluid at a prescribed flowrate from ultrafilter 350, directly into arterial line 394, while used replacement fluid pump 430 pulls effluent from dialyzer 396 to drain 62. During such time, control unit 414 causes blood pump 394 to pump blood from Patient P, through dialyzer 396, and back to patient P. System 410 illustrates a pre-dilution example in which fresh replacement fluid is delivered to arterial line 392. System 410 is alternatively a post-dilution system in which fresh replacement fluid is delivered instead to venous line 398, or a combination pre- and post-dilution system in which fresh replacement fluid is delivered to both the arterial and venous lines.

A number of techniques are contemplated to control the amount of UF removed from Patient P. In one embodiment, flowmeters (invasive or non-invasive) are associated with fresh replacement fluid line 422 and used replacement fluid line 424. Control unit 414 uses feedback from the flowmeters (not illustrated) to control used replacement fluid pump 430 to run slightly faster than fresh replacement fluid pump 426, so as to remove more fluid from blood circuit 390 than is delivered to the blood circuit by a precise amount that meets Patient P's prescribed UF. In another embodiment, scales (not illustrated) are provided, e.g., at expansion tank 342 and with a drain container (not illustrated), which output to control unit 414 a before blood circuit 390 weight value and an after blood circuit 390 weight value, wherein the additional weight after the blood circuit measured at the drain container constitutes Patient P's UF. In a further alternative embodiment, volumetric balance chambers are provided to balance the flow of fresh replacement fluid to blood circuit 390 with the flow of used replacement fluid from dialyzer 396, and wherein a separate precise UF pump is additionally provided to remove and additional amount of used replacement fluid from dialyzer 396 to meet the patient's prescribed UF.

It should be appreciated that because fresh replacement fluid is delivered directly to blood circuit 390, it cannot be recirculated in the manner described above for HD system 310. For CRRT however, the prescribed fresh replacement fluid delivery flowrate to blood circuit 390 is often rather low, such that the 41 mL/min maximum replacement fluid delivery (two liters (2000 mL) in forty-eight minutes of WFI (2000 mL/48 min=41 mL/min) at 1875 Watts to heater 30) may be sufficient. Again, it is contemplated that higher output distillation units are quite likely. It is also contemplated to gang two or more distillation units 10a to 10d together for parallel or simultaneous operation if needed to meet the necessary dose (mL/min of replacement fluid) demand.

The water exiting from the water purification unit 10a to 10d is of a WFI quality when used to prepare replacement fluid, e.g., for hemofiltration ("HF") or hemodialfiltration ("HDF"), for chronic or acute (e.g., continuous reneal replacement therapy ("CRRT")) treatment, or for medication delivery (e.g., to make a drug, saline or lactated ringers). An HDF system may be provided by combining dialysis fluid delivery subassembly 360 of system 310 with replacement fluid delivery subassembly 420, and using mixing subassembly 320 and deaeration and heating subassembly 340. Here, the recirculation of HD system 310 may be combined with the direct blood circuit 390 delivery of HF system 410, e.g., with two or distillation units 10a to 10d ganged together, or one larger distillation unit 10a to 10d, to produce pre-dilution HDF, post-dilution HDF, or pre- and post-dilution HDF as desired. Any of the HD, HF and HDF systems may also provide anticoagulant, e.g., heparin or citrate delivery, which are separately made fluids.

Applications Employing Distillation for Reuse

In the applications described above for systems 120, 210, 310 and 410, distillation unit 10a to 10d of the present disclosure is used to purify water. In those systems, even if storage tank 20 is provided, it is contemplated to connect distillation unit 10a to 10d to a source of tap water. It should be appreciated however that the distillation units 10a to 10d are not limited to the purification of water only, and may be used to purify other fluids, such as used dialysis fluid, e.g., used PD, HD or replacement fluid.

Figure 16:
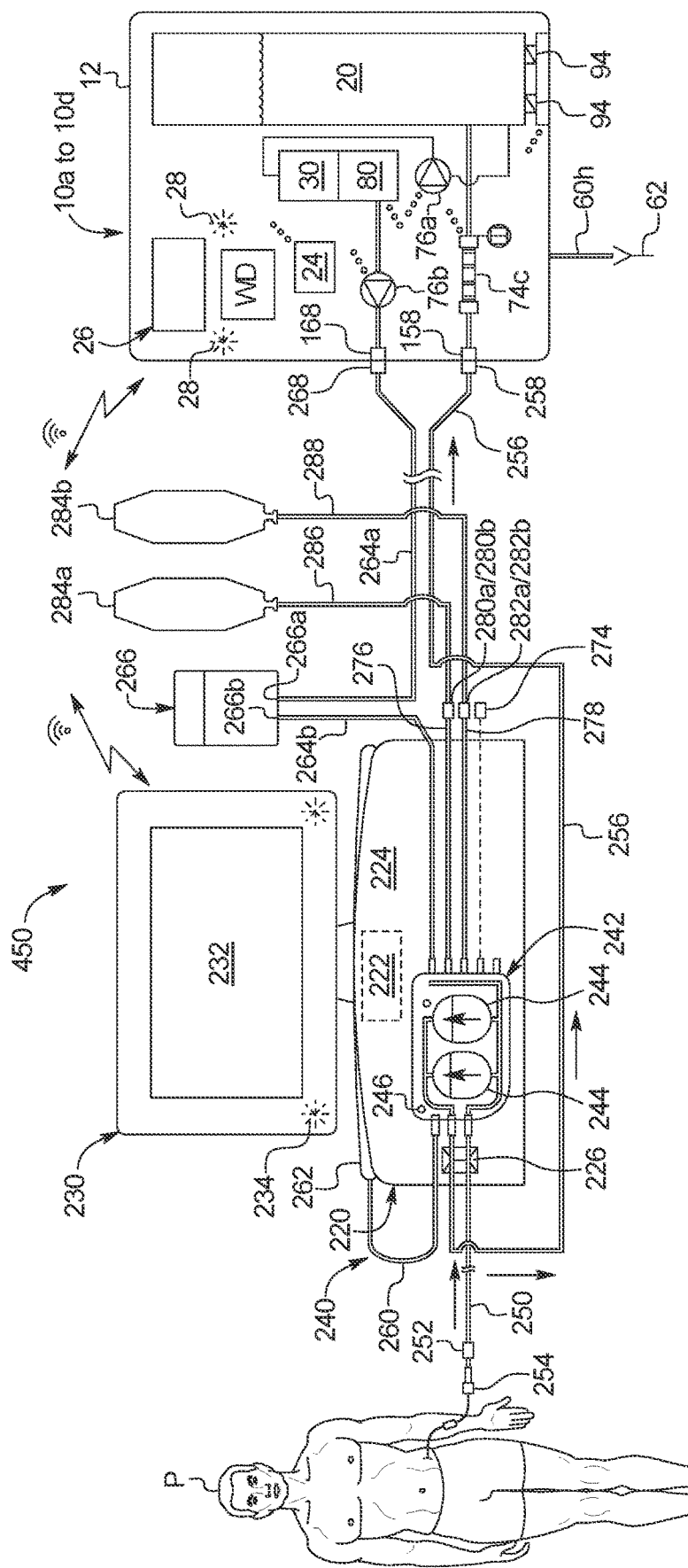
FIG. 16 is a schematic view of an embodiment of any of the distillation units of the present disclosure operating in a point of use peritoneal dialysis system, which reuses used peritoneal dialysis fluid.

FIG. 16 illustrates a PD example system 450, which is very similar to PD system 210, wherein any and all like-numbered structure, functionality and alternatives discussed for system 210 are equally applicable to system 450. One primary difference is that system 210 may receive unpurified water from a pressurized tap water source, however, system 450 does not require a connection to a tap water source. Also, in system 210, drain line 256 extends to a drain line connector 258, which connects removeably to a corresponding drain connector 158 of distillation unit 10a to 10d, after which effluent flows past conductivity sensor 74c, and from there to drain 62 via residue or collected impurities line 60h. In system 450, drain line 256 extends to drain line connector 258, which connects removeably to drain connector 158 of distillation unit 10a to 10d, after which efficient flows past conductivity sensor 74c, and from there to storage tank 20 instead of drain 62. In this manner, used PD dialysis fluid and accumulated UF from Patient P are reused via distillation unit 10a to 10d. Control unit 222 for reuse PD system 450 is programmed accordingly to perform the reuse flow sequences discussed herein.

In FIG. 16, distillation unit 10a to 10d is provided with storage tank 20, which may be accessed, e.g., via a hinged opening in housing 12, to pour, e.g., four liters of unpurified water into storage tank 20 and to remove the storage tank to empty same. Storage tank 20 is sized to hold an additional amount of UF removed from Patient P. In the illustrated embodiment, optional unpurified water pump 76a under control of control unit 222 is provided to pump unpurified water from tank 20 to heater 30 (heater 30 and condenser 80 shown generally), while purified water pump 76b under control of control unit 222 is provided to pump purified water, e.g., through finishing filters 16, 18a/18b, to water accumulator 266. The delivery of unpurified water from storage tank 20 to heater 30 is performed alternatively via head pressure within tank 20. As illustrated, conductivity sensor 74c is still available to test the mixed PD fluid as described above.

In one embodiment, control unit 222 of cycler 220 and control unit 24 of distillation unit 10a to 10d cooperate (e.g., via wired or wireless communication) to cause an initial two liters of tap water from tank 20 to be purified into WFI within the distillation unit, which is transferred to a water accumulator 266. Once two liters of WFI is delivered to water accumulator 266, PD cycler 220 makes two liters of PD dialysis fluid in the manner described above for system 210, which is performed using heater/mixing container 262, after which the two liters of PD dialysis fluid is delivered from container 262 to the peritoneum of Patient P.

During a patient dwell period after the initial fill (e.g., starting as soon as the first two liters leaves water accumulator 266), distillation unit 10a to 10d purifies the remaining two liters of tap water initially poured into tank 20, which is again transferred to water accumulator 266. Once the second two liters of WFI is delivered to water accumulator 266, PD cycler 220 makes a second two liters of PD dialysis fluid in the manner described in connection with system 210. The second two liters of PD is heated as needed in heater/mixing bag 262, while the initial batch of PD dialysis fluid dwells within Patient P.

At the end of the first dwell period, PD cycler 220 pumps used dialysis fluid from Patient P into storage tank 20 of distillation unit 10a to 10d. The used dialysis fluid will include ultrafiltrate removed from Patient P, so if two liters of dialysis fluid is delivered initially to Patient P, some amount greater than two liters will be pumped from Patient P to storage tank 20 as ultrafiltrate. Storage tank 20 as mentioned above is sized accordingly to hold the amount of ultrafiltrate removed from Patient P over the course of treatment.

After the initial two liters of used dialysis fluid and ultrafiltrate is removed from the Patient P to storage tank 20 of distillation unit 10a to 10d, PD cycler 220 pumps the second two liters of dialysis fluid from heater/mixing bag 262 to Patient P to begin a second dwell period. During the second dwell period (e.g., stating as soon as the later of (i) the second batch of WFI is removed from accumulator 266 or (ii) used dialysis is delivered to storage tank 20), distillation unit 10a to 10d boils the used dialysis fluid delivered from storage tank 20 and condenses the steam into ultrapure water, which one or more finishing filter 16, 18a/18b purifies into WFI, which is then delivered to the water accumulator 266. After two liters of WFI is delivered to water accumulator 266, PD cycler 220 pulls the two liters of WFI into the heater/mixing bag 262 along with PD concentrates to form a third batch of fresh PD dialysis fluid for treatment. The third batch of PD dialysis fluid is heated as needed and stored in heater/mixing bag 262 until the second patient dwell period is completed.

The above-described cycle of removing used dialysis fluid from Patient P to storage tank 20 of distillation unit 10a to 10d, filling Patient P with freshly made dialysis fluid, distilling and polishing/sterilizing the used dialysis fluid into WFI, storing the WFI in accumulator 266, and pumping the WFI along with PD concentrates to form PD dialysis fluid in heater/mixing bag 262 is repeated until Patient P's prescribed number of fill, dwell and drain cycles is completed. It should be appreciated that many times Patient P begins treatment already full of PD fluid from a midday exchange or from the previous night's treatment. Here, the patient or caregiver only has to fill storage tank 20 of distillation unit 10a to 10d with a single fill amount of tap water (e.g., two liters) because the second fill amount is provided from Patient P in the form of effluent. PD cycler 220 as a first machine step in the new treatment here involves delivering used dialysis fluid from Patient P, to mix in storage tank 20 with the tap water added by the patient or caregiver, which may be performed simultaneously with distillation unit 10a to 10d forming WFI and delivering same to accumulator 266. In this manner, total treatment time is conserved.

Likewise, at the end of treatment, if a last fill is to be delivered to Patient P, which the patient carries after disconnection from the PD cycler (and which may use a separate concentrate delivered via last bag connector 274), then the treatment ends upon the last fill, such that only a single fill volume's worth of used dialysis fluid, along with accumulated UF from Patient P resides in storage tank 20. The patient or caregiver removes storage tank 20 from distillation unit 10a to 10d and discards the used fluid to a house drain. In an embodiment, any volatiles, waste, toxins or other residuals removed from the initial tap water and the used dialysis fluid via heater 30 of the distillation 10a to 10d unit may be removed automatically or manually from heater 30 to storage tank 20 and into the used dialysis fluid prior to removal of storage tank 20 from the distillation unit 10a to 10d. In such a case, drain 62 illustrated with system 450 may not be needed. The volatiles may alternatively or additionally be vented to atmosphere as described herein.

As illustrated in FIG. 16, it is contemplated to provide one or more load cell 94 in distillation unit 10a to 10d beneath storage tank 20 and to be operable with control unit 24, so that it may be known when a fill volume's worth (e.g., two liters) of WFI has been produced via removal of tap water, used dialysis fluid, or combinations thereof from storage tank 20 to accumulator 266. Here, control units 24 and 222 of the distillation unit and the PD cycler, respectively, may communicate wired or wirelessly, such that the distillation control unit 24 sends a signal to the PD control unit 222 when enough WFI is present in water accumulator 266, such that the PD cycler may begin to make fresh dialysis fluid using the WFI. The weigh scale or load cell(s) 94 does not need to be precise because PD cycler 220 measures the amount of WFI removed from water accumulator 266 precisely for mixing with the PD concentrates. It is more important to make sure that enough WFI is present in water accumulator 266 to ensure that PD cycler 220 is able to prepare the prescribed fill volume's worth of fresh PD fluid. To that end, it is contemplated that a certain percentage more (e.g., ten percent) than the proscribed fill volume's worth of WFI be distilled and delivered to water accumulator 266. That extra amount of tap water may be filled by the patient or caregiver initially into storage container 20.

As discussed above, testing has shown that two liters of WFI may be produced in about forty-eight minutes when applying 1875 Watts of power to the distillation heater. Typical PD dwell times can be one hour or longer, allowing plenty of time for used dialysis fluid to be distilled, mixed and heated to form fresh dialysis fluid ready for use. One major advantage of system 450 using water purification or distillation unit 10a to 10d of the present disclosure is that a connection to house water is not needed. Also, the drain volume is contained and manageable. Further, if it can be shown that water accumulator 266 can be sterilized properly prior to treatment, and maintained in a sterilized manner, then the disposable water accumulator 266 of system 450 may become a non-disposable part of water purification or distillation unit 10a to 10d, reducing overall disposable cost.

Figure 17:
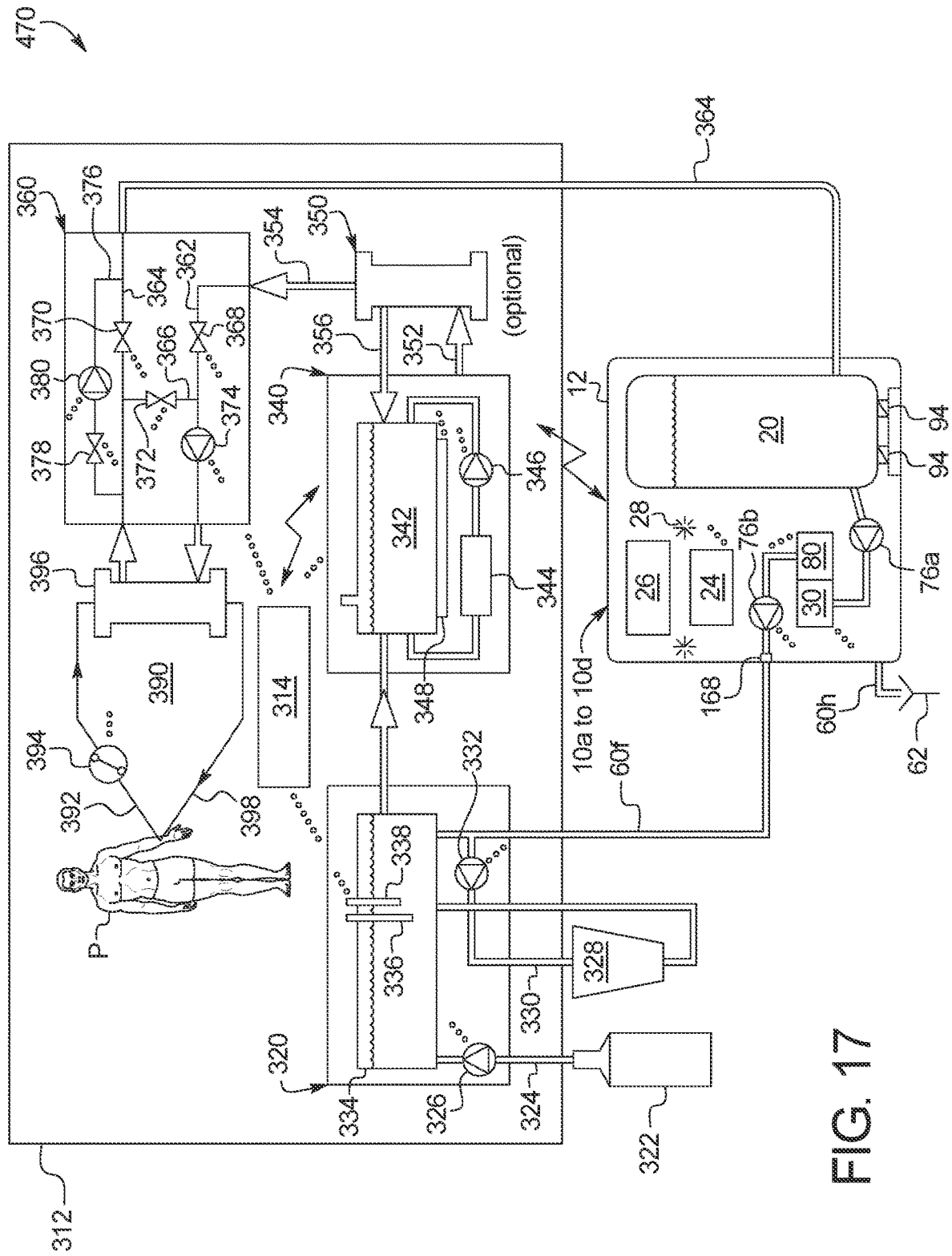
FIG. 17 is a schematic view of an embodiment of any of the distillation units of the present disclosure operating in a point of use hemodialysis system, which reuses used hemodialysis fluid.

System 470 of FIG. 17 illustrates that water purification or distillation unit 10a to 10d of the present disclosure may also be used to convert used HD fluid into ultrapure water for reuse. As discussed above for HD system 310 of FIG. 14, HD typically requires significantly more dialysis fluid than does PD and is typically a continuous rather than a batch treatment. It is therefore contemplated to (i) provide multiple parallel heaters 30 or distillation units 10a to 10d, (ii) upsize heaters 30, (iii) lower the dialysis fluid flowrate, or (iv) provide a combination of (i) to (iii). As discussed with system 310, and as used again in reuse system 470, another option is to allow the dialysis fluid to circulate through dialyzer 396 a multitude of times. Chances are the dialysis fluid has not used all, or even close to all, of its osmotic or cleaning capacity the first time it is flowed through the dialyzer. Recycling the HD dialysis fluid allows all or most all of the osmotic potential to be realized.

HD example system 470 is very similar to HD system 310, wherein any and all like-numbered structure, functionality and alternatives discussed for system 310 are equally applicable to system 470. One primary difference is that system 310 may receive unpurified water from a pressurized tap water source, however, system 470 does not require a connection to a tap water source. Also, in system 310, drain line 364 extends to drain 62. In system 470, drain line 364 extends instead to storage tank 20. In this manner, used HD dialysis fluid and accumulated UF from Patient P is reused via distillation unit 10a to 10d. Control unit 314 for reuse HD system 470 is programmed accordingly to perform the reuse flow sequences discussed herein.

Reuse HD system 470, like reuse PD system 450, includes tap water storage tank 20, which again receives four liters of water initially but is sized to hold an additional amount of UF removed from Patient P. In reuse HD system 470, mixing tank 334 of HD machine 312 acts as the purified or WFI water accumulator 266 of reuse PD system 310. If deaeration and heating subassembly 340 is provided alternatively upstream of mixing subassembly 320, then expansion tank 342 of deaeration and heating subassembly 340 is used as the analogous structure to purified or WFI water accumulator 266 of reuse PD system 310.

In reuse HD system 470, at least four liters of tap water are placed in the tap water storage tank 20 (later becoming the drain). Distillation unit 10a to 10d prepares two liters of ultrapure water or WFI, which is delivered to and stored in mixing tank 334 while being mixed with HD concentrates to form HD dialysis fluid. The mixed HD dialysis fluid is then delivered to expansion tank 342 of deaeration and heating subassembly 340 for air removal and heating. Once the two liters of dialysis fluid are placed in the expansion tank 342, two actions may begin in parallel, namely, (i) dialysis fluid may be cycled through dialyzer 396 via dialysis fluid delivery subassembly 360 (e.g., two liters, five times, at 200 mL/min), while Patient P's blood is pumped through the dialyzer via blood pump 294 and (ii) distillation unit 10a to 10d prepares the second two liters of ultrapure water or WFI, which is likewise stored in mixing tank 334 while being mixed with HD concentrates to form HD dialysis fluid.

As illustrated, unpurified water pump 76a may be provided to pump unpurified water from storage tank 20 to heater 30 (heater 30 and condenser 80 are shown generally). Alternatively, head pressure in storage tank 20 is used to drive tap water to heater 30. Purified water pump 76b may also be provided to pump purified water to mixing tank 334 of HD machine 312.

At the end of the dialysis fluid circulation cycle using the first two liters of HD dialysis fluid, two more actions occur in parallel, namely, (a) used dialysis fluid and associated UF are delivered to water storage tank 20 (now drain) via dialysis fluid pump 374 (or instead a used dialysis fluid pump) and UF pump 380 and drain line 364, and (b) the mixed dialysis fluid in mixing tank 334 is delivered to expansion tank 342 for deaeration, heating and delivery to dialyzer 396. Once this is done, distillation unit 10a to 10d distills the used dialysis fluid and UF into ultrapure water or WFI and delivers same to mixing tank 334 for mixing into HD dialysis fluid. The above process is repeated until treatment is completed, e.g., after four to six dialysis fluid circulation cycles are performed. As with reuse PD system 450, drain 62 may not be needed with reuse HD system 470, except possibly to collect volatiles, impurities and HD concentration residuals due to the boiling at heater 30.

As discussed herein, circulating two liters of dialysis fluid, five times, at 200 mL/min, allows distillation unit 10a to 10d to create another batch of ultrapure water or WFI within fifty minutes at 1875 Watts of power to heater 30. It is contemplated again to provide one or more load cell 94 in distillation unit 10a to 10d beneath storage tank 20 and to be operable with control unit 24, so that it may be known when the two liters of ultrapure water or WFI has been produced via removal of tap water, used dialysis fluid, or combinations thereof from storage tank 20 and delivered to mixing tank 334.

It should be appreciated from the teachings of reuse HD system 470, that a reuse hemofiltration system starting from system 410 of FIG. 15 is also possible, e.g., by directing drain line 424 instead to a storage tank 20 located inside distillation unit 10a to 10d. A reuse hemodiafiltration machine and system may also be provided using the modifications for same discussed in connection with FIG. 15.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A fluid purification unit comprising:
    a heater configured to boil a fluid, the heater including first and second electrodes positioned and arranged to contact the fluid, the first and second electrodes configured to receive electrical power, heat resistively due to the electrical power, and transfer the heat to the fluid to boil the fluid to form water vapor; and
    a condenser including (i) a thermally conductive flowpath having an inlet fluidly coupled to the heater and an outlet for providing purified water, the thermally conductive flowpath configured to conductively cool the water vapor as the water vapor flows from the inlet to the outlet, and (ii) a cooling source configured to direct a cooling medium past the thermally conductive flowpath to convectively cool the water vapor, the conductive and convective cooling combining to condense the water vapor into the purified water.

2. The fluid purification unit of claim 1, wherein the thermally conductive flowpath includes a thermally conductive coil and the cooling source includes a fan positioned and arranged within the thermally conductive coil to blow the cooling medium outwardly through the thermally conductive coil to convectively cool the water vapor.

3. The fluid purification unit of claim 2, wherein the thermally conductive coil includes a plurality of heat fins for transferring heat from the water vapor.

4. The fluid purification unit of claim 3, wherein the thermally conductive coil is made from a first metal and the plurality of heat fins are made from a second metal.

5. The fluid purification unit of claim 2, wherein the thermally conductive coil is arranged to receive the water vapor at a top of the thermally conductive coil and to discharge the purified water at a bottom of the thermally conductive coil, and wherein the fan includes paddles arranged to spin around an at least substantially vertical axis to blow the cooling medium outwardly through the thermally conductive coil.

6. The fluid purification unit of claim 2, further comprising:
    a control unit configured to control the electrical power to the heater, and control a speed of the fan so as to provide the purified water at a desired temperature; and
    at least one valve positioned at least one of upstream of the heater or between the heater and the condenser, the at least one valve under control of the control unit.

7. The fluid purification unit of claim 6, further comprising a temperature sensor located downstream from the condenser and in communication with the control unit.

8. The fluid purification unit of claim 6, further comprising a vent line to atmosphere located between the heater and the condenser, the vent line operable with a vent valve under control of the control unit.

9. The fluid purification unit of claim 1, wherein the fluid purification unit is configured to accept either unpurified water or used dialysis fluid as the fluid to be boiled.

10. The fluid purification unit of claim 1, wherein the heater includes an insulative base into which the first and second electrodes are placed, and wherein the insulative base is sized to hold a desired amount of the fluid to be boiled.

11. The fluid purification unit of claim 10, wherein the insulative base is at least one of (a) configured to hold the first and second electrodes such that the first and second electrodes reside adjacent to one another in a non-contacting relationship, or (b) configured to sealingly receive first and second electrical leads that supply the electrical power from an electrical power source to the first and second electrodes, respectively.

12. The fluid purification unit of claim 10, wherein the insulative base is removable and disposable.

13. The fluid purification unit of claim 10, wherein the heater includes an insulative cover connected to the insulative base so as to allow access to the first and second electrodes, the insulative cover providing at least one port for at least one of (a) connection to a water source, or (b) connection to a vaporized fluid line.

14. The fluid purification unit of claim 1, wherein the first electrode includes first baffles and the second electrode includes second baffles, the first and second baffles interleaved with respect to each other in a non-contacting relationship.

15. The fluid purification unit of claim 1, further comprising a fluid storage tank positioned and arranged to provide the fluid to the heater.

16. The fluid purification unit of claim 1, further comprising at least one finishing filter located downstream from the condenser to further purify the purified water.

17. A dialysis system comprising:
    a dialysis unit including a fluid preparation structure configured to combine water for injection ("WFI") with at least one fluid concentrate to form dialysis fluid;
    a water purification unit embodied as the fluid purification unit according to claim 1, wherein the fluid is unpurified water; and
    at least one finishing filter positioned to receive and further purify the purified water into WFI for use with the fluid preparation structure.

18. The system of claim 17, wherein the dialysis fluid is a peritoneal dialysis fluid and the dialysis unit includes a peritoneal dialysis fluid pump arranged to pump the peritoneal dialysis fluid to and from a patient,
    wherein the fluid preparation structure employs the peritoneal dialysis fluid pump to combine the WFI with the at least one fluid concentrate, and
    wherein the peritoneal dialysis fluid pump is provided with the fluid preparation structure as part of a peritoneal dialysis cycler.

19. The system of claim 18, wherein the peritoneal dialysis fluid pump is under control of a first control unit and the water purification unit is under control of a second control unit, the first and second control units in data communication concerning at least one of (i) a demand for the WFI or, (ii) a capacity to produce the WFI.

20. A hemodialysis system comprising:
    at least one hemodialysis fluid pump arranged to pump hemodialysis fluid to and from a dialyzer;
    a hemodialysis fluid preparation structure configured to combine purified water with at least one hemodialysis fluid concentrate to form hemodialysis fluid; and
    a water purification unit embodied as the fluid purification unit according to claim 1, wherein the fluid is unpurified water.

21. The system of claim 20, wherein the at least one hemodialysis fluid pump is under control of a first control unit and the water purification unit is under control of a second control unit, the first and second control units in data communication concerning at least one of (i) a demand for the purified water, or (ii) a capacity to produce the purified water.

* * * * *